United States Patent [19]

Gohbara et al.

[11] Patent Number: 4,986,846
[45] Date of Patent: Jan. 22, 1991

[54] 2-(4,6-DIMETHOXY-2-PYRIMIDINYLOXY)-BENZALDOXIMES, PREPARATION PROCESSES THEREOF, HERBICIDES CONTAINING THE SAME, AND HERBICIDAL COMPOSITIONS CONTAINING THE SAME ALONG WITH OTHER ACTIVE INGREDIENT

[75] Inventors: Masatoshi Gohbara; Tamotsu Asano; Shuji Ozawa; Hideo Yamazaki; Tsutomu Ishii; Makoto Nishida, all of Kanagawa; Junko Watanabe, Tokyo; Naoki Sato, Fukuoka, all of Japan

[73] Assignee: Mitsui Toatsu Chemicals, Incorporated, Tokyo, Japan

[21] Appl. No.: 451,678

[22] Filed: Dec. 18, 1989

[30] Foreign Application Priority Data

Dec. 19, 1988 [JP] Japan .................. 63-318484

[51] Int. Cl.$^5$ .................. A01N 43/54; C07D 239/60
[52] U.S. Cl. .................. 71/92; 544/301
[58] Field of Search .................. 544/301; 71/92

[56] References Cited

U.S. PATENT DOCUMENTS 4,427,437 1/1984 Serban et al. .................. 544/299
4,770,691 9/1988 Nezu et al. .................. 544/310
4,889,552 12/1989 Wada et al. .................. 544/301

FOREIGN PATENT DOCUMENTS 227866 12/1984 Japan .................. 544/301

OTHER PUBLICATIONS

Serban et al., Chem. Abst. 92-175773f (1980).
Kijima et al, Chem. Abst. 93-150268c (1980), eq. JP 79117486.
Nezu et al., Chem. Abst. 107-134322t (1987).
Wada et al, Chem. Abst. 108-167496b (1988).

Primary Examiner—Cecilia Shen
Attorney, Agent, or Firm—Millen, White & Zelano

[57] ABSTRACT

Disclosed are herbicidally active pyrimidine derivatives of the formula

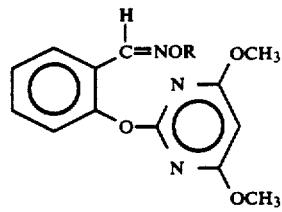

[I]

wherein R represents a hydrogen atom or an etherifying group, e.g., a lower alkyl, lower alkenyl, lower alkynyl, phenyl-substituted lower alkenyl, lower haloalkenyl, cycloalkyl, substituted phenyl-substituted lower alkenyl or phenyl-substituted lower alkynyl group; or a group represented by the following formula:

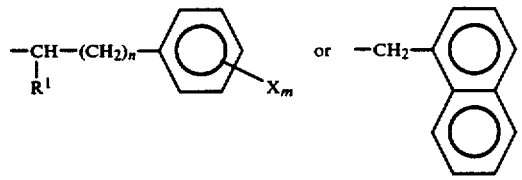

wherein $R^1$ represents a hydrogen atom or a lower alkyl group, X a halogen atom or a lower alkyl or lower alkoxyl group, m and n individually 0–2, and when m is 2, both Xs may be the same or different, and herbicidal compositions containing the same, alone or in combination with another herbicidally active compound, the pyrimidine derivatives being prepared by reaction of 2-(4,6-dimethoxy-2-pyrimidinyloxy)benzaldehyde with NH$_2$OR or with a salt of hydroxylamine followed by reaction with a halide of the formula RY wherein R has the same value as above and Y is Cl, Br or I.

19 Claims, No Drawings

2-(4,6-DIMETHOXY-2-PYRIMIDINYLOXY)BENZALDOXIMES, PREPARATION PROCESSES THEREOF, HERBICIDES CONTAINING THE SAME, AND HERBICIDAL COMPOSITIONS CONTAINING THE SAME ALONG WITH OTHER ACTIVE INGREDIENT

TECHNICAL FIELD

The present invention relates to novel pyrimidine derivatives, preparation processes thereof, herbicides containing the same, and herbicidal compositions containing the same along with another active ingredients.

RELATED ART

Pyrimidine derivatives having a phenoxy group at the 2-position which possess herbicidal activities are disclosed, for example, in Agric. Biol. Chem. 30(9), 896 (1966), Japanese Patent Laid-Open No. 55729/1979, Japanese Patent Laid-Open No. 117486/1979, Japanese Patent Publication No. 9474/1967, Japanese Patent Laid-Open No. 174059/1987, and Japanese Patent Laid-Open No. 115870/1988.

However, the compounds described in these publications are accompanied by the drawback that their herbicidal activities are insufficient or their tolerance to important crops involves problems when used in paddy fields or upland fields.

As a labor saving device, conventionally several types of herbicides are generally applied in combination to control weeds. However, sethoxydim, fluazifop and the like, which are extensively employed for the control of gramineous weeds in upland cropping, have the deficiency that they exhibit antagonism to herbicides for broad leaf weeds when used in combination therewith and their herbicidal activities are considerably reduced. Accordingly, these herbicides cannot be used to control gramineous weeds and broad leaf weeds with one treatment and therefore at least two foliar applications per year are required. This is both time consuming and increase the cost of controlling the weeds. Such antagonism is observed on many other herbicides. For example, the combined use of bensulfuron and a thiocarbonate-type herbicide in paddy fields reduces their herbicidal activities due to antagonism.

SUMMARY OF THE INVENTION

The present inventors have proceeded with an investigation on phenoxypyrimidine derivatives with a view toward obtaining herbicides which can exhibit, without crop injury, better controls even at a lower application rate compared with conventional herbicides and with a long period of application timing from an initial stage of emergence to the growth stage. The novel 2-phenoxypyrimidine derivatives of this invention, which contain a hydroxyiminomethyl group or a substituted or unsubstituted alkoxyiminomethyl group at the 2-position of the phenyl group have excellent properties as herbicides having a high degree of selectivity. They have the excellent selectivity in paddy field and upland field cropping. They have herbicidal activities even at low application rates against an extremely wide variety of weed species and they do not injure the harvest crops. These compounds have also been found to show synergistic herbicidal action when used in combination with other herbicides.

A first object of the invention is to provide novel pyrimidine derivatives.

A second object of the invention is to provide a process for the preparation of the pyrimidine derivatives of this invention.

A third object of the invention is to provide selective herbicides which in paddy field and/or upland field cropping, are effective even at low application rates against an extremely wide variety of weed species but do not injure important cash crops.

A fourth object of the invention is to provide composite herbicidal compositions comprising at least one pyrimidine derivative of this invention and at least one other herbicide, particularly such compositions which exhibit synergistic herbicidal action such that the herbicidal effects of the pyrimidine derivative of this invention therein is improved significantly to the extent that it is possible to reduce the application rate thereof and the herbicidal effects thereof last for several months after a single treatment.

The novel herbicidal compounds of this invention are 2-(4,6-dimethoxy-2-pyrimidinyloxy)benzaldoximes, i.e., 2-phenoxy-4,6-dimethoxy-pyrimidines bearing a free or etherified aldoximino group as an ortho substituent on the benzene ring.

The preferred novel compounds of the invention are pyrimidine derivatives which can be represented by the following formula [I]:

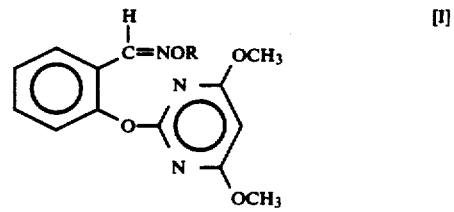

wherein R represents a hydrogen atom or an etherifying group, including a lower alkyl, lower alkenyl, lower alkynyl, phenyl-substituted lower alkenyl, lower haloalkenyl, cycloalkyl, substituted phenyl-substituted lower alkenyl or phenyl-substituted lower alkynyl group; or a group represented by the formula

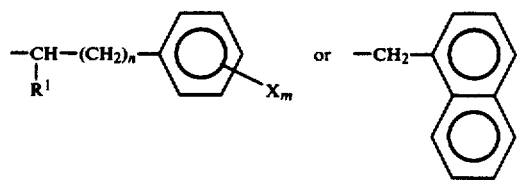

wherein $R^1$ represents a hydrogen atom or a lower alkyl group, X a halogen atom or a lower alkyl or lower alkoxyl group, m and n individually 0–2, and when m is 2, both Xs may be the same or different. In each instance, the term "lower" means containing up to 6 carbon atoms.

A preparation process of the invention for the preparation of the above pyrimidine derivative include the following Process A and Process B:

Process A:

-continued

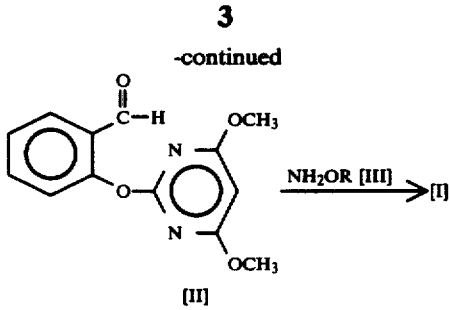

Process B:

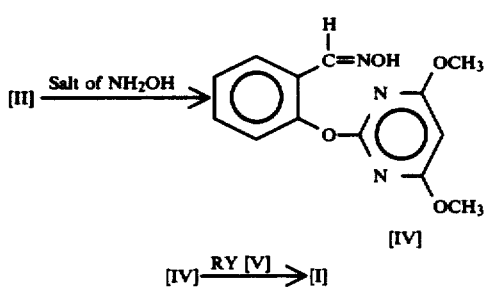

[IV] $\xrightarrow{RY\ [V]}$ [I]

In Process A, the pyrimidine derivative represented by the formula [I] can be obtained by reacting 2-(4,6-dimethoxy-2-pyrimidinyloxy)benzaldehyde of the formula [II] with a corresponding compound of the formula [III].

On the other hand, Process B includes two-step reactions.

In the first step, the starting material represented by the formula [II] is reacted with a hydroxylamine salt such as hydroxylamine hydrochloride, hydroxylamine sulfate or hydroxylamine oxalate to form 2-(4,6-dimethoxy-2-pyrimidinyloxy)benzaldoxime represented by the formula [IV]. Then, the compound is reacted with a halide represented by the formula [V] to obtain the pyrimidine derivative represented by the formula [I].

In the formulae [III] and [V], R has the same meaning as defined in the formula [I]. In the formula [V], Y represents a chlorine, bromine or iodine atom.

A selective herbicide according to the invention comprises, as an active ingredient, the pyrimidine derivative represented by the formula [I].

A preferred herbicidal composition according to this invention comprises, as herbicidally active ingredients, at least one pyrimidine derivative represented by the formula [I] and at least one other herbicidally active compound, preferably one which is effective against broad leaf weeds, e.g., the following compounds:

(i) compounds represented by the following formula [VI]:

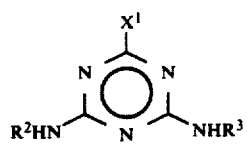

wherein $R^2$ represents an isopropyl or 2-cyano-1-methylethyl group, $R^3$ a methyl, ethyl or isopropyl group, and $X^1$ a chlorine atom or a methylthio group, (ii) compounds represented by the following formula [VII]:

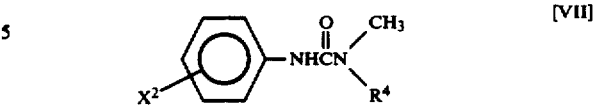

wherein $R^4$ represents a methyl or methoxy group and $X^2$ a 3-trifluoromethyl, 3,4-dichloro or 4-isopropyl group, (iii) compounds represented by the following formula [VIII]:

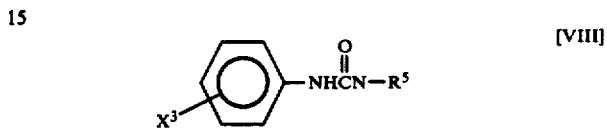

wherein $R^5$ represents an ethyl, n-propyl, α-methylbutyl or 2-methylpentenyl group and $X^3$ a 3,4-dichloro or 3-chloro-4-isopropyl group, (iv) compounds represented by the following formula [IX]:

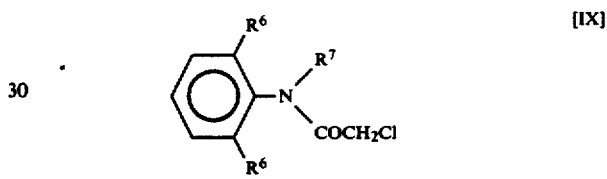

wherein $R^6$ represents a hydrogen atom or a methyl or ethyl group and $R^7$ a methoxymethyl. butoxymethyl, isopropyl or 2-methoxy-1-methylethyl group, (v) 4-amino-6-tert-butyl-3 methylthio-1,2,4-triazin-5(4H)-one, (vi) 3-isopropyl-(1H)-2,1,3-benzothiadiazin-4-(3H)-one-2,2-dioxide, and (vii) 2-(1-naphthalenylaminocarbonyl)benzoic acid.

DETAILED DESCRIPTION AND PREFERRED EMBODIMENTS OF THE INVENTION

Specific examples of R in the formula [I] include but are not limited to a hydrogen atom; linear or branched alkyl groups, preferably having 1–4 carbon atoms, e.g., methyl, ethyl, n-propyl, i-propyl, n-butyl, sec-butyl and tert-butyl; cycloalkyl groups, e.g., of 1–3 separate or fused rings and 3–12 ring carbon atoms, e.g., cyclopropyl, cyclobutyl, cyclopentyl and cyclohexyl; alkenyl groups, preferably of 2–6 carbon atoms, and the corresponding halo- and aryl-substituted alkenyl groups, including mono-, di- and tri-chloro, bromo-, fluoro- and phenyl-substituted alkenyl, e.g., 2-propenyl, 2-methyl-2-propenyl, 1-methyl-2-propenyl, 2-chloro-2-propenyl, 3-chloro-2-propenyl, 1-chloro-2-propenyl, 2,3-dichloro-2-propenyl, 3,3-dichloro-2-propenyl, 3-bromo-2-propenyl, 2-bromo-2-propenyl, 2-butenyl, 3-methyl-2-butenyl, 1-methyl-2-butenyl, 2-methyl-2-butenyl, 1,3-dimethyl-2-butenyl, 2,3-dimethyl-2-butenyl, 1,2-dimethyl-2-butenyl, 1-chloro-2-butenyl, 2-chloro-2-butenyl, 3-chloro-2-butenyl, 4-chloro-2-butenyl, 3-butenyl, 3-phenyl-2-butenyl, 3-phenyl-2-propenyl, 2-phenyl-2-propenyl, 2-phenyl-2-butenyl, 2-pentenyl and 2-hexenyl groups; alkynyl groups, preferably of 2–4 carbon atoms and the corresponding aryl-substituted alkynyl groups, including 2-propynyl, 2-butynyl, 3-phenyl-2-propynyl, 1-methyl-2-propynyl and 3-butynyl groups; aryl-substituted-alkyl, preferably phenyl-substituted alkyl groups wherein the aryl group can bear one, two or more substituents, e.g., alkyl, alkoxy and halo, e.g., benzyl, 2-chlorobenzyl, 2,4-dichlorobenzyl, 3,4-dichlorobenzyl, 4-methylbenzyl, 3-methylbenzyl, 2-fluorobenzyl, 2-bromobenzyl, 2-chloro-4-methylbenzyl, 2-phenylethyl, 1-methyl-2-phenylethyl, 1,1-dimethyl-2-phenylethyl, 1-(4-methylphenyl)ethyl, 2-(4-methylphenyl)ethyl, 2-(4-chlorophenyl)ethyl, 1-methyl-1-phenylethyl, 2-(2,4-dichlorophenyl)ethyl, 2-(2-fluorophenyl)ethyl, 1-phenylethyl and α-naphthylmethyl groups; substituted phenyl-substituted alkenyl, preferably propenyl groups, wherein the benzene ring can bear one, two or more substituents, e.g., alkyl, alkoxy and halo, e.g., 3-(2-chlorophenyl)-2-propenyl, 3-(3-chlorophenyl)-2-propenyl, 3-(4-chlorophenyl)-2-propenyl, 3-(2,3-dichlorophenyl)-2-propenyl, 3-(2,4-dichlorophenyl)-2-propenyl, 3-(3,4-dichlorophenyl)-2-propenyl, 3-(2-fluorophenyl)-2-propenyl, 3-(3-fluorophenyl)-2-propenyl, 3-(4-fluorophenyl)-2-propenyl, 3-(2,4-difluorophenyl)-2-propenyl, 3-(2-bromophenyl)-2-propenyl, 3-(2-iodophenyl)-2-propenyl, 3-(2-trifluoromethylphenyl)-2-propenyl, 3-(4-trifluoromethylphenyl)-2-propenyl, 3-(2-methylphenyl)-2-propenyl, 3-(3-methylphenyl)-2-propenyl, 3-(4-methylphenyl)-2-propenyl, 3-(4-ethylphenyl)-2-propenyl and 3-(3-methoxyphenyl)- 2-propenyl groups.

The preparation process represented by Process A is generally conducted in the presence of an inert solvent. By the term "inert solvent" as used herein, are meant, for example, alcohols such as methanol, ethanol and isopropyl alcohol. The reaction temperature may range from 0° C. to the boiling point of the solvent. It is however desirable to react them at 10°-30° C.

In Process B, the first-step reaction is generally conducted in the presence of a base in a mixed solvent of water and an alcohol. Further, the second-step reaction is generally carried out in the presence of a base in an inert solvent.

Examples of the bases in the preparation process represented by Process B include carbonates such as sodium carbonate, potassium carbonate, sodium bicarbonate and potassium bicarbonate and tertiary amines such as trimethylamine, triethylamine and pyridine.

The temperature of the first-step reaction in Process B, namely, the reaction temperature of the compound [II] and the hydroxylamine salt may range from 0° C. to the boiling point of the solvent. It is however desirable to conduct the reaction at about 10° C. to about 60° C.

The halide represented by the formula [V] and employed in the second-step reaction in Process B is generally used in an amount of from 1-5 mole equivalents relative to the compound generally represented by the formula [IV], namely, 2-(4,6-dimethoxy-2-pyrimidinyloxy)benzaldehydoxime. Examples of the inert solvent used upon conducting the second-step reaction include hydrocarbons such as benzene, toluene and xylene; halogenated hydrocarbons such as methylene chloride and chloroform; ethers such as diethyl ether, diisopropyl ether, tetrahydrofuran and 1,4-dioxane; ketones such as acetone and methyl ethyl ketone; esters such as methyl acetate and ethyl acetate; aprotic polar solvents such as dimethylformamide, dimethylacetamide, dimethylsulfoxide and 1,3-dimethyl-2-imidazolinone; and nitriles such as acetonitrile. The reaction temperature may range from room temperature to the boiling point of the solvent, with about 50° C. to about 120° C. being desired. After completion of the reaction, usual post treatments are conducted and the compound represented by the formula [I] can be purified by recrystallization or column chromatography.

The starting material in both Process A and Process B, i.e., 2-(4,6-dimethoxy-2-pyrimidinyloxy)benzaldehyde can be prepared by the process disclosed in Japanese Patent Laid-Open No. 174059/1987.

Chemically, the compounds according to the invention are novel compounds similar to the compounds disclosed in Japanese Patent Laid-Open No. 174059/1987 referred to above except that the formyl group bonded to the 2-position of the phenyl group has been replaced by a hydroxyiminomethyl group or a substituted or unsubstituted alkoxyiminomethyl group. Biologically however, owing to the above replacement, the compounds of the invention have been imparted with extremely good properties as paddy field herbicides and upland field herbicides. Namely, they are effective against substantially most of harmful weeds which cause problems in paddy fields and upland fields and moreover, show no or extremely little injury against broadleaf crops such as soybean, cotton, peanut and beet, to which the compounds disclosed in Japanese Patent Laid-Open No. 174059/1987 were not usable because of injury. The selectivity to these crops have therefore been improved significantly. Described specifically, the compounds of the invention can be used for broadleaf crops such as soybean, cotton, peanut, beet, potato and tobacco, and depending on the stage and method of application, for substantially all crops including corn, rice and wheat.

Herbicides containing one or more of the compounds of the invention, which are represented by the formula [I], act extremely effectively against substantially most of harmful weeds which cause problems in paddy fields or upland fields. In paddy fields, they show extremely good herbicidal effects for very troublesome gramineous weeds such as barnyardgrass, *Leersia oryzoides* and common reed; very troublesome cyperaceous weeds such as yellow nutsedge, smallflower umbrellaplant, *Cyperus seroyinus*, bulrush, *Scirpus nipponious*, *Eleocharis kuroguwai*, slender spikerush and *Fimbristylis miliacea*; very troublesome arrowhead weeds such as *Sagittaria pygmaea*, arrowhead and narrowleaf waterplantain; and broadleaf weeds such as *Monochoria vaginalis*, toothcup and parsnip. In upland fields, they exhibit superb herbicidal effects for broadleaf weeds such as common chickweed, common lambsquarters, shepherd's purse, redroot pigweed, hemp sesbania, prickly sida, velvetleaf, morningglories, common cocklebar and common groundsel; gramineous weeds such as barnyardgrass, green foxtail, large crabgrass, goosegrass, annual bluegrass, foxtail meadow, oat, wild oat, quackgrass, downy brome, bermudagrass, creeping bentgrass, broomsedge; silky bentgrass, singlegrass, fall panicum, johnsongrass and shattercane; cyperaceous weeds such as rice flatsedge and yellow/purple nutsedge; especially perennial weeds such as johnsongrass, shattercane and orchardgrass.

From the results of an enzyme assay on the enzyme, ALS (acetolactate syntase), which is believed to be a target site of the herbicides containing one or more of the compounds of the invention, which are represented by the formula [I], have been found to show high inhibitory activities against weeds such as barnyardgrass, johnsongrass and green foxtail. In contrast, they do not show inhibitory activities against broadleaf crops such as pea, cotton and peanut. These results indicate that the broadleaf crops such as pea, cotton, peanut and the like show high tolerance against the herbicides according to the invention. In pot tests, they were also found to show no injury or even if any, extremely slight injury against broadleaf crops such as soybean, cotton, beet, peanut, common sunflower, rape and greens. Depending on the method of application, they can also be used, without any injury, for gramineous crops such as corn, wheat, rice, barley and sugar cane. Especially, they can be used effectively for cotton, soybean and peanut without injury.

The herbicides containing one or more of the compounds of the invention, which are represented by the formula [I], are effective in all application methods such as soil application, soil incorporation, foliar application and band application.

Upon application of the compounds of the formula [I] according to this invention as herbicides, they may be applied neat to weeds to be treated. In general, they are however mixed with an inert liquid carrier or solid carrier and formed into a commonly-used formulation such as powder, granules, wettable powder, emulsion or flowable formulation. One or more auxiliary agents can also be added if necessary for formulation.

Any carrier can be used as long as it is usable in conventional agricultural or horticultural chemicals, no matter whether it is solid or liquid. No particular limitation is therefore imposed on the carrier.

Exemplary solid carriers include mineral powders such as clay, talc, bentonite, calcium carbonate, diatomaceous earth and white carbon; vegetable powders such as soybean flour and starch; high molecular compounds such as petroleum resins, polyvinyl alcohol and polyalkylene glycols; urea; and waxes. Illustrative liquid carriers include various organic solvents such as xylene, methylnaphthalene and alkylbenzenes; various oils such as vegetable oils; and water.

As auxiliary agents, surfactants, binders, stabilizers and the like which are generally used in agricultural or horticultural chemicals can be used either singly or in combination. In some instances, industrial fungicides, antiseptics and the like can also be incorporated for the control of bacteria and fungi.

As exemplary surfactants, non-ionic, anionic, cationic and amphoteric surfactants can be used either singly or in combination. Those obtained by adding ethylene oxide or propylene oxide to alkyl phenols, higher alcohols, alkylnaphthols, higher fatty acids, fatty acid esters and the like can be used as preferred non-ionic surfactants. Exemplary anionic surfactants include the alkylsulfonate salts, alkyl sulfate ester salts, phosphate ester salts, lignine sulfonate salts and the like of alkylphenols, alkylnaphthols, higher alcohols, higher fatty acids, fatty acid esters and the like. Illustrative binders include lignine sulfonic acid, alginic acid, polyvinyl alcohol, gum arabic, CMC (sodium carboxymethylcellulose), etc.

As exemplary stabilizers, phenolic compounds, thiol compounds, high molecular fatty acid esters and the like can be used for the protection from oxidation. In addition, phosphate salts can be used as pH regulators. Light stabilizers may also be used if necessary.

The content of each compound of the formula [I] in the associated herbicide according to the invention varies depending on the formulation. In general, it can be 0.05-20 wt. % in a powder, 1-50 wt. % in a wettable powder, 0.05-15 wt. % in a granule, 1-50 wt. % in an emulsion, 1-50 wt. % in a flowable formulation and 1-50 wt. % in a dry flowable formulation. Preferably, it can be 0.5-5 wt. % in a powder, 10-40 wt. % in a Wettable powder, 0.5-8 wt. % in a granule, 5-20 wt. % in an emulsion, 10-30 wt. % in a flowable formulation and 10-40 wt. % in a dry flowable formulation.

The total content of auxiliary agents may be 0-80 wt. %. The content of the carrier is the value which is obtained by subtracting the contents of the compound as an active ingredient and of auxiliary agents.

When the compounds of the invention are used in paddy fields or upland fields, the application rate can be 0.1-10 kg/ha, preferably 0.5-5 kg/ha in terms of active ingredient.

The herbicides of the invention, which contains the compounds represented by the formula [I], may be formulated together with one or more other herbicides or one or more of agricultural chemicals such as fungicides, insecticides and plant growth regulators, fertilizers and soil improving agents, to say nothing of combined use therewith.

In particular, the compounds according to the invention exhibited surprisingly high synergistic herbicidal effects when combined with photosynthesis-inhibiting herbicides (for example, urea herbicides, triazine herbicides, anilide herbicides or bentazon, etc.) When the compounds of the invention were used, for example, with diuron, triazine, Propanil, Bentazon and the like, unexpectedly excellent activities were shown compared to the herbicidal effects available when they were applied singly, thereby making it possible to apply at a lower rate. Furthermore, the herbicidal effects have been found to last for several months even when treated only once.

Illustrative compounds of the formula [VI], which can be mixed with the pyrimidine derivatives of formula [I] to form compositions according to the invention, include 2-chloro-4-ethylamino-6-isopropylamino-1,3,5-triazine (atrazine), 2-(2-chloro-4-ethylamino-1,3,5-triazine-6-ylamino)-2-methylpropionitrile (cyanazine), 2-methylthio-4-methylamino-6-isopropylamino-1,3,5-triazine (ametryn), 2-methylthio-4,6-bis(isopropylamino)-1,3,5-triazine (prometryn), 2-chloro-4,6-bis(ethylamino)-1,3,5-triazine (simazine), 2-methoxy-4,6-bis(isopropylamino)-1,3,5-triazine (prometon), and 2-methylthio-4,6-bis(ethylamino)-1,3,5-triazine (simetryn).

Exemplary compounds represented by the formula [VII] include 3-(3,4-dichlorophenyl)-1,1-dimethylurea (diuron), 3-(3,4-dichlorophenyl)-1-methoxy-1-methylurea (linuron), 3-(4-isopropylphenyl)-1,1-dimethylurea (isoproturon), 1,1-dimethyl-3-(3-trifluoromethylphenyl)urea (fluometuron), and 3-(4-chlorophenyl)-1,1-dimethylurea (monuron).

Exemplary compounds represented by the formula [VIII] include N-(3,4-dichlorophenyl)propanamide (propanil), N-(3-chloro-4-isopropylphenyl)-2-methylpentamide (MT-5950), and 3,4-dichloro-2-methylacrylanilide (dicryl).

Illustrative compounds represented by the formula [IX] include 2-chloro-N-isopropylacetanilide (propachlor), N-methoxymethyl-2',6'-diethyl-2-chloroacetanilide (alachlor), 2-chloro-2',6'-diethyl-N-(butoxymethyl)acetanilide (butachlor), and 2-chloro-2'-ethyl-6'-methyl-N-(2-methoxy-1-methylethyl)acetanilide (metolachlor).

Against the upland weeds to which the aforementioned compounds represented by the formula [I] show effects, the compositions according to the invention can exhibit unexpectedly high synergistic effects compared to those available when the compounds are used singly. Their herbicidal effects have been improved 5-10 times and moreover, the thus-improved herbicidal effects last for several months. In addition, as a result of the improved effects, the application rate can be reduced so that the compositions of the invention can be used very safely for soybean, cotton, peanut, beet, corn, rice, wheat and the like without injury.

Furthermore, when the compounds of the formula [I] according to the invention are applied singly, 30-50 days are required until their action is exhibited. In contrast, the herbicidal compositions according to the invention can exhibit their action in 3-10 days after treatment, thereby making it possible to provide a significant contribution for increased yields of crops.

The contents of active ingredients in each herbicidal composition of the invention widely vary depending on the kind of a weed to be controlled, the leaf stage of the weed, the kind of the other ingredient to be mixed, and other conditions. Per part by weight of the compound of the formula [I], the other compound can however be used in an amount of 0.05-100 parts by weight, preferably 0.1-80 parts by weight.

Similarly to the herbicides containing the compounds represented by the formula [I], the herbicidal compositions according to the invention are effective in all application methods such as soil application, soil incorporation application, foliar application and band application.

Upon application of each herbicidal compositions according to this invention, the mixture of its active ingredients can be used neat. In general, the active ingredients are however mixed with an inert liquid carrier or solid carrier and formed into a commonly-used formulation such as powder, granules, wettable powder, emulsion or flowable formulation. One or more auxiliary agents can also be added if necessary for formulation. Usable carriers and auxiliary agents are similar to those described above with respect to the herbicides containing the compounds represented by the formula [I].

When the herbicidal compositions according to the invention are used in upland fields, the application rate varies depending on various factors, for example, the target weed, the target crop, the method and timing of application, the weather, the type of soil, and the kinds of active ingredients combined. The application rate can be 0.05-5 kg/ha, preferably 0.1-3 kg/ha in terms of active ingredients.

EXAMPLES

Preparation examples of certain pyrimidine derivatives according to the invention will be described hereinafter.

REFERENTIAL EXAMPLE 1

Preparation of 2-chloro-4,6-dimethoxypyrimidine 1,260 ml of 36% hydrochloric acid were charged in a 5-l four-necked flask and then cooled to 0° C. After 180 g (1.16 moles) of 2-amino-4,6-dimethoxypyrimidine were added in small portions into the flask, the resulting mixture was stirred for about 1 hour until the reaction mixture changed into a syrupy form. After the reaction mixture was cooled to −15° C., 260 ml of 159 g (2.3 moles) of NaNO$_2$ in H$_2$O were added dropwise over about 1 hour under vigorous stirring. After completion of the dropwise addition, the resulting mixture was stirred at −15° to −10° C. for additional 1 hour so that the reaction was brought to completion. While the reaction mixture was retained at −5° C., 1.5 l of a 30% aqueous solution of NaOH were charged dropwise so that the reaction mixture was neutralized to pH 7. By filtration under reduced pressure, a clay-like material of a purple color was collected. The target compound was extracted from the clay-like material using 3 l of ethyl acetate. Through the procedures of washing with water, drying over anhydrous sodium sulfate and removal of the solvent, 63 g of bluish crude crystals were obtained. They were crystallized further by silica gel chromatography to obtain 60.8 g of white crystals (yield: 29.9%).

Melting point: 101.5°-102.5° C.

REFERENTIAL EXAMPLE 2

Synthesis of 2-(4,6-dimethoxy-2-pyrimidinyloxy)benzaldehyde

A 500-ml four-necked flask was charged with a mixture of 105 g (0.6 mole) of 2-chloro-4,6-dimethoxypyrimidine, 79.4 g (0.65 mole) of salicylic aldehyde 48.3 g (0.35 mole) of potassium carbonate and 450 ml of dimethylsulfoxide. The mixture was gradually heated, and stirred at 120° C. for 3 hours. After the reaction mixture was cooled, it was poured into 2 l of water. Through the procedures of benzene extraction, washing with water, drying over anhydrous sodium sulfate and concentration, 156 g of the target product were obtained as a crude oil. It was purified further by silica gel chromatography to obtain 117.1 g of white crystals (yield: 75.0%).

Melting point: 76.0°-about 76.5° C.

EXAMPLE 1

Preparation of O-methyl-2-(4,6-dimethoxy-2-pyrimidinyloxy)benzaldoxime (Compound No. 1)

In 100 ml of methanol, 5.2 g of 2-(4,6-dimethoxy-2-pyrimidinyloxy)benzaldehyde and 1.0 g of methoxyamine were dissolved. The solution was stirred at room temperature for 2 hours. After the methanol was distilled out under reduced pressure, the resulting residue was purified by silica gel chromatography (developer: n-hexane:ethyl acetate=10:1) to obtain 5.7 g of O-methyl-2-(4,6-dimethoxy-2-pyrimidinyloxy)benzaldehyde as an oily substance.

H-NMR spectrum (CDCl$_3$-TMS) δ: 3.42(3H,s), 3.77(3H,s), 5.71(1H,s), 7.0–8.0(4H,m), 8.20(1H,s).

EXAMPLE 2

Preparation of 2-(4,6-dimethoxy-2-pyrimidinyloxy)-benzaldoxime (Compound No. 24)

3.5 g of hydroxylamine hydrochloride were added to 100 ml of a 1:1 mixed solution of water and methanol containing 3.5 g of potassium carbonate at 0° C. The solution was stirred at 0° C. for 10 minutes. At 0° C., 13.0 g of 2-(4,6-dimethoxy-2-pyrimidinyloxy)benzaldehyde were added to the reaction mixture. The resulting mixture was stirred at room temperature for 1 hour and then warmed at 60° C. for 1 hour. After the reaction mixture was allowed to cool down, it was poured into water, followed by extraction with ethyl acetate. The organic layer was dried over anhydrous sodium sulfate and then concentrated under reduced pressure. The residue was purified by silica gel chromatography (developer: n-hexane:ethyl acetate=5:1) to obtain 7.7 g of 2-(4,6-dimethoxy-2-pyrimidinyloxy)benzaldoxime.

Melting point: 125°–128° C.

H-NMR spectrum (CDCl$_3$-TMS) δ: 3.76(6H,s), 5.74(1H,s), 7.1–7.9(4H,m), 8.35(1H,s), 9.30(1H,bs).

EXAMPLE 3

Preparation of O-(2,4-dichlorobenzyl)-2-(4,6-dimethoxy-2-pyrimidinyloxy))-benzaldoxime (Compound No. 17)

5.2 g of 2-(4,6-dimethoxy-2-pyrimidinyloxy)benzaldehyde and 3.8 g of 2,4-dichlorobenzyloxyamine were dissolved in 100 ml of methanol and the solution was stirred at room temperature for 2 hours. After the methanol was distilled out under reduced pressure, the resulting residue was recrystallized from isopropyl ether to obtain 8.1 g of O-(2,4-dichlorobenzyl)-2-(4,6-dimethoxy-2-pyrimidinyloxy)benzaldoxime.

Melting point: 108°–110.5° C.

H-NMR spectrum (CDCl$_3$-TMS) δ: 3.72(6H,s), 5.15(2H,s), 5.63(1H,s), 6.9–7.5(6H,m), 7.7–7.9(1H,m), 8.18(1H,s).

EXAMPLE 4

Preparation of O-(2-propynyl)-2-(4,6-dimethoxy-2-pyrimidinyloxy)benzaldoxime (Compound No. 13)

5.5 g of 2-(4,6-dimethoxy-2-pyrimidinyloxy)benzaldoxime and 7.1 g of propargyl bromide were dissolved in 100 ml of N,N-dimethylformamide containing 1.4 g of potassium carbonate, and the solution was stirred at 100° C. for 4 hours. After the reaction mixture was allowed to cool down, it was poured into water, followed by extraction with ethyl acetate. The organic layer was dried over anhydrous sodium sulfate and then concentrated under reduced pressure. The residue was purified by silica gel chromatography (developer: n-hexane:ethyl acetate=10:1) to obtain 4.8 g of O-(2-propynyl)-2-(4,6-dimethoxy-2-pyrimidinyloxy)benzaldoxime as an oily substance.

H-NMR spectrum (CDCl$_3$-TMS) δ: 2.32(1H,t,J=2.4 Hz), 3.75(6H,s), 4.65(2H,d,J=2.4 Hz), 5.68(1H,s), 6.9–7.4(3H,m), 7.7–8.0(1H,m), 8.20(1H,s).

EXAMPLE 5

Preparation of O-(3-chlorocinnamyl)-2-(4,6-dimethoxy-2-pyrimidinyloxy)benzaldoxime (Compound No. 26)

5.5 g of 2-(4,6-dimethoxy-2-pyrimidinyloxy)benzaldoxime and 4.6 g of 3-chlorocinnamyl bromide were dissolved in 30 ml of dry acetone containing 2.7 g of anhydrous potassium carbonate. The solution was heated for 5 hours under stirring and reflux. After the reaction mixture was allowed to cool down, the acetone was distilled out under reduced pressure and the resulting residue was dissolved in 200 ml of ethyl acetate. The ethyl acetate solution was washed with water and the organic layer was dried over anhydrous sodium sulfate. The solution was then concentrated under reduced pressure. The residue was purified by silica gel chromatography (developer: n-hexane:ethyl acetate: 4:1) to obtain 5.2 g of O-(3-chlorocinnamyl)-2-(4,6-dimethoxy-2-pyrimidinyloxy)benzaldoxime as a semi-solid substance.

H-NMR spectrum (CDCl$_3$-TMS) δ: 3.77(6H,s), 4.77(2H,d,J=6.0 Hz), 5.77(1H,s), 6.35(1H,dt,J=16.0,6.0 Hz), 6.56(1H,d,J=16.0 Hz), 7.21–7.25(5H,m), 7.35–7.41(2H,m), 7.86–7.90(1H,m), 8.27(1H,s).

EXAMPLE 6

Preparation of O-(3-methylcinnamyl)-2-(4,6-dimethoxy-2-pyrimidinyloxy)benzaldoxime (Compound No. 34)

5.5 g of 2-(4,6-dimethoxy-2-pyrimidinyloxy)benzaldoxime and 4.2 g of 3-methylcinnamyl bromide were dissolved in 30 ml of acetonitrile containing 2.7 g of anhydrous potassium carbonate, and the solution was heated for 5 hours under stirring and reflux. After the reaction mixture was allowed to cool down, the acetonitrile was distilled out under reduced pressure and the resulting residue was dissolved in 200 ml of ethyl acetate. The ethyl acetate solution was washed with water and the organic layer was dried over anhydrous sodium sulfate. The solution was then concentrated under reduced pressure. The residue was purified by silica gel chromatography (developer: n-hexane:ethyl acetate: 4:1) to obtain 5.2 g of O-(3-methylcinnamyl)-2-(4,6-dimethoxy-2-pyrimidinyloxy)benzaldoxime as crystals.

H-NMR spectrum (CDCl$_3$-TMS) δ: 2.32(3H,s), 3.76(6H,s), 4.77(2H,d,J=6.0 Hz), 5.74(1H,s), 6.33(1H,dt,J=16.0,6.0 Hz), 6.59(1H,d,J=16.0 Hz), 6.81–7.40(7H,m), 7.87–7.91(1H,m), 8.28(1H,s).

EXAMPLE 7

Preparation of O-cinnamyl-2-(4,6-dimethoxy-2-pyrimidinyloxy)benzamidoxime (Compound No. 9)

(1) Preparation of N-cinnamyloxyphthalimide:

In 200 ml of DMF, 41.4 g of N-hydroxyphthalimide and 18 g of potassium carbonate were suspended. Fifty grams of cinnamyl bromide were added, followed by stirring at 120° C. for 5 hours. After completion of the reaction, the reaction mixture was cooled and then poured into about 500 ml of water. Crystals thus precipitated were collected by filtration, dried and then recrystallized from a mixed solvent of acetone and isopropyl ether, thereby obtaining 41.9 g of N-cinnamyloxyphthalimide.

Yield: 59.1%.

(2) Preparation of cinnamyloxyamine:

In 600 ml of methanol, 27.9 g of N-cinnamyloxyhthalimide obtained in the procedure (1) were suspended. After the suspension was heated at 50° C., 10 ml of a methanol solution of 5 g of hydrazine monohydrate were added dropwise. The resultant mixture was then stirred at the same temperature for 1 hour. Thereby, a methanol solution of cinnamyloxyamine was obtained.

(3) Preparation of O-cinnamyl-2-(4,6-dimethoxy-2-pyrimidinyloxy)benzamidoxime:

19.5 g of 2-(4,6-dimethoxy-2-pyrimidinyloxy)benzaldehyde were added in the methanol solution of cinnamyloxyamine prepared in the procedure (2) at 50° C. The resultant mixture was then heated under reflux at the same temperature for 1 hour, whereby the reaction was brought to completion. After the reaction mixture was cooled, the solvent was distilled out under reduced pressure and the resultant residue was dissolved in 500 ml of isopropyl ether. Insoluble matter was filtered off and the solvent was distilled off under reduced pressure from the filtrate, whereby an oily crude product was obtained. The crude product was purified by chromatography on a silica gel column (developer: n-hexane:ethyl acetate=10:1), followed by recrystallization from isopropyl ether to obtain 25.1 g of the target product, O-cinnamyl-2-(4,6-dimethoxy-2-pyrimidinyloxy)-benzamidoxime.
Yield: 85.6%.
Melting point: 87°-89° C.
H-NMR spectrum (CCl₄-TMS) δ: 3.75(6H,s), 4.75(2H,d,J=5.4 Hz), 5.70(1H,s), 6.27(1H,dt,J=15.8,J=5.4 Hz), 6.64(1H,d,J=15.8 Hz), 7.0-7.5(8H,m), 7.8-8.0(1H,m), 8.23(1H,s).

Regarding typical examples of the pyrimidine derivatives of the invention represented by the formula [I], their melting points, the distinction of the process used (Process A or Process B) and their NMR spectrum data are summarized in Table 1.

TABLE 1

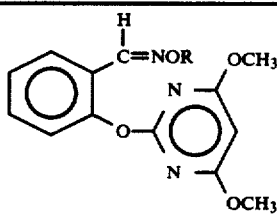
(I)

| Compound No. | R | M.P. (°C.) | Preparation process | NMR spectrum |
|---|---|---|---|---|
| 1 | —CH₃ | Oily | A | (CDCl₃) δ 3.42(3H,s), 3.77(6H,s), 5.71(1H,s), 7.0-8.0(4H,m), 8.2(1H,s) |
| 2 | —CHCH=CH₂<br>\|<br>CH₃ | Oily | A | (CCl₄) δ 1.32(3H,d,J=6.4Hz), 3.73(6H,s), 4.4-4.8(1H,m), 4.9-5.3(2H,m), 5.65(1H,s), 5.6-6.2(1H,m), 6.9-7.4(3H,m), 7.7-7.9(1H,m), 8.11(1H,s) |
| 3 | cyclohexyl | 96-97 | A | (CCl₄) δ 1.1-2.1(10H,m), 3.77(6H,s), 3.9-4.3(1H,m), 5.6-6.3(1H,m), 6.9-7.4(3H,m), 7.7-7.9(1H,m), 8.13(1H,s) |
| 4 | —CH₂CH=CH₂ | Oily | A | (CCl₄) δ 3.73(6H,s), 4.5-4.7(2H,m), 5.0-5.4(2H,m), 5.66(1H,s), 5.6-6.3(1H,s), 6.9-7.4(3H,m), 7.7-7.9(1H,s), 8.13(1H,s) |
| 5 | CH₃<br>\|<br>—CH₂C=CH₂ | Oily | A | (CCl₄) δ 1.73(3H,s), 3.70(6H,s), 4.43(2H,s), 4.7-5.0(2H,m), 5.58(1H,s), 6.9-7.3(3H,m), 7.7-7.9(1H,m), 8.07(1H,s) |
| 6 | —CH—CH₃<br>\|<br>CH₃ | Oily | A | (CCl₄) δ 1.25(6H,d,J=6.4Hz), 3.78(6H,s), 4.1-4.6(1H,m), 5.70(1H,s), 6.9-7.4(3H,m), 7.8-8.0(1H,m) |
| 7 | —CH₂CH=C(CH₃)₂ | Oily | A | (CCl₄) δ 1.70(6H,s), 3.70(6H,s), 4.47(2H,d,J=7.0Hz), 5.30(1H,t,J=7.0Hz), 5.60(1H,s), 6.8-7.2(3H,m), 7.7-7.9(1H,m), 7.97(1H,s) |
| 8 | —CH₂CH=CHCH₃ | Oily | A | (CCl₄) δ 1.6-1.8(6H,m), 3.77(6H,s), 4.4-4.6(2H,m), 5.5-5.8(3H,m), 6.9-7.4(3H,m), 7.8-8.0(1H,m), 8.15(1H,s) |
| 9 | —CH₂CH=CH—Ph | Oily | A | (CCl₄) δ 3.75(6H,s), 4.75(2H,d,J=5.4Hz), 5.70(1H,s), 6.27(1H,dt,J=15.8,J=5.4Hz), 6.64(1H,d,J=15.8Hz), 7.0-7.5(8H,m), 7.8-8.0(1H,m), 8.23(1H,s) |
| 10 | —CH₂C≡CCH₃ | Oily | A | (CCl₄) δ 1.85(3H,t,J=2.4Hz), 3.8(6H,s), 4.62(2H,q,J=2.4Hz), 5.70(1H,s), 6.9-7.4(3H,m), 7.8-8.0(1H,m), 8.20(1H,s) |
| 11 | —CH₂CH=CHCl | Oily | A | (CCl₄) δ 3.76(6H,s), 4.5-4.9(2H,m), 5.67(1H,s), 5.9-6.2(2H,m), 7.0-7.4(3H,m), 7.7-7.9(1H,m), 8.13(1H,s) |
| 12 | Cl<br>\|<br>—CH₂CH=CCH₃ | Oily | A | (CCl₄) δ 2.1-2.2(3H,m), 3.77(6H,s), 4.6-4.8(2H,m), 5.70(1H,s), 5.6-5.9(1H,m), 7.0-7.4(3H,m), 7.8-8.0(1H,m), 8.13(1H,s) |
| 13 | —CH₂C≡CH | Oily | B | (CCl₄) δ 2.32(1H,t,J=2.4Hz), 3.75(6H,s), 4.65(2H,d,J=2.4Hz), |

TABLE 1-continued (I)

[Structure: benzene ring with CH=NOR group, connected via O to pyrimidine ring with two OCH₃ groups and two N atoms]

| Compound No. | R | M.P. (°C.) | Preparation process | NMR spectrum |
|---|---|---|---|---|
| | | | | 5.68(1H,S), 6.9-7.4(3H,m), 7.7-8.0(1H,m), 8.20(1H,s) |
| 14 | -CH₂C(Cl)=CH₂ | Oily | A | (CCl₄) δ 3.73(6H,s), 4.6-4.7(2H,m), 5.3-5.4(2H,m), 5.67(1H,s), 6.9-7.4(3H,m), 7.7-7.9(1H,m), 8.20(1H,s) |
| 15 | -CH₂-phenyl | Oily | A | (CDCl₃) δ 3.76(6H,s), 5.15(2H,s), 5.72(1H,s), 7.0-8.0(9H,m), 8.28(1H,s) |
| 16 | -CH₂-(2-Cl-phenyl) | Oily | A | (CCl₄) δ 3.72(6H,s), 5.22(2H,s), 5.65(1H,s), 6.9-7.5(7H,m), 7.7-7.9(1H,m), 8.23(1H,s) |
| 17 | -CH₂-(2,4-diCl-phenyl) | 108-110.5 | A | (CCl₄) δ 3.72(6H,s), 5.15(2H,s), 5.63(1H,s), 6.9-7.5(6H,m), 7.7-7.9(1H,m), 8.13(1H,s) |
| 18 | -CH₂-(2,3-diCl-phenyl) | 114-115.5 | A | (CCl₄) δ 3.70(6H,s), 5.00(2H,s), 5.63(1H,s), 6.9-7.4(6H,m), 7.7-7.9(1H,m), 8.13(1H,s) |
| 19 | -CH₂-(4-Me-phenyl) | Oily | A | (CCl₄) δ 2.30(3H,s), 3.70(6H,s), 5.00(2H,s), 5.62(1H,s), 6.9-7.4(7H,m), 7.7-7.9(1H,m), 8.10(1H,s) |
| 20 | -CH₂-(2-Me-phenyl) | Oily | A | (CCl₄) δ 2.33(3H,s), 3.70(6H,s), 5.03(2H,s), 5.62(1H,s), 6.9-7.4(7H,s), 7.7-7.9(1H,s), 8.13(1H,s) |
| 21 | -CH(Me)-phenyl | Oily | A | (CCl₄) δ 1.20(3H,d,J=6.8Hz), 3.70(6H,s), 5.23(1H,q,J=6.8Hz), 5.67(1H,s), 6.9-7.3(8H,m), 7.7-7.9(1H,m), 8.20(1H,s) |
| 22 | -CH₂-naphthyl | Oily | A | (CCl₄) δ 3.67(6H,s), 5.55(2H,s), 5.63(1H,s), 6.9-7.6(7H,m), 7.6-8.2(4H,m), 8.20(1H,s) |

TABLE 1-continued

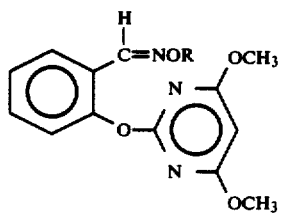

(I)

| Compound No. | R | M.P. (°C.) | Preparation process | NMR spectrum |
|---|---|---|---|---|
| 23 | —C₂H₄—C₆H₅ | Oily | A | (CCl₄) δ 2.93(2H,t,J=7.2Hz), 3.70(6H,s), 4.23(2H,t,J=7.2Hz), 5.63(1H,s), 6.9–7.5(8H,m), 7.7–8.0(1H,m), 8.10(1H,s) |
| 24 | H | 128.5–130 | A | (CDCl₃) δ 3.76(6H,s), 5.74(1H,s), 7.1–7.9(4H,m), 8.35(1H,s), 9.3(1H,bs) |
| 25 | —CH₂CH=CH—C₃H₇ | Oily | A | (CDCl₃) δ 0.7–1.1(3H,m), 1.2–1.7(4H,m), 3.76(6H,s), 4.4–4.6(2H,m), 4.9–5.3(2H,m), 5.67(1H,s), 6.9–7.3(3H,m), 7.7–7.9(1H,m), 8.12(1H,m) |
| 26 | —CH₂CH=CH—(3-Cl-C₆H₄) | Semi-solid | B | (CDCl₃) δ 3.77(6H,s), 4.77(2H,d,J=6Hz), 5.74(1H,s), 6.35(1H,dt,J=16Hz,J=6Hz), 6.56(1H,d,J=16Hz), 7.21–7.25(5H,m), 7.35–7.41(2H,m), 7.86–7.90(1H,m), 8.27(1H,s) |
| 27 | —CH₂CH=CH—(2-Cl-C₆H₄) | Oily | B | (CDCl₃) δ 3.77(6H,s), 4.81(2H,d,J=6Hz), 5.73(1H,s), 6.33(1H,dt,J=16Hz,J=6Hz), 7.01(1H,d,J=16Hz), 7.13–7.54(7H,m), 7.89–7.91(1H,m), 8.28(1H,s) |
| 28 | —CH₂CH=CH—(4-Cl-C₆H₄) | 103–104 | B | (CDCl₃) δ 3.78(6H,s), 4.77(2H,d,J=6Hz), 5.74(1H,s), 6.33(1H,dt,J=16Hz,J=6Hz), 6.58(1H,d,J=16Hz), 7.14–7.42(7H,m), 7.86–7.90(1H,m), 8.27(1H,s) |
| 29 | —CH₂CH=CH—(4-F-C₆H₄) | 92–93 | B | (CDCl₃) δ 3.79(6H,s), 4.76(2H,d,J=6Hz), 5.75(1H,s), 6.33(1H,dt,J=16Hz,J=6Hz), 6.58(1H,d,J=16Hz), 7.14–7.42(7H,m), 7.86–7.90(1H,m), 8.27(1H,s) |
| 30 | —CH₂CH=CH—(2,4-Cl₂-C₆H₃) | 90–91 | B | (CDCl₃) δ 3.77(6H,s), 4.80(2H,d,J=6Hz), 5.74(1H,s), 6.32(1H,dt,J=16Hz,J=6Hz), 6.92(1H,d,J=16Hz), 7.14–7.47(6H,m), 7.89–7.90(1H,m), 8.28(1H,s) |
| 31 | —CH₂CH=CH—(3,4-Cl₂-C₆H₃) | 93–94 | B | (CDCl₃) δ 3.78(6H,s), 4.77(2H,d,J=6Hz), 5.75(1H,s), 6.34(1H,dt,J=16Hz,J=6Hz), 7.02(1H,d,J=16Hz), 7.14–7.45(6H,m), 7.86–7.89(1H,m), 8.28(1H,s) |
| 32 | —CH₂CH=CH—(2-CF₃-C₆H₄) | Oily | B | (CDCl₃) δ 3.77(6H,s), 4.82(2H,d,J=6Hz), 5.74(1H,s), 6.34(1H,dt,J=16Hz,J=6Hz), 7.01(1H,d,J=16Hz), 7.14–7.63(7H,m), 7.88–7.91(1H,m), 8.29(1H,s) |

TABLE 1-continued (I)

$$\text{structure: phenyl ring with CH=NOR substituent, linked via O to a pyrimidine ring bearing two OCH}_3 \text{ groups}$$

| Compound No. | R | M.P. (°C.) | Preparation process | NMR spectrum |
|---|---|---|---|---|
| 33 | —CH₂CH=CH—(2,6-difluorophenyl) | 89–90 | B | (CDCl₃) δ 3.77(6H,s), 4.81(2H,d,J=6Hz), 5.73(1H,s), 6.66–6.68(2H,m), 6.82–6.88(2H,m), 7.07–7.41(4H,m), 7.88–7.91(1H,m), 8.29(1H,s) |
| 34 | —CH₂CH=CH—(2-methylphenyl) | 80–81 | B | (CDCl₃) δ 2.23(3H,s), 3.76(6H,s), 4.77(2H,d,J=6Hz), 5.74(1H,s), 6.33(1H,dt,J=16Hz,J=6Hz), 6.59(1H,d,J=16Hz), 6.98–7.40(7H,m), 7.87–7.91(1H,m), 8.28(1H,s) |
| 35 | —CH₂CH=CH—(4-CF₃-phenyl) | 81.5–82.5 | B | (CDCl₃) δ 3.78(6H,s), 4.80(2H,d,J=6Hz), 5.74(1H,s), 6.44(1H,dt,J=16Hz,J=6Hz), 6.59(1H,d,J=16Hz), 7.14–7.57(7H,m), 7.86–7.90(1H,m), 8.29(1H,s) |
| 36 | —CH₂CH=CH—(4-methylphenyl) | Oily | B | (CDCl₃) δ 2.32(3H,s), 3.77(6H,s), 4.77(2H,d,J=6Hz), 5.74(1H,s), 6.31(1H,dt,J=16Hz,J=6Hz), 6.60(1H,d,J=16Hz), 7.08–7.40(7H,m), 7.88–7.9(1H,m), 8.28(1H,s) |
| 37 | —CH₂CH=CH—(4-ethylphenyl) | Oily | B | (CDCl₃) δ 1.22(3H,t,J=7Hz), 2.62(2H,q,J=7Hz), 3.77(6H,s), 4.77(2H,d,J=6Hz), 5.74(1H,s), 6.30(1H,dt,J=16Hz,J=6Hz), 6.60(1H,d,J=16Hz), 7.10–7.40(7H,m), 7.87–7.91(1H,m), 8.27(1H,s) |
| 38 | —CH₂CH=CH—(2-methoxyphenyl) | Oily | B | (CDCl₃) δ 3.76(6H,s), 3.78(3H,s), 4.77(2H,d,J=6Hz), 5.74(1H,s), 6.34(1H,dt,J=16Hz,J=6Hz), 6.59(1H,d,J=16Hz), 6.75–7.40(7H,m), 7.88–7.91(1H,m), 8.28(1H,s) |
| 39 | —CH₂CH=CH—(3-methylphenyl) | Oily | B | (CDCl₃) δ 2.33(3H,s), 3.76(6H,s), 4.79(2H,d,J=6Hz), 5.73(1H,s), 6.23(1H,dt,J=16Hz,J=6Hz), 6.84(1H,d,J=16Hz), 7.11–7.44(7H,m), 7.89–7.92(1H,m), 8.28(1H,s) |
| 40 | —CH₂CH=CH—(2-bromophenyl) | Oily | B | (CDCl₃) δ 3.78(6H,s), 4.80–4.83(2H,m), 5.74(1H,s), 6.25–6.38(1H,m), 6.95–7.57(8H,m), 7.89–7.92(1H,m), 8.29–8.30(1H,m) |
| 41 | —CH₂CH=CH—(2,3-dichlorophenyl) | Oily | B | (CDCl₃) δ 3.78(6H,s), 4.57–4.83(2H,m), 5.74(1H,s), 6.20–6.47(1H,m), 6.86–7.56(7H,m), 7.87–7.91(1H,m), 8.21–8.30(1H,m) |

TABLE 1-continued

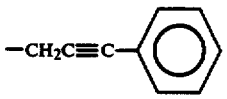

| Compound No. | R | M.P. (°C.) | Preparation process | NMR spectrum |
|---|---|---|---|---|
| 42 | —CH$_2$C≡C—⌬ | Oily | A | (CDCl$_3$) δ 3.77(6H,s), 4.90(2H,s), 5.70(1H,s), 7.00–7.60(8H,m), 7.90–8.00(1H,m), 8.27(1H,s) |

[FORMULATION EXAMPLES AND TESTS]

Formulation examples and herbicidal activity tests of certain herbicide and herbicidal compositions according to the invention will next be described.

FORMULATION EXAMPLE 1

Wettable powder

A wettable powder was obtained by thoroughly grinding and mixing 20 parts by weight of Compound No. 9 of the invention, 2 parts by weight of "Neopelex" (trade mark, product of Kao Corporation; sodium dodecyl benzene sulfonate), 1 part by weight of "Neugen EA80" (trade name, product of Daiichi Kogyo Seiyaku Industries, Ltd.; polyoxyethylene nonylphenyl ether), 5 parts by weight of white carbon and 72 parts by weight of diatomaceous earth.

FORMULATION EXAMPLE 2

Wettable powder

A wettable powder was obtained by thoroughly grinding and mixing 20 parts by weight of Compound No. 7 of the invention, 2 parts by weight of sodium alkylbenzenesulfonate, 1 part by weight of polyoxyethylene alkylphenyl ether and 77 parts by weight of "Zeaklite" (trade name of silica supplied from Zeaklite Kogyo Industries, Ltd.).

FORMULATION EXAMPLE 3

Wettable powder

A wettable powder was obtained by thoroughly grinding and mixing 50 parts by weight of Compound No. 27 of the invention, 5 parts by weight of white carbon, 6 parts by weight of ammonium polyoxyethylene alkylphenyl ether sulfate, 2 parts by weight of sodium lignine sulfonate and 37 parts by weight of diatomaceous earth in a Jet-O-Miser.

FORMULATION EXAMPLE 4

Flowable formulation

A flowable formulation was obtained by adding 76.7 parts by weight of water to the mixture of 20 parts by weight of Compound No. 39 of the invention, 2 parts by weight of sodium lignine sulfonate, 0.3 part by weight of xanthan gum and 1 part by weight of polyoxyethylene alkylaryl ether, mixing them and then finely grinding the resultant mixture in a sand grinder.

FORMULATION EXAMPLE 5

Flowable formulation

A flowable formulation was obtained by wet grinding and mixing 30 parts by weight of Compound No. 44 of the invention and a solution of 10 parts by weight of "Sun Ekisu P252" (trade name, product of Sanyo-Kokusaku Pulp Co., Ltd.; sodium lignine sulfonate) in 50 parts by weight of water and then adding and mixing a solution of 0.2 part by weight of "Kelzan S" (trade name, product of Kelco Corp.; xanthan gum) in 9.6 parts by weight of water and 0.2 part by weight of "Deltop" (trade mark, product of Takeda Chemical Industries, Ltd.; organic iodine antiseptic).

FORMULATION EXAMPLE 6

Powder

A powder was obtained by thoroughly grinding and mixing 1 part by weight of Compound No. 9 of the invention, 0.5 part by weight of "Emulgen 910" (trade name, product of Kao Corporation; polyoxyethylene nonylphenyl ether) and 98.5 parts by weight of kaolin clay.

FORMULATION EXAMPLE 7

Powder

A powder was obtained by grinding and mixing 3 parts by weight of Compound No. 7 of the invention, 3 parts by weight of sodium lignine sulfonate, 2 parts by weight of polyoxyethylene alkylaryl ether and 92 parts by weight of clay.

FORMULATION EXAMPLE 8

Dry flowable formulation

A dry flowable formulation was obtained by mixing 60 parts by weight of Compound No. 28 of the invention, which had been finely ground, 5 parts by weight of sodium alkyl benzene sulfonate, and 35 parts by weight of polypropylene glycol polyethylene glycol ether.

FORMULATION EXAMPLE 9

Granule

One part by weight of Compound No. 14 of the invention, which had been finely ground, 2 parts by weight of "Neopelex" (trade mark; described above), 2 parts by weight of "Sun Ekisu P252" (trade name; described above), 70 parts by weight of bentonite and 23 parts by weight of talc were thoroughly mixed. A suitable amount of water was added to the resultant mixture to wet the same, followed by extrusion of the mass through a small injection molding machine into pellets. After the pellets were dried at 30°-60° C. in air and then crushed into granules, the granules were classified by a sifting machine to collect granules of 0.3-2 mm.

FORMULATION EXAMPLE 10

Granule

One part by weight of Compound No. 7 of the invention, which had been finely ground, 2 parts by weight of "Gosenol GL-05s" (trade name, product of The Nippon Synthetic Chemical Industry Co., Ltd.; PVA), 2 parts by weight of "Sun Ekisu P-252" (trade name; described above) and 95 parts by weight of clay were thoroughly mixed. A suitable amount of water was added to the resultant mixture to wet the same, followed by extrusion of the mass through a small injection molding machine into pellets. After the pellets were dried at 60°-90° C. in air and then crushed into granules, the granules were classified by a sifting machine to collect granules of 0.3-1 mm.

FORMULATION EXAMPLE 11

Emulsion

Ten parts by weight of Compound No. 9 of the invention, 10 parts by weight of "Sorpole 800A" (trade name, product of Toho Chemical Industries Co., Ltd.; a non-ionic/anionic surfactant mixture) and 80 parts by weight of o-xylene were mixed into an emulsion.

FORMULATION EXAMPLE 12

Emulsion

Ten parts by weight of Compound No. 27 of the invention, 10 parts by weight of "Sorpole 800A" (trade name; described above) and 80 parts by weight of o-xylene were mixed into an emulsion.

FORMULATION EXAMPLE 13

Wettable powder

A wettable powder was obtained by thoroughly grinding and mixing 20 parts by weight of Compound No. 9, 10 parts by weight of diuron, 2 parts by weight of "Neopelex" (trade mark; described above), 2 parts by weight of "Neugen EA" (trade name; described above), 5 parts by weight of white carbon and 61 parts by weight of diatomaceous earth.

FORMULATION EXAMPLE 14

Powder

A powder was obtained by thoroughly grinding and mixing 1 part by weight of Compound No. 7, 1 part by weight of linuron, 0.5 part by weight of "Emulgen 910" (trade name; described above) an 97.5 parts by weight of kaolin clay.

FORMULATION EXAMPLE 15

Granule

Five parts by weight of Compound No. 15, which had been finely ground, 5 parts by weight of bentazon, 2 parts by weight of "Neopelex" (trade mark; described above), 2 parts by weight of "Sun Ekisu P252" (trade name; described above), 60 parts by weight of bentonite and 26 parts by weight of talc were thoroughly mixed. A suitable amount of water was added to the resultant mixture to wet the same, followed by extrusion of the mass through a small injection molding machine into granules. After the granules were dried at 30°-60° C. in air, they were classified by a sifting machine to collect granules of 0.3-2 mm.

FORMULATION EXAMPLE 16

Emulsion

Ten parts by weight of Compound No. 9, 10 parts by weight of diuron, 10 parts by weight of "Sorpole 800A" (trade name; described above) and 70 parts by weight of o-xylene were mixed into an emulsion.

FORMULATION EXAMPLE 17

Flowable formulation

A flowable formulation was obtained by wet grinding and mixing 10 parts by weight of Compound No. 7, 10 parts by weight of linuron and a solution of 10 parts by weight of "Sun Ekisu P252" (trade name; described above) in 60 parts by weight of water and then adding and mixing a solution of 0.2 part by weight of "Kelzan S" (trade name; described above) in 9.6 parts by weight of water and 0.2 part by weight of "Deltop" (trade mark; described above).

FORMULATION EXAMPLE 18

Emulsion

Ten parts by weight of Compound No. 9 of the invention, 10 parts by weight of atrazine, 10 parts by weight of "Sorpole 800A" (trade name; described above) and 80 parts by weight of o-xylene were mixed into an emulsion.

FORMULATION EXAMPLE 19

Emulsion

Ten parts by weight of Compound No. 24 of the invention, 10 parts by weight of cyanazine, 10 parts by weight of "Sorpole 800A" (trade name; described above) and 80 parts by weight of o-xylene were mixed into an emulsion.

FORMULATION EXAMPLE 20

Emulsion

Ten parts by weight of Compound No. 9, 10 parts by weight of alachlor, 10 parts by weight of "Sorpole 800A" (trade name; described above) and 70 parts by weight of o-xylene were mixed into an emulsion.

FORMULATION EXAMPLE 21

Emulsion

Ten parts by weight of Compound No. 7, 10 parts by weight of fluometuron, 10 parts by weight of "Sorpole 800A" (trade name; described above) and 70 parts by weight of o-xylene were mixed into an emulsion.

FORMULATION EXAMPLE 22

Emulsion

Ten parts by weight of Compound No. 9, 10 parts by weight of naptalam, 10 parts by weight of "Sorpole 800A" (trade name; described above) and 70 parts by weight of o-xylene were mixed into an emulsion.

FORMULATION EXAMPLE 23

Emulsion

Ten parts by weight of Compound No. 9, 10 parts by weight of linuron, 10 parts by weight of "Sorpole 800A" (trade name; described above) and 70 parts by weight of o-xylene were mixed into an emulsion.

FORMULATION EXAMPLE 24

Wettable powder

A wettable powder was obtained by thoroughly grinding and mixing 20 parts by weight of Compound No. 9, 10 parts by weight of linuron, 2 parts by weight of "Neopelex" (trade mark; described above), 2 parts by weight of "Neugen EA" (trade name; described above), 5 parts by weight of white carbon and 61 parts by weight of diatomaceous earth.

FORMULATION EXAMPLE 25

Wettable powder

A wettable powder was obtained by thoroughly grinding and mixing 20 parts by weight of Compound No. 9, 10 parts by weight of atrazine, 2 parts by weight of "Neopelex" (trade mark; described above), 2 parts by weight of "Neugen EA" (trade name; described above), 5 parts by weight of white carbon and 61 parts by weight of diatomaceous earth.

FORMULATION EXAMPLE 26

Wettable powder

A wettable powder was obtained by thoroughly grinding and mixing 20 parts by weight of Compound No. 9, 10 parts by weight of metolachlor, 2 parts by weight of "Neopelex" (trade mark; described above), 2 parts by weight of "Neugen EA" (trade name; described above), 5 parts by weight of white carbon and 61 parts by weight of diatomaceous earth.

FORMULATION EXAMPLE 27

Wettable powder

A wettable powder was obtained by thoroughly grinding and mixing 20 parts by weight of Compound No. 9, 10 parts by weight of bentazon, 2 parts by weight of "Neopelex" (trade mark; described above), 2 parts by weight of "Neugen EA" (trade name; described above), 5 parts by weight of white carbon and 61 parts by weight of diatomaceous earth.

FORMULATION EXAMPLE 28

Powder

A powder was obtained by thoroughly grinding and mixing 1 part by weight of Compound No. 7, 5 parts by weight of propanil, 0.5 part by weight of "Emulgen 910" (trade name; described above) an 93.5 parts by weight of kaolin clay.

FORMULATION EXAMPLE 29

Granule

Five parts by weight of Compound No. 15, which had been finely ground, 10 parts by weight of propanil, 2 parts by weight of "Neopelex" (trade name; described above), 2 parts by weight of "Sun Ekisu P252" (trade name; described above), 55 parts by weight of bentonite and 26 parts by weight of talc were thoroughly mixed. A suitable amount of water was added to the resultant mixture to wet the same, followed by extrusion of the mass through a small injection molding machine into granules. After the granules were dried at 30°-60° C. in air, they were classified by a sifting machine to collect granules of 0.3-2 mm.

FORMULATION EXAMPLE 30

Flowable formulation

A flowable formulation was obtained by wet grinding and mixing 10 parts by weight of Compound No. 7, 10 parts by weight of diuron and a solution of 10 parts by weight of "Sun Ekisu P252" (trade name; described above) in 60 parts by weight of water and then adding and mixing a solution of 0.2 part by weight of "Kelzan S" (trade name; described above) in 9.6 parts by weight of water and 0.2 part by weight of "Deltop" (trade mark; described above).

FORMULATION EXAMPLE 31

Flowable formulation

A flowable formulation was obtained by wet grinding and mixing 10 parts by weight of Compound No. 7, 10 parts by weight of atrazine and a solution of 10 parts by weight of "Sun Ekisu P252" (trade name; described above) in 60 parts by weight of water and then adding and mixing a solution of 0.2 part by weight of "Kelzan S" (trade name; described above) in 9.6 parts by weight of water and 0.2 part by weight of "Deltop" (trade mark; described above).

FORMULATION EXAMPLE 32

Flowable formulation

A flowable formulation was obtained by wet grinding and mixing 10 parts by weight of Compound No. 7, 10 parts by weight of alachlor and a solution of 10 parts by weight of "Sun Ekisu P252" (trade name; described above) in 60 parts by weight of water and then adding and mixing a solution of 0.2 part by weight of "Kelzan S" (trade name; described above) in 9.6 parts by weight of water and 0.2 part by weight of "Deltop" (trade mark; described above).

FORMULATION EXAMPLE 33

Dry flowable formulation

A dry flowable formulation was obtained by mixing 30 parts by weight of Compound No. 28 of the invention, which had been finely ground, 30 parts by weight of linuron, 5 parts by weight of sodium alkyl benzene sulfonate, and 35 parts by weight of polypropylene glycol polyethylene glycol ether.

Test 1:

ALS (Acetolactate Syntase) Enzyme Assay

To determine the selectivity in enzyme level between crops and weeds, an ALS enzyme assay was conducted using pea as a representative of broadleaf crops and barnyardgrass as a representative of narrowleaf weeds.

After seeds of pea and barnyardgrass were allowed to germinate at 25° C. for 8-14 days in a dark place, partially-purified suspensions (Suspensions A) of acetolactate syntase were separately obtained from seedlings in accordance with the method described in the literature, Plant Physiology, 75, 827-831.

In a test tube, 0.5 mg of one of test compounds was weighed, followed by the addition of 0.15 ml of a 20 mM $K_2HPO_4$ solution and 0.25 ml of a reaction substrate medium which consisted of 40 mM of $K_2HPO_4$, 40 mM of sodium pyruvate, 1 mM of TPP, 1 mM of MgCl$_2$ and 20 μM of FAD so that 0.4 ml of a reaction solution (Solution B) was prepared. Added to 0.4 ml of Solution B was 0.1 ml of Suspension A. After the resultant mixture was shaken for 1 hour in a thermostat water bath controlled at 30° C., 50 μl of 6N sulfuric acid were added to terminate the reaction.

Next, the reaction-terminated liquid mixture was transferred into a thermostat water bath controlled at 60° C. and was heated for 15 minutes. Thereafter, 0.5 ml of a 0.5% creatine solution and 0.5 ml of a 5% alkaline α-naphthol solution were added, and the resultant mixture was maintained at 60° C. for 15 minutes. As a result, the test solution developed a pink-red color. After the above operation, the absorbance of the test solution at 525 nm was measured by a spectrophotometer (Absorbance ① of Test Compound).

On the other hand, the absorbance (Absorbance ② of Blank) of a solution obtained by subjecting a portion of Solution B, said portion being free of the test compound, to the above operation and the absorbance (Absorbance ③ of of sulfuric acid terminated) of another solution obtained by subjecting another portion of Solution B, said portion containing 50 μl of 6N sulfuric acid as a test compound, were measured at the same time. Based on the values of the respective measurements, the enzyme assay at 1,000 ppm (0.5 mg/0.5 ml) of each compound was determined. The results are shown in Table 2.

$$\text{Inhibitory activity} = \left(1 - \frac{①-③}{②-③}\right) \times 100$$

Incidentally, Comparative Compounds A and B mean the following compounds (this also applies to Test 2 and Test 3).

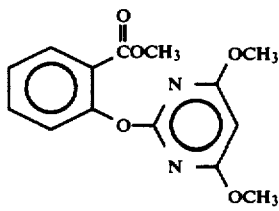

A

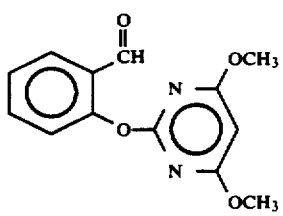

B (These compounds are both disclosed in Japanese Patent Laid-Open No. 174059/1987.)

The results of this test indicates that the compounds of the invention show strong inhibition in enzyme level against gramineous weeds such as barnyardgrass but show no inhibition to broadleaf crops such as pea, in other words, have distinct selectivity.

TABLE 2

Results of Enzyme Test

| Compound No. | Inhibitory activity (%) Barnyardgrass | Pea |
|---|---|---|
| 1 | 58 | 3 |
| 2 | 21 | 0 |
| 3 | 22 | 0 |
| 4 | 59 | 0 |
| 5 | 64 | 0 |
| 6 | 17 | 0 |
| 7 | 84 | 0 |
| 8 | 41 | 0 |
| 9 | 95 | 11 |
| 10 | 55 | 0 |
| 11 | 43 | 0 |
| 12 | 39 | 0 |
| 13 | 85 | 0 |
| 14 | 56 | 0 |
| 15 | 23 | 0 |
| 16 | 15 | 0 |
| 17 | 15 | 0 |
| 18 | 14 | 0 |
| 19 | 16 | 0 |
| 20 | 58 | 0 |
| 21 | 26 | 0 |
| 22 | 35 | 0 |
| 23 | 35 | 0 |
| 24 | 36 | 0 |
| 25 | 39 | 0 |
| 26 | 89 | 8 |
| 27 | 100 | 12 |
| 28 | 91 | 8 |
| 29 | 98 | 11 |
| 30 | 97 | 6 |
| 31 | 90 | 0 |
| 32 | 91 | 0 |
| 33 | 91 | 0 |
| 34 | 91 | 0 |
| 35 | 89 | 10 |
| 36 | 92 | 0 |
| 37 | 93 | 0 |
| 38 | 91 | 0 |
| 39 | 92 | 0 |
| 40 | 94 | 0 |
| 41 | 89 | 0 |
| 42 | 93 | 0 |
| Comparative Compound | | |
| A | 73 | 72 |
| B | 98 | 92 |

Test 2:
Upland Soil Application Test

Resin-made 1/2500-are pots were filled with the soil of an upland field. After they were fertilized, soybean, peanut and cotton were seeded and 2-3 cm soil covering was applied. Seeds of redroot pigweed, common lambsquarters, barnyardgrass, green foxtail, large crabgrass, foxtail meadow and johnsongrass had been uniformly mixed with the soil. They were allowed to germinate in a green house. One day later (before emergence of weeds), a wettable powder prepared from a predetermined amount of each test compound in a similar manner to the method described in Formulation Example 1 was diluted with water and then sprayed evenly at an application rate equal to 10 l per are onto the surface of the soil by means of a pressure-operated ULV (ultra low volume) sprayer. Influence to the crops and weeds were observed 30 days later. The results are shown in Table 3, in which the degree of damages of each test plant and the degree of injury to each crop were determined by comparing the air-dried weights of the test plant and crop with those of the corresponding plant and crop in untreated pots and are shown in accordance with the following standard:

| Rank | Growth rate (%) expressed in terms of the percentage of dried weight relative to the dried weight of untreated group | |
|---|---|---|
| 5 | 0–5 | (Death) |
| 4 | 6–10 | (Severe damages) |
| 3 | 11–40 | (Medium damages) |
| 2 | 41–70 | (Small damages) |
| 1 | 71–90 | (Slight damages) |
| 0 | 91–100 | (No damages) |

The results of the present test indicate that the compounds of the invention represented by the formula [I] exhibit high herbicidal effects against gramineous weeds including some broadleaf weeds and perennial weeds in soil treatment and can be used extremely safely for broadleaf crops such as soybean, cotton and peanut.

squarters, foxtail meadow, johnsongrass, barnyardgrass, green foxtail, large crabgrass, soybean, peanut and cotton were separately seeded and were allowed to germinate in a green house. When each plant grew to the stage of 2–3 leaves, an emulsion formulated from a predetermined amount of each test compound in a similar manner to the method described in Formulation Example 11 was diluted with water to a predetermined dilution rate and then sprayed at an application rate equal to 5 l per are onto the foliage of each plant by means of a pressure-operated ULV (ultra low volume) sprayer. Influence to the crops and weeds were observed on the 30th day after the spray of the herbicides. The results are shown in Table 4 in which the degree of damages of each test plant and the degree of injury to each crop are shown in a similar manner to Test 2.

The results of the present test indicate that the compounds of the invention represented by the formula [I] exhibit high herbicidal effects against gramineous weeds including some broadleaf weeds and perennial

TABLE 3

Results of Upland Soil Application Test

| Compound No. | Application rate of active ingredient (g ai/a) | Herbicidal effects | | | | | | | Injury | | |
|---|---|---|---|---|---|---|---|---|---|---|---|
| | | Redroot pigweed | Common lambsquarters | Barnyard-grass | Green foxtail | Large crabgrass | Foxtail meadow | Johnson-grass | Soy-bean | Cotton | Peanut |
| 1 | 30 | 5 | 4 | 5 | 5 | 4 | 5 | 5 | 0 | 0 | 0 |
| 2 | 30 | 4 | 4 | 5 | 5 | 5 | 5 | 5 | 0 | 0 | 0 |
| 3 | 30 | 3 | 3 | 3 | 4 | 3 | 3 | 4 | 0 | 0 | 0 |
| 4 | 30 | 4 | 3 | 5 | 5 | 4 | 5 | 5 | 0 | 0 | 0 |
| 5 | 30 | 4 | 4 | 5 | 5 | 5 | 5 | 5 | 0 | 0 | 0 |
| 6 | 30 | 3 | 4 | 4 | 5 | 4 | 5 | 5 | 0 | 0 | 0 |
| 7 | 30 | 4 | 4 | 5 | 5 | 5 | 5 | 5 | 0 | 0 | 0 |
| 8 | 30 | 5 | 4 | 4 | 5 | 4 | 5 | 5 | 0 | 0 | 0 |
| 9 | 30 | 5 | 4 | 5 | 5 | 5 | 5 | 5 | 0 | 0 | 0 |
| 10 | 30 | 3 | 3 | 3 | 4 | 3 | 4 | 4 | 0 | 0 | 0 |
| 11 | 30 | 5 | 4 | 5 | 5 | 5 | 5 | 5 | 0 | 0 | 0 |
| 12 | 30 | 3 | 3 | 4 | 4 | 4 | 4 | 4 | 0 | 0 | 0 |
| 13 | 30 | 5 | 4 | 5 | 5 | 5 | 5 | 5 | 0 | 0 | 0 |
| 14 | 30 | 4 | 4 | 5 | 5 | 5 | 5 | 5 | 0 | 0 | 0 |
| 15 | 30 | 4 | 4 | 5 | 5 | 4 | 5 | 5 | 0 | 0 | 0 |
| 16 | 30 | 3 | 3 | 3 | 3 | 4 | 3 | 3 | 0 | 0 | 0 |
| 17 | 30 | 3 | 4 | 3 | 3 | 3 | 3 | 3 | 0 | 0 | 0 |
| 18 | 30 | 3 | 4 | 4 | 4 | 3 | 3 | 3 | 0 | 0 | 0 |
| 19 | 30 | 3 | 4 | 4 | 4 | 3 | 4 | 3 | 0 | 0 | 0 |
| 20 | 30 | 5 | 4 | 3 | 5 | 5 | 5 | 5 | 0 | 0 | 0 |
| 21 | 30 | 3 | 3 | 3 | 4 | 4 | 3 | 4 | 0 | 0 | 0 |
| 22 | 30 | 3 | 3 | 3 | 4 | 3 | 4 | 4 | 0 | 0 | 0 |
| 23 | 30 | 3 | 4 | 3 | 3 | 3 | 3 | 4 | 0 | 0 | 0 |
| 24 | 30 | 4 | 4 | 4 | 5 | 4 | 5 | 5 | 0 | 0 | 0 |
| 25 | 30 | 4 | 4 | 4 | 5 | 5 | 5 | 5 | 0 | 0 | 0 |
| 26 | 30 | 5 | 4 | 5 | 5 | 5 | 4 | 5 | 0 | 0 | 0 |
| 27 | 30 | 5 | 4 | 4 | 5 | 5 | 5 | 5 | 0 | 0 | 0 |
| 28 | 30 | 4 | 4 | 4 | 5 | 4 | 5 | 5 | 0 | 0 | 0 |
| 29 | 30 | 5 | 4 | 5 | 4 | 5 | 4 | 5 | 0 | 0 | 0 |
| 30 | 30 | 5 | 4 | 5 | 5 | 5 | 5 | 5 | 0 | 0 | 0 |
| 31 | 30 | 3 | 3 | 4 | 4 | 4 | 4 | 5 | 0 | 0 | 0 |
| 32 | 30 | 5 | 4 | 5 | 5 | 5 | 5 | 5 | 0 | 0 | 0 |
| 33 | 30 | 4 | 4 | 5 | 5 | 5 | 5 | 5 | 0 | 0 | 0 |
| 34 | 30 | 4 | 4 | 5 | 5 | 4 | 5 | 5 | 0 | 0 | 0 |
| 35 | 30 | 4 | 5 | 5 | 5 | 5 | 5 | 5 | 0 | 0 | 0 |
| 36 | 30 | 4 | 4 | 5 | 5 | 5 | 5 | 5 | 0 | 0 | 0 |
| 37 | 30 | 4 | 4 | 4 | 5 | 5 | 5 | 5 | 0 | 0 | 0 |
| 38 | 30 | 4 | 4 | 5 | 5 | 5 | 4 | 5 | 0 | 0 | 0 |
| 39 | 30 | 5 | 4 | 4 | 5 | 5 | 5 | 5 | 0 | 0 | 0 |
| 40 | 30 | 5 | 4 | 5 | 4 | 4 | 5 | 4 | 0 | 0 | 0 |
| 41 | 30 | 5 | 4 | 5 | 4 | 5 | 4 | 4 | 0 | 0 | 0 |
| 42 | 30 | 3 | 4 | 5 | 5 | 4 | 5 | 5 | 0 | 0 | 0 |
| Comparative Compound A | 30 | 5 | 4 | 5 | 5 | 5 | 5 | 5 | 5 | 5 | 5 |
| Comparative Compound B | 30 | 3 | 3 | 4 | 4 | 4 | 4 | 4 | 5 | 5 | 5 |

Test 3:
Upland Foliar Application Test
Resin-made 1/10000-are pots were filled with the soil of an upland field. Redroot pigweed, common lambsquarters, foxtail meadow, johnsongrass, barnyardgrass, weeds in foliage application and can be used extremely safely for broadleaf crops such as soybean, cotton and peanut.

TABLE 4

| | | Results of Upland Foliar Application Test | | | | | | | | | |
|---|---|---|---|---|---|---|---|---|---|---|---|
| | Application rate | Herbicidal effects | | | | | | | Injury | | |
| Compound No. | of active ingredient (g ai/a) | Redroot pigweed | Common lambsquarters | Barnyardgrass | Green foxtail | Large crabgrass | Foxtail meadow | Johnsongrass | Soybean | Cotton | Peanut |
| 1 | 30 | 5 | 4 | 5 | 5 | 3 | 5 | 5 | 0 | 0 | 0 |
| 2 | 30 | 4 | 4 | 5 | 5 | 5 | 5 | 5 | 0 | 0 | 0 |
| 3 | 30 | 4 | 4 | 5 | 5 | 4 | 5 | 5 | 0 | 0 | 0 |
| 4 | 30 | 4 | 3 | 5 | 5 | 3 | 5 | 5 | 0 | 0 | 0 |
| 5 | 30 | 4 | 4 | 5 | 5 | 5 | 5 | 5 | 0 | 0 | 0 |
| 6 | 30 | 4 | 4 | 4 | 5 | 3 | 5 | 5 | 0 | 0 | 0 |
| 7 | 30 | 5 | 4 | 5 | 5 | 5 | 5 | 5 | 0 | 0 | 0 |
| 8 | 30 | 5 | 4 | 4 | 5 | 3 | 5 | 5 | 0 | 0 | 0 |
| 9 | 30 | 5 | 4 | 5 | 5 | 5 | 5 | 5 | 0 | 0 | 0 |
| 10 | 30 | 5 | 4 | 5 | 4 | 5 | 4 | 5 | 0 | 0 | 0 |
| 11 | 30 | 5 | 4 | 5 | 5 | 5 | 5 | 5 | 0 | 0 | 0 |
| 12 | 30 | 3 | 3 | 4 | 4 | 4 | 4 | 5 | 0 | 0 | 0 |
| 13 | 30 | 5 | 4 | 5 | 5 | 5 | 5 | 5 | 0 | 0 | 0 |
| 14 | 30 | 4 | 4 | 5 | 5 | 5 | 5 | 5 | 0 | 0 | 0 |
| 15 | 30 | 5 | 5 | 5 | 5 | 4 | 4 | 5 | 0 | 0 | 0 |
| 16 | 30 | 4 | 3 | 3 | 5 | 3 | 3 | 5 | 0 | 0 | 0 |
| 17 | 30 | 4 | 4 | 3 | 5 | 3 | 3 | 5 | 0 | 0 | 0 |
| 18 | 30 | 4 | 3 | 4 | 5 | 3 | 4 | 5 | 0 | 0 | 0 |
| 19 | 30 | 4 | 4 | 3 | 5 | 3 | 4 | 5 | 0 | 0 | 0 |
| 20 | 30 | 5 | 4 | 5 | 5 | 5 | 5 | 5 | 0 | 0 | 0 |
| 21 | 30 | 3 | 3 | 3 | 4 | 4 | 3 | 5 | 0 | 0 | 0 |
| 22 | 30 | 5 | 4 | 5 | 5 | 5 | 5 | 5 | 0 | 0 | 0 |
| 23 | 30 | 3 | 3 | 3 | 4 | 3 | 4 | 5 | 0 | 0 | 0 |
| 24 | 30 | 3 | 3 | 4 | 4 | 4 | 4 | 5 | 1 | 1 | 0 |
| 25 | 30 | 4 | 4 | 4 | 5 | 5 | 5 | 5 | 0 | 0 | 0 |
| 26 | 30 | 4 | 4 | 5 | 5 | 5 | 4 | 5 | 0 | 0 | 0 |
| 27 | 30 | 5 | 4 | 4 | 5 | 5 | 5 | 5 | 0 | 0 | 0 |
| 28 | 30 | 4 | 4 | 5 | 4 | 4 | 5 | 5 | 0 | 0 | 0 |
| 29 | 30 | 5 | 4 | 5 | 4 | 4 | 4 | 5 | 0 | 0 | 0 |
| 30 | 30 | 5 | 4 | 5 | 5 | 5 | 5 | 5 | 0 | 0 | 0 |
| 31 | 30 | 3 | 4 | 4 | 4 | 4 | 4 | 5 | 0 | 0 | 0 |
| 32 | 30 | 5 | 4 | 5 | 5 | 5 | 5 | 5 | 0 | 0 | 0 |
| 33 | 30 | 4 | 4 | 5 | 5 | 5 | 5 | 5 | 0 | 0 | 0 |
| 34 | 30 | 4 | 4 | 5 | 5 | 4 | 5 | 5 | 0 | 0 | 0 |
| 35 | 30 | 4 | 4 | 5 | 5 | 5 | 5 | 5 | 0 | 0 | 0 |
| 36 | 30 | 4 | 4 | 5 | 5 | 5 | 5 | 5 | 0 | 0 | 0 |
| 37 | 30 | 4 | 4 | 4 | 5 | 5 | 5 | 5 | 0 | 0 | 0 |
| 38 | 30 | 4 | 4 | 5 | 5 | 5 | 4 | 5 | 0 | 0 | 0 |
| 39 | 30 | 5 | 4 | 5 | 5 | 5 | 5 | 5 | 0 | 0 | 0 |
| 40 | 30 | 5 | 4 | 5 | 4 | 4 | 5 | 5 | 0 | 0 | 0 |
| 41 | 30 | 5 | 4 | 5 | 4 | 5 | 4 | 5 | 0 | 0 | 0 |
| 42 | 30 | 5 | 4 | 5 | 5 | 3 | 5 | 5 | 0 | 0 | 0 |
| Comparative Compound A | 30 | 5 | 4 | 5 | 5 | 5 | 5 | 5 | 5 | 5 | 5 |
| Comparative Compound B | 30 | 3 | 3 | 4 | 4 | 4 | 4 | 4 | 5 | 5 | 5 |

Test 4:

Treatment of Soil under Submerged Condition (Pre-emergence Treatment)

1/5000-are Wagner pots were filled with soil. Seeds or tubers of barnyardgrass, Monochoria vaginalis, bulrush, Sagittaria pygmaea, Cyperus seroylnus and Eleocharis kuroguwai were seeded or planted under submerged condition. Two pairs of rice seedlings (2-3 leaf stage), which had been reared in advance, were transplanted to each pot and were allowed to germinate in a green house. Each pair consisted of two rice seedlings. One day later (before emergence of weeds), each pot was treated with a granule which had been prepared by processing a predetermined amount of the test composition in accordance with a similar method to the method described in Formulation Example 9. The state of emergence of weeds and the state of injury of rice were observed 30 days later. The results are summarized in Table 5.

In the table, the degrees of damages of the test plants and the degrees of injury of rice are shown in a similar manner to Example 2.

TABLE 5

| | Treatment Test on Soil under Submerged Condition (Pre-Emergence) | | | | |
|---|---|---|---|---|---|
| Compound No. | Application rate of active ingredient (g ai/a) | Herbicidal effects | | | Injury |
| | | Barnyardgrass | Bulrush | Sagittaria Pygmaea | Rice |
| 1 | 30 | 2 | 2 | 3 | 0 |
| 2 | 30 | 5 | 4 | 4 | 1 |
| 3 | 30 | 4 | 4 | 5 | 0 |
| 4 | 30 | 4 | 4 | 4 | 0 |
| 5 | 30 | 4 | 4 | 5 | 0 |
| 6 | 30 | 4 | 4 | 4 | 0 |
| 7 | 30 | 5 | 4 | 5 | 1 |
| 8 | 30 | 4 | 4 | 4 | 1 |

TABLE 5-continued

Treatment Test on Soil under Submerged Condition (Pre-Emergence)

| Compound No. | Application rate of active ingredient (g ai/a) | Herbicidal effects | | | Injury Rice |
|---|---|---|---|---|---|
| | | Barnyardgrass | Bulrush | Sagittaria Pygmaea | |
| 9 | 30 | 5 | 4 | 5 | 1 |
| 10 | 30 | 5 | 4 | 4 | 1 |
| 11 | 30 | 4 | 3 | 4 | 1 |
| 12 | 30 | 4 | 4 | 4 | 1 |
| 13 | 30 | 4 | 5 | 4 | 1 |
| 14 | 30 | 5 | 3 | 5 | 0 |
| 15 | 30 | 4 | 1 | 3 | 1 |
| 16 | 30 | 4 | 3 | 4 | 0 |
| 17 | 30 | 4 | 4 | 3 | 0 |
| 18 | 30 | 4 | 2 | 4 | 0 |
| 19 | 30 | 4 | 4 | 4 | 0 |
| 20 | 30 | 5 | 4 | 4 | 0 |
| 21 | 30 | 3 | 3 | 3 | 0 |
| 22 | 30 | 3 | 3 | 3 | 0 |
| 23 | 30 | 5 | 4 | 5 | 0 |
| 24 | 30 | 3 | 2 | 4 | 1 |
| 25 | 30 | 5 | 3 | 4 | 1 |
| 26 | 30 | 4 | 4 | 5 | 0 |
| 27 | 30 | 5 | 4 | 4 | 0 |
| 28 | 30 | 3 | 3 | 3 | 0 |
| 29 | 30 | 3 | 3 | 3 | 0 |
| 30 | 30 | 5 | 4 | 5 | 0 |
| 31 | 30 | 3 | 3 | 4 | 0 |
| 32 | 30 | 5 | 4 | 5 | 0 |
| 33 | 30 | 4 | 4 | 5 | 0 |
| 34 | 30 | 4 | 4 | 5 | 0 |
| 35 | 30 | 4 | 3 | 5 | 0 |
| 36 | 30 | 4 | 4 | 5 | 0 |
| 37 | 30 | 4 | 4 | 4 | 0 |
| 38 | 30 | 4 | 4 | 5 | 0 |
| 39 | 30 | 5 | 4 | 4 | 1 |
| 40 | 30 | 5 | 3 | 5 | 0 |
| 41 | 30 | 5 | 4 | 5 | 0 |
| 42 | 30 | 5 | 4 | 5 | 0 |
| Comparative Compound A | 30 | 5 | 5 | 4 | 5 |
| Comparative Compound B | 30 | 3 | 3 | 5 | 5 |

Test 5:

Treatment of Soil under Submerged Condition (Post-Emergence Treatment)

1/5000-are Wagner pots were filled with soil. Seeds or tubers of barnyardgrass, *Monochoria vaginalis*, bulrush, *Sagittaria pygmaea*, *Cyperus seroylnus* and *Eleocharis kuroguwai* were seeded or planted under submerged condition. Two pairs of rice seedlings (2-3 leaf stage), which had been reared in advance, were transplanted to each pot and were allowed to grow in a green house. Each pair consisted of two rice seedlings. When the barnyardgrass grew to two-leaf stage, each pot was treated with a granule which had been prepared by processing a predetermined amount of the test composition in accordance with a similar method to the method described in Formulation Example 9. The state of emergence of weeds and the state of injury of rice were observed 30 days later. The results are summarized in Table 6.

In the table, the degrees of damages of the test plants and the degrees of injury of the rice are shown in a similar manner to Example 2.

TABLE 6

Treatment Test on Soil under Submerged Condition (Post-Emergence)

| Compound No. | Application rate of active ingredient (g ai/a) | Herbicidal effects | | | Injury Rice |
|---|---|---|---|---|---|
| | | Barnyardgrass | Bulrush | *Sagittaria pygmaea* | |
| 1 | 30 | 4 | 5 | 3 | 0 |
| 2 | 30 | 5 | 5 | 5 | 0 |
| 3 | 30 | 3 | 3 | 3 | 0 |
| 4 | 30 | 5 | 4 | 3 | 0 |
| 5 | 30 | 5 | 5 | 5 | 0 |
| 6 | 30 | 4 | 4 | 3 | 0 |
| 7 | 30 | 5 | 5 | 3 | 0 |
| 8 | 30 | 5 | 5 | 5 | 1 |
| 9 | 30 | 5 | 5 | 5 | 0 |
| 10 | 30 | 5 | 5 | 5 | 1 |
| 11 | 30 | 5 | 4 | 4 | 0 |
| 12 | 30 | 5 | 5 | 3 | 0 |
| 13 | 30 | 5 | 4 | 3 | 0 |
| 14 | 30 | 5 | 5 | 4 | 1 |
| 15 | 30 | 5 | 4 | 3 | 1 |
| 16 | 30 | 4 | 4 | 3 | 0 |

TABLE 6-continued

Treatment Test on Soil under Submerged Condition (Post-Emergence)

| Compound No. | Application rate of active ingredient (g ai/a) | Herbicidal effects | | | Injury Rice |
|---|---|---|---|---|---|
| | | Barnyardgrass | Bulrush | Sagittaria pygmaea | |
| 17 | 30 | 3 | 4 | 3 | 0 |
| 18 | 30 | 3 | 4 | 4 | 0 |
| 19 | 30 | 4 | 4 | 3 | 0 |
| 20 | 30 | 5 | 4 | 4 | 0 |
| 21 | 30 | 3 | 3 | 3 | 0 |
| 22 | 30 | 5 | 4 | 3 | 0 |
| 23 | 30 | 5 | 4 | 5 | 0 |
| 24 | 30 | 5 | 5 | 4 | 1 |
| 25 | 30 | 4 | 5 | 3 | 1 |
| 26 | 30 | 5 | 4 | 4 | 0 |
| 27 | 30 | 5 | 4 | 4 | 0 |
| 28 | 30 | 5 | 4 | 4 | 0 |
| 29 | 30 | 5 | 4 | 4 | 1 |
| 30 | 30 | 5 | 4 | 4 | 0 |
| 31 | 30 | 5 | 4 | 4 | 0 |
| 32 | 30 | 5 | 4 | 4 | 1 |
| 33 | 30 | 5 | 5 | 4 | 1 |
| 34 | 30 | 5 | 4 | 3 | 1 |
| 35 | 30 | 5 | 4 | 3 | 0 |
| 36 | 30 | 5 | 5 | 4 | 1 |
| 37 | 30 | 5 | 5 | 4 | 1 |
| 38 | 30 | 5 | 5 | 4 | 1 |
| 39 | 30 | 5 | 4 | 4 | 0 |
| 40 | 30 | 5 | 4 | 4 | 1 |
| 41 | 30 | 5 | 4 | 4 | 0 |
| 42 | 30 | 5 | 4 | 5 | 0 |
| Comparative Compound A | 30 | 5 | 4 | 4 | 5 |
| Comparative Compound B | 30 | 5 | 5 | 4 | 5 |

Test 6:

Petri Dish Test

A filter paper was placed in each glass-made Petri dish having a diameter of 9 cm. A compound dissolved in acetone was added in a predetermined amount. The filter paper was then dried in air to remove acetone. Seeds of narrowleaf waterplantain were placed on the filter paper and 10 ml of water were poured into the Petri dish. The seeds were allowed to grow at 25° C. in a bright room. Fourteen days later, the state of growth of narrowleaf water-plantain was observed. The results are summarized in Table 7.

In the table, the degree of damages of the test plant was determined by comparing the state of growth of the plant with that of the plant in an untreated group and is shown in accordance with the following standard:

| Rank | Growth rate (%) | Degree of damages |
|---|---|---|
| 5 | 0–5 | (Death) |
| 4 | 6–10 | (Severe damages) |
| 3 | 11–40 | (Medium damages) |
| 2 | 41–70 | (Small damages) |
| 1 | 71–90 | (Slight damages) |
| 0 | 91–100 | (No damages) |

The results of Test 4 to Test 6 indicate that the compounds of the invention represented by the formula [I] exhibit high herbicidal effects against gramineous weeds including some broadleaf weeds and perennial weeds in soil treatment under submerged condition and can be used for rice under extremely low injury conditions.

TABLE 7

Results of Petri Dish Test

| Compound No. | $I_{80}$ (ppm) | Compound No. | $I_{80}$ (ppm) |
|---|---|---|---|
| 1 | 25 | 27 | 2 |
| 2 | 100 | 28 | 2 |
| 3 | 100 | 29 | 8 |
| 4 | 100 | 30 | 2 |
| 5 | 17 | 47 | 17 |
| 6 | 40 | 48 | 25 |
| 7 | 17 | 31 | 2 |
| 8 | 40 | 32 | 4 |
| 9 | 2 | 33 | 8 |
| 10 | 17 | 34 | 2 |
| 11 | 40 | 35 | 6 |
| 12 | 100 | 36 | 4 |
| 13 | 5 | 37 | 2 |
| 14 | 100 | 38 | 2 |
| 15 | 100 | 39 | 2 |
| 16 | 100 | 40 | 2 |
| 17 | 100 | 41 | 2 |
| 18 | 67 | 42 | 17 |
| 19 | 100 | | |
| 20 | 100 | | |
| 21 | 100 | | |
| 22 | 100 | | |
| 23 | 100 | | |
| 24 | 100 | | |
| 25 | 17 | | |
| 26 | 2 | | |
| Comparative Compound A | 1 | Comparative Compound B | 1 |

Test 7:

Upland Foliar Application Test by Mixed Formulations

Resin-made 1/10000-are pots were filled with the soil of an upland field. Redroot pigweed, morningglories, johnsongrass, barnyardgrass and green foxtail were separately seeded and were allowed to germinate in a green house. When each plant grew to the stage of 2–3 leaves, an emulsion formulated from predetermined amounts of two test compounds of different kinds in a similar manner to the method described in Formulation Example 16 was diluted with water to a predetermined dilution rate and then sprayed at an application rate equal to 5 l per are onto the foliage of each plant by means of a pressure-operated ULV (ultra low volume) sprayer. Influence to the weeds were observed on the 30th day after the spray of the herbicides. The results are shown in Table 8, In the table, each Ea means an actually measured value of herbicidal activities when two kinds of herbicides were mixed. Each Ec is an expected value for herbicidal activities, calculated in accordance with the below-described calculation formula proposed by Colby et al. [Colby, S. R., Weed 15, 20–22 (1967)]. Ea>Ec indicates the existence of synergistic action while Ea<Ec indicates the existence of antagonistic action.

$$100 - Ec = \frac{(100 - Ex) \times (100 - Ey)}{100}$$

Ec: Growth inhibition rate (%) expected when Ingredient I and Ingredient II are mixed.
Ex: Growth inhibition rate (%) when treated with Ingredient I alone.
Ey: Growth inhibition rate (%) when treated with Ingredient II alone.

TABLE 8

| Ingredient I (invention compound) | | Mixing Effects Ingredient II | | Herbicidal effects (%) | | | |
|---|---|---|---|---|---|---|---|
| | | | | Redrood pigweed | | Johnsongrass | |
| Compound No. | Application rate (kg/ha) | Name of ingredient | Application rate (kg/ha) | Ec | Ea | Ec | Ea |
| | 0 | atrazine | 0.8 | — | 40 | — | 10 |
| 3 | 1 | atrazine | 0 | — | 40 | — | 40 |
| | 1 | | 0.8 | 64 | 100 | 46 | 85 |
| 6 | 1 | | 0 | — | 50 | — | 30 |
| | 1 | | 0.8 | 70 | 100 | 37 | 70 |
| 7 | 0.3 | | 0 | — | 30 | — | 30 |
| | 0.3 | | 0.8 | 58 | 100 | 37 | 100 |
| 9 | 0.3 | | 0 | — | 50 | — | 40 |
| | 0.3 | | 0.8 | 70 | 100 | 46 | 100 |
| 10 | 1 | | 0 | — | 10 | — | 20 |
| | 1 | | 0.8 | 46 | 85 | 24 | 70 |
| 11 | 1 | | 0 | — | 30 | — | 0 |
| | 1 | | 0.8 | 58 | 100 | 10 | 50 |
| 13 | 1 | | 0 | — | 70 | — | 70 |
| | 1 | | 0.8 | 82 | 100 | 73 | 100 |
| 14 | 0.3 | | 0 | — | 85 | — | 30 |
| | 0.3 | | 0.8 | 91 | 100 | 37 | 85 |
| 15 | 1 | | 0 | — | 50 | — | 0 |
| | 1 | | 0.8 | 70 | 100 | 10 | 70 |
| 20 | 0.3 | | 0 | — | 30 | — | 0 |
| | 0.3 | | 0.8 | 58 | 100 | 10 | 80 |
| 24 | 0.3 | | 0 | — | 50 | — | 20 |
| | 0.3 | | 0.8 | 75 | 100 | 24 | 85 |
| 27 | 0.3 | | 0 | — | 50 | — | 30 |
| | 0.3 | | 0.8 | 70 | 100 | 37 | 100 |
| 28 | 0.3 | | 0 | — | 40 | — | 20 |
| | 0.3 | | 0.8 | 70 | 100 | 37 | 100 |
| 30 | 0.3 | | 0 | — | 40 | — | 20 |
| | 0.3 | | 0.8 | 64 | 100 | 28 | 100 |
| 32 | 1 | | 0 | — | 50 | — | 30 |
| | 1 | | 0.8 | 70 | 100 | 37 | 80 |
| 34 | 0.3 | | 0 | — | 30 | — | 30 |
| | 0.3 | | 0.8 | 58 | 100 | 37 | 100 |
| 38 | 0.3 | | 0 | — | 50 | — | 40 |
| | 0.3 | | 0.8 | 70 | 100 | 46 | 100 |
| 39 | 0.3 | | 0 | — | 50 | — | 50 |
| | 0.3 | | 0.8 | 70 | 100 | 55 | 100 |
| 40 | 0.3 | | 0 | — | 20 | — | 10 |
| | 0.3 | | 0.8 | 52 | 100 | 19 | 70 |
| 42 | 0.3 | | 0 | — | 50 | — | 50 |
| | 0.3 | | 0.8 | 70 | 100 | 55 | 100 |
| sethoxydim | 0.2 | atrazine | 0 | — | 0 | — | 85 |
| | 0.2 | | 0.8 | 40 | 10 | 86 | 40 |
| 9 | 0 | blazer | 0.3 | — | 100 | — | 40 |
| | 0.3 | | 0 | — | 50 | — | 40 |
| | 0.3 | | 0.3 | 100 | 90 | 64 | 30 |
| | 0 | cyanazine | 1 | — | 40 | — | 10 |
| 3 | 1 | cyanazine | 0 | — | 40 | — | 40 |
| | 1 | | 1 | 64 | 85 | 46 | 85 |
| 6 | 1 | | 0 | — | 50 | — | 30 |
| | 1 | | 1 | 70 | 100 | 37 | 70 |
| 7 | 0.3 | | 0 | — | 30 | — | 30 |
| | 0.3 | | 1 | 58 | 100 | 37 | 85 |
| 9 | 0.3 | | 0 | — | 50 | — | 40 |
| | 0.3 | | 1 | 70 | 100 | 46 | 100 |
| 10 | 1 | | 0 | — | 10 | — | 40 |
| | 1 | | 1 | 46 | 85 | 46 | 70 |
| 11 | 1 | | 0 | — | 30 | — | 30 |
| | 1 | | 1 | 58 | 100 | 37 | 100 |
| 13 | 1 | | 0 | — | 70 | — | 70 |

TABLE 8-continued

| Ingredient I (invention compound) | | Mixing Effects Ingredient II | | Herbicidal effects (%) | | | |
|---|---|---|---|---|---|---|---|
| Compound No. | Application rate (kg/ha) | Name of ingredient | Application rate (kg/ha) | Redrood pigweed Ec | Ea | Johnsongrass Ec | Ea |
| | 1 | | 1 | 82 | 100 | 73 | 100 |
| 14 | 0.3 | | 0 | — | 85 | — | 30 |
| | 0.3 | | 1 | 91 | 100 | 37 | 85 |
| 15 | 1 | | 0 | — | 30 | — | 20 |
| | 1 | | 1 | 58 | 100 | 24 | 50 |
| 20 | 0.3 | | 0 | — | 30 | — | 20 |
| | 0.3 | | 1 | 58 | 100 | 24 | 60 |
| 24 | 0.3 | | 0 | — | 50 | — | 30 |
| | 0.3 | | 1 | 75 | 100 | 37 | 85 |
| 27 | 0.3 | | 0 | — | 50 | — | 40 |
| | 0.3 | | 1 | 70 | 100 | 46 | 85 |
| 28 | 0.3 | | 0 | — | 50 | — | 30 |
| | 0.3 | | 1 | 70 | 100 | 37 | 95 |
| 30 | 0.3 | | 0 | — | 40 | — | 20 |
| | 0.3 | | 1 | 64 | 100 | 28 | 100 |
| 32 | 1 | | 0 | — | 50 | — | 30 |
| | 1 | | 1 | 70 | 100 | 37 | 80 |
| 34 | 0.3 | | 0 | — | 30 | — | 30 |
| | 0.3 | | 1 | 58 | 100 | 37 | 100 |
| 38 | 0.3 | | 0 | — | 50 | — | 40 |
| | 0.3 | | 1 | 70 | 100 | 46 | 100 |
| 39 | 0.3 | | 0 | — | 50 | — | 50 |
| | 0.3 | | 1 | 70 | 100 | 55 | 100 |
| 40 | 0.3 | | 0 | — | 20 | — | 30 |
| | 0.3 | | 1 | 52 | 100 | 37 | 70 |
| 42 | 0.3 | | 0 | — | 50 | — | 50 |
| | 0.3 | | 1 | 70 | 100 | 55 | 100 |
| sethoxydim | 0.2 | cyanazine | 0 | — | 0 | — | 95 |
| | 0.2 | | 1 | 40 | 10 | 96 | 40 |
| 9 | 0 | blazer | 0.3 | — | 100 | — | 40 |
| | 0.3 | | 0 | — | 50 | — | 40 |
| | 0.3 | | 0.3 | 100 | 90 | 64 | 30 |
| | 0 | prometryn | 0.5 | — | 30 | — | 20 |
| 3 | 1 | prometryn | 0 | — | 0 | — | 40 |
| | 1 | | 0.5 | 30 | 100 | 52 | 85 |
| 6 | 1 | | 0 | — | 0 | — | 30 |
| | 1 | | 0.5 | 30 | 100 | 44 | 70 |
| 7 | 0.3 | | 0 | — | 10 | — | 40 |
| | 0.3 | | 0.5 | 37 | 100 | 52 | 85 |
| 9 | 0.3 | | 0 | — | 0 | — | 70 |
| | 0.3 | | 0.5 | 30 | 100 | 76 | 100 |
| 10 | 1 | | 0 | — | 0 | — | 20 |
| | 1 | | 0.5 | 30 | 100 | 36 | 70 |
| 11 | 1 | | 0 | — | 0 | — | 0 |
| | 1 | | 0.5 | 30 | 100 | 20 | 50 |
| 13 | 1 | | 0 | — | 10 | — | 50 |
| | 1 | | 0.5 | 37 | 100 | 60 | 100 |
| 14 | 0.3 | | 0 | — | 0 | — | 30 |
| | 0.3 | | 0.5 | 30 | 100 | 44 | 85 |
| 15 | 1 | | 0 | — | 0 | — | 20 |
| | 1 | | 0.5 | 30 | 100 | 36 | 70 |
| 20 | 0.3 | | 0 | — | 10 | — | 0 |
| | 0.3 | | 0.5 | 37 | 100 | 20 | 60 |
| 24 | 0.3 | | 0 | — | 0 | — | 20 |
| | 0.3 | | 0.5 | 30 | 100 | 36 | 85 |
| 27 | 0.3 | | 0 | — | 10 | — | 30 |
| | 0.3 | | 0.5 | 37 | 100 | 44 | 85 |
| 28 | 0.3 | | 0 | — | 0 | — | 30 |
| | 0.3 | | 0.5 | 30 | 100 | 44 | 95 |
| 30 | 0.3 | | 0 | — | 0 | — | 10 |
| | 0.3 | | 0.5 | 30 | 100 | 28 | 100 |
| 32 | 1 | | 0 | — | 0 | — | 30 |
| | 1 | | 0.5 | 30 | 100 | 44 | 80 |
| 34 | 0.3 | | 0 | — | 0 | — | 30 |
| | 0.3 | | 0.5 | 30 | 100 | 44 | 85 |
| 38 | 0.3 | | 0 | — | 10 | — | 40 |
| | 0.3 | | 0.5 | 37 | 100 | 52 | 100 |
| 39 | 0.3 | | 0 | — | 10 | — | 50 |
| | 0.3 | | 0.5 | 37 | 85 | 60 | 100 |
| 40 | 0.3 | | 0 | — | 0 | — | 10 |
| | 0.3 | | 0.5 | 30 | 100 | 28 | 70 |
| 42 | 0.3 | | 0 | — | 10 | — | 50 |
| | 0.3 | | 0.5 | 37 | 100 | 60 | 100 |
| sethoxydim | 0.2 | prometryn | 0 | — | 0 | — | 95 |
| | 0.2 | | 0.5 | 30 | 10 | 96 | 40 |
| 9 | 0 | blazer | 0.3 | — | 100 | — | 40 |
| | 0.3 | | 0 | — | 0 | — | 70 |

TABLE 8-continued

| Ingredient I (invention compound) | | Mixing Effects Ingredient II | | Herbicidal effects (%) | | | |
|---|---|---|---|---|---|---|---|
| | | | | Redrood pigweed | | Johnsongrass | |
| Compound No. | Application rate (kg/ha) | Name of ingredient | Application rate (kg/ha) | Ec | Ea | Ec | Ea |
| | 0.3 | | 0.3 | 100 | 90 | 82 | 40 |
| | 0 | diuron | 0.3 | — | 40 | — | 10 |
| 3 | 1 | diuron | 0 | — | 40 | — | 40 |
| | 1 | | 0.3 | 64 | 100 | 46 | 85 |
| 6 | 1 | | 0 | — | 50 | — | 30 |
| | 1 | | 0.3 | 70 | 100 | 37 | 70 |
| 7 | 0.3 | | 0 | — | 30 | — | 30 |
| | 0.3 | | 0.3 | 58 | 100 | 37 | 85 |
| 9 | 0.3 | | 0 | — | 50 | — | 40 |
| | 0.3 | | 0.3 | 70 | 100 | 46 | 100 |
| 10 | 1 | | 0 | — | 10 | — | 20 |
| | 1 | | 0.3 | 46 | 100 | 24 | 70 |
| 11 | 1 | | 0 | — | 30 | — | 0 |
| | 1 | | 0.3 | 58 | 100 | 10 | 50 |
| 13 | 1 | | 0 | — | 70 | — | 70 |
| | 1 | | 0.3 | 82 | 100 | 73 | 100 |
| 14 | 0.3 | | 0 | — | 85 | — | 30 |
| | 0.3 | | 0.3 | 91 | 100 | 37 | 85 |
| 15 | 1 | | 0 | — | 50 | — | 0 |
| | 1 | | 0.3 | 70 | 100 | 10 | 50 |
| 20 | 0.3 | | 0 | — | 30 | — | 0 |
| | 0.3 | | 0.3 | 58 | 100 | 10 | 60 |
| 24 | 0.3 | | 0 | — | 50 | — | 20 |
| | 0.3 | | 0.3 | 70 | 100 | 24 | 85 |
| 27 | 0.3 | | 0 | — | 50 | — | 30 |
| | 0.3 | | 0.3 | 70 | 100 | 37 | 85 |
| 28 | 0.3 | | 0 | — | 50 | — | 30 |
| | 0.3 | | 0.3 | 70 | 100 | 37 | 95 |
| 30 | 0.3 | | 0 | — | 40 | — | 20 |
| | 0.3 | | 0.3 | 64 | 100 | 28 | 100 |
| 32 | 1 | | 0 | — | 50 | — | 30 |
| | 1 | | 0.3 | 70 | 100 | 37 | 80 |
| 34 | 0.3 | | 0 | — | 30 | — | 30 |
| | 0.3 | | 0.3 | 58 | 100 | 37 | 100 |
| 38 | 0.3 | | 0 | — | 50 | — | 40 |
| | 0.3 | | 0.3 | 70 | 100 | 46 | 100 |
| 39 | 0.3 | | 0 | — | 50 | — | 50 |
| | 0.3 | | 0.3 | 70 | 85 | 55 | 100 |
| 40 | 0.3 | | 0 | — | 20 | — | 10 |
| | 0.3 | | 0.3 | 52 | 100 | 19 | 70 |
| 42 | 0.3 | | 0 | — | 50 | — | 50 |
| | 0.3 | | 0.3 | 70 | 100 | 55 | 100 |
| sethoxydim | 0.2 | diuron | 0 | — | 0 | — | 85 |
| | 0.2 | | 0.3 | 40 | 10 | 86 | 40 |
| 9 | 0 | blazer | 0.3 | — | 100 | — | 40 |
| | 0.3 | | 0 | — | 50 | — | 40 |
| | 0.3 | | 0.3 | 100 | 90 | 64 | 30 |
| | 0 | linuron | 0.3 | — | 30 | — | 10 |
| 3 | 1 | linuron | 0 | — | 0 | — | 40 |
| | 1 | | 0.3 | 30 | 60 | 46 | 85 |
| 6 | 1 | | 0 | — | 0 | — | 30 |
| | 1 | | 0.3 | 30 | 70 | 37 | 70 |
| 7 | 0.3 | | 0 | — | 10 | — | 40 |
| | 0.3 | | 0.3 | 37 | 85 | 46 | 100 |
| 9 | 0.3 | | 0 | — | 0 | — | 70 |
| | 0.3 | | 0.3 | 30 | 100 | 73 | 100 |
| 10 | 1 | | 0 | — | 0 | — | 20 |
| | 1 | | 0.3 | 30 | 70 | 24 | 70 |
| 11 | 1 | | 0 | — | 0 | — | 0 |
| | 1 | | 0.3 | 30 | 70 | 10 | 50 |
| 13 | 1 | | 0 | — | 10 | — | 50 |
| | 1 | | 0.3 | 37 | 85 | 55 | 100 |
| 14 | 0.3 | | 0 | — | 0 | — | 30 |
| | 0.3 | | 0.3 | 30 | 70 | 37 | 85 |
| 15 | 1 | | 0 | — | 0 | — | 0 |
| | 1 | | 0.3 | 30 | 70 | 10 | 50 |
| 20 | 0.3 | | 0 | — | 10 | — | 0 |
| | 0.3 | | 0.3 | 37 | 85 | 10 | 60 |
| 24 | 0.3 | | 0 | — | 0 | — | 20 |
| | 0.3 | | 0.3 | 30 | 85 | 24 | 85 |
| 27 | 0.3 | | 0 | — | 10 | — | 30 |
| | 0.3 | | 0.3 | 37 | 85 | 37 | 100 |
| 28 | 0.3 | | 0 | — | 0 | — | 30 |
| | 0.3 | | 0.3 | 30 | 70 | 37 | 95 |
| 30 | 0.3 | | 0 | — | 0 | — | 10 |
| | 0.3 | | 0.3 | 30 | 70 | 19 | 100 |
| 32 | 1 | | 0 | — | 0 | — | 30 |

TABLE 8-continued

| Ingredient I (invention compound) | | Mixing Effects Ingredient II | | Herbicidal effects (%) | | | |
|---|---|---|---|---|---|---|---|
| Compound No. | Application rate (kg/ha) | Name of ingredient | Application rate (kg/ha) | Redrood pigweed Ec | Ea | Johnsongrass Ec | Ea |
| | 1 | | 0.3 | 30 | 95 | 37 | 80 |
| 34 | 0.3 | | 0 | — | 0 | — | 30 |
| | 0.3 | | 0.3 | 30 | 70 | 37 | 100 |
| 38 | 0.3 | | 0 | — | 10 | — | 40 |
| | 0.3 | | 0.3 | 37 | 85 | 46 | 100 |
| 39 | 0.3 | | 0 | — | 10 | — | 50 |
| | 0.3 | | 0.3 | 37 | 95 | 55 | 100 |
| 40 | 0.3 | | 0 | — | 0 | — | 10 |
| | 0.3 | | 0.3 | 30 | 70 | 19 | 70 |
| 42 | 0.3 | | 0 | — | 10 | — | 50 |
| | 0.3 | | 0.3 | 37 | 85 | 55 | 100 |
| sethoxydim | 0.2 | linuron | 0 | — | 0 | — | 95 |
| | 0.2 | | 0.3 | 30 | 10 | 96 | 40 |
| 9 | 0 | blazer | 0.3 | — | 100 | — | 40 |
| | 0.3 | | 0 | — | 0 | — | 70 |
| | 0.3 | | 0.3 | 100 | 90 | 82 | 40 |
| | 0 | fluometuron | 0.5 | — | 30 | — | 30 |
| 3 | 1 | fluometuron | 0 | — | 40 | — | 40 |
| | 1 | | 0.5 | 58 | 85 | 58 | 85 |
| 6 | 1 | | 0 | — | 50 | — | 30 |
| | 1 | | 0.5 | 65 | 100 | 51 | 70 |
| 7 | 0.3 | | 0 | — | 30 | — | 30 |
| | 0.3 | | 0.5 | 51 | 100 | 51 | 100 |
| 9 | 0.3 | | 0 | — | 50 | — | 70 |
| | 0.3 | | 0.5 | 65 | 100 | 79 | 100 |
| 10 | 1 | | 0 | — | 10 | — | 40 |
| | 1 | | 0.5 | 37 | 85 | 58 | 100 |
| 11 | 1 | | 0 | — | 30 | — | 30 |
| | 1 | | 0.5 | 51 | 100 | 51 | 100 |
| 13 | 1 | | 0 | — | 70 | — | 70 |
| | 1 | | 0.5 | 79 | 100 | 79 | 100 |
| 14 | 0.3 | | 0 | — | 85 | — | 30 |
| | 0.3 | | 0.5 | 90 | 100 | 51 | 100 |
| 15 | 1 | | 0 | — | 30 | — | 20 |
| | 1 | | 0.5 | 51 | 95 | 44 | 85 |
| 20 | 0.3 | | 0 | — | 30 | — | 20 |
| | 0.3 | | 0.5 | 51 | 100 | 44 | 95 |
| 24 | 0.3 | | 0 | — | 50 | — | 30 |
| | 0.3 | | 0.5 | 65 | 100 | 51 | 100 |
| 27 | 0.3 | | 0 | — | 50 | — | 40 |
| | 0.3 | | 0.5 | 65 | 100 | 58 | 100 |
| 28 | 0.3 | | 0 | — | 50 | — | 30 |
| | 0.3 | | 0.5 | 65 | 100 | 51 | 95 |
| 30 | 0.3 | | 0 | — | 40 | — | 20 |
| | 0.3 | | 0.5 | 58 | 100 | 44 | 100 |
| 32 | 1 | | 0 | — | 50 | — | 30 |
| | 1 | | 0.5 | 65 | 100 | 51 | 95 |
| 34 | 0.3 | | 0 | — | 30 | — | 30 |
| | 0.3 | | 0.5 | 51 | 100 | 51 | 100 |
| 38 | 0.3 | | 0 | — | 50 | — | 50 |
| | 0.3 | | 0.5 | 65 | 100 | 65 | 100 |
| 39 | 0.3 | | 0 | — | 50 | — | 70 |
| | 0.3 | | 0.5 | 65 | 100 | 79 | 100 |
| 40 | 0.3 | | 0 | — | 20 | — | 50 |
| | 0.3 | | 0.5 | 44 | 100 | 65 | 85 |
| 42 | 0.3 | | 0 | — | 50 | — | 50 |
| | 0.3 | | 0.5 | 65 | 100 | 65 | 100 |
| sethoxydim | 0.2 | fluometuron | 0 | — | 0 | — | 95 |
| | 0.2 | | 0.5 | 30 | 5 | 97 | 20 |
| 9 | 0 | blazer | 0.3 | — | 100 | — | 40 |
| | 0.3 | | 0 | — | 50 | — | 70 |
| | 0.3 | | 0.3 | 100 | 90 | 82 | 40 |
| | 0 | propanil | 3 | — | 40 | — | 10 |
| 3 | 1 | propanil | 0 | — | 40 | — | 40 |
| | 1 | | 3 | 64 | 100 | 46 | 85 |
| 6 | 1 | | 0 | — | 50 | — | 30 |
| | 1 | | 3 | 70 | 100 | 37 | 95 |
| 7 | 0.3 | | 0 | — | 30 | — | 30 |
| | 0.3 | | 3 | 58 | 100 | 37 | 85 |
| 9 | 0.3 | | 0 | — | 50 | — | 40 |
| | 0.3 | | 3 | 70 | 100 | 46 | 100 |
| 10 | 1 | | 0 | — | 10 | — | 20 |
| | 1 | | 3 | 46 | 100 | 24 | 85 |
| 11 | 1 | | 0 | — | 30 | — | 10 |
| | 1 | | 3 | 58 | 100 | 19 | 50 |
| 13 | 1 | | 0 | — | 70 | — | 70 |
| | 1 | | 3 | 82 | 100 | 73 | 100 |

TABLE 8-continued

| Ingredient I (invention compound) | | Ingredient II | Mixing Effects | Herbicidal effects (%) | | | |
|---|---|---|---|---|---|---|---|
| | | | | Redroot pigweed | | Johnsongrass | |
| Compound No. | Application rate (kg/ha) | Name of ingredient | Application rate (kg/ha) | Ec | Ea | Ec | Ea |
| 14 | 0.3 | | 0 | — | 85 | — | 30 |
| | 0.3 | | 3 | 91 | 100 | 37 | 85 |
| 15 | 1 | | 0 | — | 50 | — | 0 |
| | 1 | | 3 | 70 | 100 | 10 | 70 |
| 20 | 0.3 | | 0 | — | 30 | — | 20 |
| | 0.3 | | 3 | 58 | 100 | 24 | 85 |
| 24 | 0.3 | | 0 | — | 50 | — | 20 |
| | 0.3 | | 3 | 75 | 100 | 24 | 85 |
| 27 | 0.3 | | 0 | — | 50 | — | 30 |
| | 0.3 | | 3 | 70 | 100 | 37 | 85 |
| 28 | 0.3 | | 0 | — | 50 | — | 30 |
| | 0.3 | | 3 | 70 | 100 | 37 | 95 |
| 30 | 0.3 | | 0 | — | 40 | — | 20 |
| | 0.3 | | 3 | 64 | 100 | 28 | 100 |
| 32 | 1 | | 0 | — | 50 | — | 30 |
| | 1 | | 3 | 70 | 100 | 37 | 80 |
| 34 | 0.3 | | 0 | — | 30 | — | 30 |
| | 0.3 | | 3 | 58 | 100 | 37 | 100 |
| 38 | 0.3 | | 0 | — | 50 | — | 40 |
| | 0.3 | | 3 | 70 | 100 | 46 | 100 |
| 39 | 0.3 | | 0 | — | 50 | — | 50 |
| | 0.3 | | 3 | 70 | 85 | 55 | 100 |
| 40 | 0.3 | | 0 | — | 20 | — | 10 |
| | 0.3 | | 3 | 52 | 100 | 19 | 85 |
| 42 | 0.3 | | 0 | — | 50 | — | 50 |
| | 0.3 | | 3 | 70 | 100 | 55 | 100 |
| sethoxydim | 0.2 | propanil | 0 | — | 0 | — | 85 |
| | 0.2 | | 3 | 40 | 10 | 86 | 40 |
| 9 | 0 | blazer | 0.3 | — | 100 | — | 85 |
| | 0.3 | | 0 | — | 50 | — | 40 |
| | 0.3 | | 0.3 | 100 | 90 | 91 | 40 |
| | 0 | metolachlor | 1 | — | 40 | — | 10 |
| 3 | 1 | metolachlor | 0 | — | 40 | — | 20 |
| | 1 | | 1 | 40 | 85 | 28 | 85 |
| 6 | 1 | | 0 | — | 50 | — | 30 |
| | 1 | | 1 | 70 | 100 | 37 | 85 |
| 7 | 0.3 | | 0 | — | 30 | — | 50 |
| | 0.3 | | 1 | 58 | 100 | 55 | 85 |
| 9 | 0.3 | | 0 | — | 50 | — | 70 |
| | 0.3 | | 1 | 70 | 100 | 73 | 100 |
| 10 | 1 | | 0 | — | 20 | — | 20 |
| | 1 | | 1 | 52 | 100 | 24 | 85 |
| 11 | 1 | | 0 | — | 30 | — | 10 |
| | 1 | | 1 | 58 | 95 | 19 | 70 |
| 13 | 1 | | 0 | — | 70 | — | 40 |
| | 1 | | 1 | 82 | 100 | 46 | 100 |
| 14 | 0.3 | | 0 | — | 85 | — | 30 |
| | 0.3 | | 1 | 91 | 100 | 37 | 85 |
| 15 | 1 | | 0 | — | 30 | — | 20 |
| | 1 | | 1 | 58 | 100 | 28 | 70 |
| 20 | 0.3 | | 0 | — | 30 | — | 10 |
| | 0.3 | | 1 | 58 | 100 | 19 | 60 |
| 24 | 0.3 | | 0 | — | 50 | — | 20 |
| | 0.3 | | 1 | 75 | 100 | 24 | 85 |
| 27 | 0.3 | | 0 | — | 50 | — | 30 |
| | 0.3 | | 1 | 70 | 100 | 37 | 95 |
| 28 | 0.3 | | 0 | — | 50 | — | 30 |
| | 0.3 | | 1 | 70 | 100 | 37 | 95 |
| 30 | 0.3 | | 0 | — | 40 | — | 20 |
| | 0.3 | | 1 | 64 | 100 | 28 | 95 |
| 32 | 1 | | 0 | — | 50 | — | 30 |
| | 1 | | 1 | 70 | 100 | 37 | 80 |
| 34 | 0.3 | | 0 | — | 30 | — | 30 |
| | 0.3 | | 1 | 58 | 100 | 37 | 100 |
| 38 | 0.3 | | 0 | — | 50 | — | 40 |
| | 0.3 | | 1 | 70 | 100 | 46 | 100 |
| 39 | 0.3 | | 0 | — | 50 | — | 50 |
| | 0.3 | | 1 | 70 | 85 | 55 | 100 |
| 40 | 0.3 | | 0 | — | 20 | — | 10 |
| | 0.3 | | 1 | 52 | 100 | 19 | 70 |
| 42 | 0.3 | | 0 | — | 50 | — | 50 |
| | 0.3 | | 1 | 70 | 100 | 55 | 100 |
| sethoxydim | 0.2 | metolachlor | 0 | — | 0 | — | 100 |
| | 0.2 | | 1 | 40 | 10 | 100 | 50 |
| 9 | 0 | blazer | 0.3 | — | 100 | — | 40 |
| | 0.3 | | 0 | — | 50 | — | 70 |
| | 0.3 | | 0.3 | 100 | 90 | 82 | 40 |

TABLE 8-continued

| Ingredient I (invention compound) | | Mixing Effects Ingredient II | | Herbicidal effects (%) | | | |
|---|---|---|---|---|---|---|---|
| | | | | Redrood pigweed | | Johnsongrass | |
| Compound No. | Application rate (kg/ha) | Name of ingredient | Application rate (kg/ha) | Ec | Ea | Ec | Ea |
| | 0 | alachlor | 1 | — | 40 | — | 30 |
| 3 | 1 | alachlor | 0 | — | 100 | — | 100 |
| | 1 | | 1 | 100 | 100 | 58 | 100 |
| 6 | 1 | | 0 | — | 50 | — | 30 |
| | 1 | | 1 | 70 | 100 | 51 | 100 |
| 7 | 0.3 | | 0 | — | 30 | — | 30 |
| | 0.3 | | 1 | 58 | 100 | 51 | 100 |
| 9 | 0.3 | | 0 | — | 50 | — | 70 |
| | 0.3 | | 1 | 70 | 100 | 79 | 100 |
| 10 | 1 | | 0 | — | 10 | — | 40 |
| | 1 | | 1 | 46 | 100 | 58 | 70 |
| 11 | 1 | | 0 | — | 30 | — | 30 |
| | 1 | | 1 | 58 | 95 | 51 | 85 |
| 13 | 1 | | 0 | — | 70 | — | 100 |
| | 1 | | 1 | 82 | 100 | 79 | 100 |
| 14 | 0.3 | | 0 | — | 85 | — | 30 |
| | 0.3 | | 1 | 91 | 100 | 51 | 100 |
| 15 | 1 | | 0 | — | 50 | — | 20 |
| | 1 | | 1 | 70 | 100 | 44 | 85 |
| 20 | 0.3 | | 0 | — | 30 | — | 20 |
| | 0.3 | | 1 | 58 | 100 | 44 | 95 |
| 24 | 0.3 | | 0 | — | 50 | — | 30 |
| | 0.3 | | 1 | 75 | 100 | 51 | 100 |
| 27 | 0.3 | | 0 | — | 50 | — | 40 |
| | 0.3 | | 1 | 70 | 100 | 58 | 100 |
| 28 | 0.3 | | 0 | — | 50 | — | 30 |
| | 0.3 | | 1 | 70 | 100 | 51 | 95 |
| 30 | 0.3 | | 0 | — | 40 | — | 20 |
| | 0.3 | | 1 | 64 | 100 | 44 | 100 |
| 32 | 1 | | 0 | — | 50 | — | 30 |
| | 1 | | 1 | 70 | 100 | 51 | 100 |
| 34 | 0.3 | | 0 | — | 30 | — | 30 |
| | 0.3 | | 1 | 58 | 100 | 51 | 100 |
| 38 | 0.3 | | 0 | — | 50 | — | 50 |
| | 0.3 | | 1 | 70 | 100 | 65 | 100 |
| 39 | 0.3 | | 0 | — | 50 | — | 70 |
| | 0.3 | | 1 | 70 | 100 | 79 | 100 |
| 40 | 0.3 | | 0 | — | 20 | — | 50 |
| | 0.3 | | 1 | 52 | 100 | 65 | 100 |
| 42 | 0.3 | | 0 | — | 50 | — | 50 |
| | 0.3 | | 1 | 70 | 100 | 65 | 100 |
| sethoxydim | 0.2 | alachlor | 0 | — | 0 | — | 95 |
| | 0.2 | | 1 | 40 | 10 | 97 | 40 |
| 9 | 0 | blazer | 0.3 | — | 100 | — | 40 |
| | 0.3 | | 0 | — | 50 | — | 70 |
| | 0.3 | | 0.3 | 100 | 90 | 82 | 40 |
| | 0 | metribuzin | 0.2 | — | 30 | — | 10 |
| 3 | 1 | metribuzin | 0 | — | 40 | — | 20 |
| | 1 | | 0.2 | 58 | 100 | 28 | 85 |
| 6 | 1 | | 0 | — | 50 | — | 30 |
| | 1 | | 0.2 | 65 | 100 | 37 | 70 |
| 7 | 0.3 | | 0 | — | 30 | — | 50 |
| | 0.3 | | 0.2 | 51 | 100 | 55 | 95 |
| 9 | 0.3 | | 0 | — | 50 | — | 70 |
| | 0.3 | | 0.2 | 65 | 100 | 73 | 100 |
| 10 | 1 | | 0 | — | 20 | — | 20 |
| | 1 | | 0.2 | 44 | 100 | 24 | 70 |
| 11 | 1 | | 0 | — | 30 | — | 10 |
| | 1 | | 0.2 | 51 | 100 | 19 | 70 |
| 13 | 1 | | 0 | — | 70 | — | 40 |
| | 1 | | 0.2 | 79 | 100 | 46 | 100 |
| 14 | 0.3 | | 0 | — | 85 | — | 30 |
| | 0.3 | | 0.2 | 90 | 100 | 37 | 85 |
| 15 | 1 | | 0 | — | 30 | — | 20 |
| | 1 | | 0.2 | 51 | 100 | 28 | 70 |
| 20 | 0.3 | | 0 | — | 30 | — | 10 |
| | 0.3 | | 0.2 | 51 | 100 | 19 | 60 |
| 24 | 0.3 | | 0 | — | 50 | — | 20 |
| | 0.3 | | 0.2 | 65 | 100 | 24 | 85 |
| 27 | 0.3 | | 0 | — | 50 | — | 30 |
| | 0.3 | | 0.2 | 65 | 100 | 37 | 85 |
| 28 | 0.3 | | 0 | — | 50 | — | 30 |
| | 0.3 | | 0.2 | 65 | 100 | 37 | 95 |
| 30 | 0.3 | | 0 | — | 40 | — | 20 |
| | 0.3 | | 0.2 | 58 | 100 | 28 | 100 |
| 32 | 1 | | 0 | — | 50 | — | 30 |
| | 1 | | 0.2 | 65 | 100 | 37 | 80 |

TABLE 8-continued

| Ingredient I (invention compound) | | Mixing Effects Ingredient II | | Herbicidal effects (%) | | | |
|---|---|---|---|---|---|---|---|
| Compound No. | Application rate (kg/ha) | Name of ingredient | Application rate (kg/ha) | Redrood pigweed | | Johnsongrass | |
| | | | | Ec | Ea | Ec | Ea |
| 34 | 0.3 | | 0 | — | 30 | — | 30 |
| | 0.3 | | 0.2 | 51 | 100 | 37 | 95 |
| 38 | 0.3 | | 0 | — | 50 | — | 40 |
| | 0.3 | | 0.2 | 65 | 100 | 46 | 100 |
| 39 | 0.3 | | 0 | — | 50 | — | 50 |
| | 0.3 | | 0.2 | 65 | 85 | 55 | 100 |
| 40 | 0.3 | | 0 | — | 20 | — | 10 |
| | 0.3 | | 0.2 | 44 | 100 | 19 | 70 |
| 42 | 0.3 | | 0 | — | 50 | — | 50 |
| | 0.3 | | 0.2 | 65 | 100 | 55 | 100 |
| sethoxydim | 0.2 | metribuzin | 0.2 | — | 0 | — | 100 |
| | 0.2 | | 0 | 30 | 10 | 100 | 40 |
| 9 | 0 | blazer | 0.3 | — | 100 | — | 40 |
| | 0.3 | | 0 | — | 50 | — | 70 |
| | 0.3 | | 0.3 | 100 | 90 | 82 | 40 |
| | 0 | bentazon | 0.5 | — | 40 | — | 0 |
| 3 | 1 | bentazon | 0 | — | 100 | — | 40 |
| | 1 | | 0.5 | 100 | 100 | 40 | 85 |
| 6 | 1 | | 0 | — | 50 | — | 30 |
| | 1 | | 0.5 | 70 | 100 | 30 | 70 |
| 7 | 0.3 | | 0 | — | 30 | — | 30 |
| | 0.3 | | 0.5 | 58 | 100 | 30 | 85 |
| 9 | 0.3 | | 0 | — | 50 | — | 40 |
| | 0.3 | | 0.5 | 70 | 100 | 40 | 100 |
| 10 | 1 | | 0 | — | 10 | — | 20 |
| | 1 | | 0.5 | 46 | 85 | 20 | 70 |
| 11 | 1 | | 0 | — | 30 | — | 0 |
| | 1 | | 0.5 | 58 | 100 | 0 | 50 |
| 13 | 1 | | 0 | — | 70 | — | 70 |
| | 1 | | 0.5 | 82 | 100 | 70 | 100 |
| 14 | 0.3 | | 0 | — | 85 | — | 30 |
| | 0.3 | | 0.5 | 91 | 100 | 30 | 85 |
| 15 | 1 | | 0 | — | 50 | — | 0 |
| | 1 | | 0.5 | 70 | 100 | 0 | 50 |
| 20 | 0.3 | | 0 | — | 30 | — | 0 |
| | 0.3 | | 0.5 | 58 | 95 | 0 | 60 |
| 24 | 0.3 | | 0 | — | 50 | — | 20 |
| | 0.3 | | 0.5 | 75 | 100 | 20 | 85 |
| 27 | 0.3 | | 0 | — | 50 | — | 30 |
| | 0.3 | | 0.5 | 70 | 100 | 30 | 85 |
| 28 | 0.3 | | 0 | — | 50 | — | 30 |
| | 0.3 | | 0.5 | 70 | 100 | 30 | 95 |
| 30 | 0.3 | | 0 | — | 40 | — | 20 |
| | 0.3 | | 0.5 | 64 | 100 | 20 | 100 |
| 32 | 1 | | 0 | — | 50 | — | 30 |
| | 1 | | 0.5 | 70 | 100 | 30 | 80 |
| 34 | 0.3 | | 0 | — | 30 | — | 30 |
| | 0.3 | | 0.5 | 58 | 100 | 30 | 100 |
| 38 | 0.3 | | 0 | — | 50 | — | 40 |
| | 0.3 | | 0.5 | 70 | 100 | 40 | 100 |
| 39 | 0.3 | | 0 | — | 50 | — | 50 |
| | 0.3 | | 0.5 | 70 | 95 | 50 | 100 |
| 40 | 0.3 | | 0 | — | 20 | — | 10 |
| | 0.3 | | 0.5 | 52 | 100 | 10 | 70 |
| 42 | 0.3 | | 0 | — | 50 | — | 50 |
| | 0.3 | | 0.5 | 70 | 100 | 50 | 100 |
| sethoxydim | 0.2 | bentazon | 0 | — | 0 | — | 85 |
| | 0.2 | | 0.5 | 40 | 10 | 86 | 40 |
| 9 | 0 | blazer | 0.3 | — | 100 | — | 40 |
| | 0.3 | | 0 | — | 50 | — | 40 |
| | 0.3 | | 0.3 | 100 | 90 | 64 | 30 |
| | 0 | naptalam | 1 | — | 10 | — | 10 |
| 3 | 1 | naptalam | 0 | — | 40 | — | 40 |
| | 1 | | 1 | 46 | 100 | 46 | 85 |
| 6 | 1 | | 0 | — | 50 | — | 30 |
| | 1 | | 1 | 55 | 100 | 37 | 70 |
| 7 | 0.3 | | 0 | — | 30 | — | 30 |
| | 0.3 | | 1 | 37 | 100 | 37 | 85 |
| 9 | 0.3 | | 0 | — | 50 | — | 70 |
| | 0.3 | | 1 | 55 | 100 | 73 | 100 |
| 10 | 1 | | 0 | — | 10 | — | 40 |
| | 1 | | 1 | 19 | 100 | 46 | 70 |
| 11 | 1 | | 0 | — | 30 | — | 30 |
| | 1 | | 1 | 37 | 100 | 37 | 60 |
| 13 | 1 | | 0 | — | 70 | — | 70 |
| | 1 | | 1 | 73 | 100 | 73 | 100 |
| 14 | 0.3 | | 0 | — | 85 | — | 30 |

TABLE 8-continued

| Ingredient I (invention compound) | | Mixing Effects Ingredient II | | Herbicidal effects (%) | | | |
|---|---|---|---|---|---|---|---|
| Compound No. | Application rate (kg/ha) | Name of ingredient | Application rate (kg/ha) | Redrood pigweed | | Johnsongrass | |
| | | | | Ec | Ea | Ec | Ea |
| | 0.3 | | 1 | 87 | 100 | 37 | 85 |
| 15 | 1 | | 0 | — | 30 | — | 20 |
| | 1 | | 1 | 37 | 100 | 24 | 60 |
| 20 | 0.3 | | 0 | — | 30 | — | 20 |
| | 0.3 | | 1 | 37 | 100 | 24 | 70 |
| 24 | 0.3 | | 0 | — | 50 | — | 30 |
| | 0.3 | | 1 | 55 | 100 | 37 | 85 |
| 27 | 0.3 | | 0 | — | 50 | — | 40 |
| | 0.3 | | 1 | 55 | 100 | 46 | 85 |
| 28 | 0.3 | | 0 | — | 50 | — | 30 |
| | 0.3 | | 1 | 55 | 100 | 37 | 95 |
| 30 | 0.3 | | 0 | — | 40 | — | 20 |
| | 0.3 | | 1 | 46 | 100 | 28 | 100 |
| 32 | 1 | | 0 | — | 50 | — | 30 |
| | 1 | | 1 | 55 | 100 | 37 | 80 |
| 34 | 0.3 | | 0 | — | 30 | — | 30 |
| | 0.3 | | 1 | 37 | 100 | 37 | 100 |
| 38 | 0.3 | | 0 | — | 50 | — | 50 |
| | 0.3 | | 1 | 55 | 100 | 55 | 95 |
| 39 | 0.3 | | 0 | — | 50 | — | 70 |
| | 0.3 | | 1 | 55 | 100 | 73 | 100 |
| 40 | 0.3 | | 0 | — | 20 | — | 50 |
| | 0.3 | | 1 | 28 | 85 | 55 | 70 |
| 42 | 0.3 | | 0 | — | 50 | — | 50 |
| | 0.3 | | 1 | 55 | 100 | 55 | 100 |
| sethoxydim | 0.2 | naptalam | 0 | — | 0 | — | 85 |
| | 0.2 | | 1 | 10 | 5 | 86 | 30 |
| 9 | 0 | blazer | 0.3 | — | 100 | — | 40 |
| | 0.3 | | 0 | — | 50 | — | 70 |
| | 0.3 | | 0.3 | 100 | 90 | 82 | 40 |

Test 8:
Upland Foliar Application Test by Mixed Formulations

Resin made 1/10000-are pots were filled with the soil of an upland field. Redroot pigweed and johnsongrass were separately seeded and were allowed to germinate in a green house. When each plant grew to the stage of 2-3 leaves, emulsions formulated with concentration gradient from predetermined amounts of two test compounds of different kinds in a similar manner to the method described in Formulation Example 16 was diluted with water to a predetermined dilution rate and then sprayed at an application rate equal to 5 l per are onto the foliage of each plant by means of a pressure-operated ULV (ultra low volume) sprayer. Influence to the weeds were observed on the 40th day after the spray of the herbicides. The results are shown in Table 9, In the table, Ea and Ec have the same meanings as in Test 7, and Ea>Ec indicates the existence of synergistic action while Ea<Ec indicates the existence of antagonistic action.

In Tests 7 and 8, the compounds of the invention represented by formula [I] showed, upon application in combination with the corresponding photosynthesis inhibiting herbicides, high synergistic effects against broadleaf weeds and gramineous weeds in foliar application and their activities increased as much as about 10 times the activities available when they were used singly. They showed neither such antagonistic action as exhibited by sethoxydim nor such antagonistic action and additive action as shown by blazer.

TABLE 9

| Sample Compound | Application rate (g/a) | Herbicidal effects | | | | Sample Compoound | Application rate (g/a) | Herbicidal effects | | | |
|---|---|---|---|---|---|---|---|---|---|---|---|
| | | Redrood pigweed | | Johnsongrass | | | | Redrood pigweed | | Johnsongrass | |
| | | Ec | Ea | Ec | Ea | | | Ec | Ea | Ec | Ea |
| (Compound 7) | 1 | | 10 | | 10 | (Compound 39) | 1 | | 10 | | 10 |
| | 2 | | 50 | | 20 | | 2 | | 30 | | 20 |
| Atrazine | 2 | | 10 | | 0 | Atrazine | 2 | | 10 | | 0 |
| | 4 | | 30 | | 10 | | 4 | | 30 | | 10 |
| | 8 | | 40 | | 10 | | 8 | | 40 | | 10 |
| (Compound 7) + | 1 + 2 | 19 | 100 | 10 | 100 | (Compound 39) + | 1 + 2 | 19 | 100 | 10 | 100 |
| Atrazine | 1 + 4 | 37 | 100 | 19 | 100 | Atrazine | 1 + 4 | 37 | 100 | 19 | 100 |
| | 1 + 8 | 46 | 100 | 19 | 100 | | 1 + 8 | 46 | 100 | 19 | 100 |
| | 2 + 2 | 55 | 100 | 20 | 100 | | 2 + 2 | 37 | 100 | 20 | 100 |
| | 2 + 4 | 65 | 100 | 28 | 100 | | 2 + 4 | 51 | 100 | 28 | 100 |
| | 2 + 8 | 70 | 100 | 28 | 100 | | 2 + 8 | 58 | 100 | 28 | 100 |
| (Compound 9) | 1 | | 10 | | 10 | (COmpound 44) | 1 | | 10 | | 10 |
| | 2 | | 30 | | 20 | | 2 | | 20 | 10 | |
| Atrazine | 2 | | 10 | | 0 | Atrazine | 2 | | 10 | 0 | |
| | 4 | | 30 | | 10 | | 4 | | 30 | | 10 |
| | 8 | | 40 | | 10 | | 8 | | 40 | | 10 |
| (Compound 9) + | 1 + 2 | 19 | 100 | 10 | 100 | (Compound 44) + | 1 + 2 | 19 | 100 | 10 | 100 |
| Atrazine | 1 + 4 | 37 | 100 | 19 | 100 | Atrazine | 1 + 4 | 37 | 100 | 19 | 100 |
| | 1 + 8 | 46 | 100 | 19 | 100 | | 1 + 8 | 46 | 100 | 19 | 100 |
| | 2 + 2 | 37 | 100 | 20 | 100 | | 2 + 2 | 28 | 100 | 10 | 100 |

TABLE 9-continued

| Sample Compound | Application rate (g/a) | Herbicidal effects | | | | Sample Compound | Application rate (g/a) | Herbicidal effects | | | |
|---|---|---|---|---|---|---|---|---|---|---|---|
| | | Redrood pigweed | | Johnsongrass | | | | Redrood pigweed | | Johnsongrass | |
| | | Ec | Ea | Ec | Ea | | | Ec | Ea | Ec | Ea |
| | 2 + 4 | 51 | 100 | 28 | 100 | | 2 + 4 | 44 | 100 | 19 | 100 |
| | 2 + 8 | 58 | 100 | 28 | 100 | | 2 + 8 | 52 | 100 | 19 | 100 |
| (Compound 13) | 1 | | 20 | | 30 | Sethoxydim | 1 | | 0 | | 70 |
| | 2 | | 40 | | 50 | | 2 | | 0 | | 85 |
| Atrazine | 2 | | 10 | | 0 | Atrazine | 2 | | 10 | | 0 |
| | 4 | | 30 | | 10 | | 4 | | 30 | | 10 |
| | 8 | | 40 | | 10 | | 8 | | 40 | | 10 |
| (Compound 13) + | 1 + 2 | 28 | 100 | 30 | 100 | Sethoxydim + | 1 + 2 | 10 | 10 | 70 | 10 |
| Atrazine | 1 + 4 | 44 | 100 | 37 | 100 | Atrazine | 1 + 4 | 30 | 10 | 73 | 10 |
| | 1 + 8 | 52 | 100 | 44 | 100 | | 1 + 8 | 40 | 20 | 73 | 30 |
| | 2 + 2 | 46 | 100 | 50 | 100 | | 2 + 2 | 10 | 10 | 85 | 0 |
| | 2 + 4 | 58 | 100 | 55 | 100 | | 2 + 4 | 30 | 10 | 87 | 20 |
| | 2 + 8 | 64 | 100 | 60 | 100 | | 2 + 8 | 40 | 20 | 87 | 30 |
| (Compound 7) | 1 | | 10 | | 10 | (Compound 39) | 1 | | 10 | | 10 |
| | 2 | | 50 | | 20 | | 2 | | 30 | | 20 |
| Cyanazine | 4 | | 10 | | 0 | Cyanazine | 4 | | 10 | | 0 |
| | 8 | | 30 | | 10 | | 8 | | 30 | | 10 |
| | 16 | | 50 | | 20 | | 16 | | 50 | | 20 |
| (Compound 7) + | 1 + 4 | 19 | 100 | 10 | 100 | (Compound 39) + | 1 + 4 | 19 | 100 | 10 | 100 |
| Cyanazine | 1 + 8 | 37 | 100 | 19 | 100 | Cyanazine | 1 + 8 | 37 | 100 | 19 | 100 |
| | 1 + 16 | 55 | 100 | 28 | 100 | | 1 + 16 | 55 | 100 | 28 | 100 |
| | 2 + 4 | 55 | 100 | 20 | 100 | | 2 + 4 | 37 | 100 | 20 | 100 |
| | 2 + 8 | 65 | 100 | 28 | 100 | | 2 + 8 | 51 | 100 | 28 | 100 |
| | 2 + 16 | 75 | 100 | 36 | 100 | | 2 + 16 | 65 | 100 | 36 | 100 |
| (Compound 9) | 1 | | 10 | | 10 | (Compound 44) | 1 | | 10 | | 10 |
| | 2 | | 30 | | 20 | | 2 | | 20 | | 10 |
| Cyanazine | 4 | | 10 | | 0 | Cyanazine | 4 | | 10 | | 0 |
| | 8 | | 30 | | 10 | | 8 | | 30 | | 10 |
| | 16 | | 50 | | 20 | | 16 | | 50 | | 20 |
| (Compound 9) + | 1 + 4 | 19 | 100 | 10 | 100 | (Compound 44) + | 1 + 4 | 19 | 100 | 10 | 100 |
| Cyanazine | 1 + 8 | 37 | 100 | 19 | 100 | Cyanazine | 1 + 8 | 37 | 100 | 19 | 100 |
| | 1 + 16 | 55 | 100 | 28 | 100 | | 1 + 16 | 55 | 100 | 28 | 100 |
| | 2 + 4 | 37 | 100 | 20 | 100 | | 2 + 4 | 28 | 100 | 10 | 100 |
| | 2 + 8 | 51 | 100 | 28 | 100 | | 2 + 8 | 44 | 100 | 19 | 100 |
| | 2 + 16 | 65 | 100 | 36 | 100 | | 2 + 16 | 60 | 100 | 28 | 100 |
| (Compound 13) | 1 | | 20 | | 30 | Sethoxydim | 1 | | 0 | | 70 |
| | 2 | | 40 | | 50 | | 2 | | 0 | | 85 |
| Cyanazine | 4 | | 10 | | 0 | Cyanazine | 4 | | 10 | | 0 |
| | 8 | | 30 | | 10 | | 8 | | 30 | | 10 |
| | 16 | | 50 | | 20 | | 16 | | 50 | | 20 |
| (Compound 13) + | 1 + 4 | 28 | 100 | 30 | 100 | Sethoxydim + | 1 + 4 | 10 | 0 | 70 | 20 |
| Cyanazine | 1 + 8 | 44 | 100 | 37 | 100 | Cyanazine | 1 + 8 | 30 | 10 | 73 | 20 |
| | 1 + 16 | 60 | 100 | 44 | 100 | | 1 + 16 | 50 | 30 | 76 | 30 |
| | 2 + 4 | 46 | 100 | 50 | 100 | | 2 + 4 | 10 | 10 | 85 | 20 |
| | 2 + 8 | 58 | 100 | 55 | 100 | | 2 + 8 | 30 | 20 | 87 | 40 |
| | 2 + 16 | 70 | 100 | 60 | 100 | | 2 + 16 | 50 | 30 | 88 | 30 |
| (Compound 7) | 1 | | 10 | | 10 | (Compound 39) | 1 | | 10 | | 10 |
| | 2 | | 50 | | 20 | | 2 | | 30 | | 20 |
| Ametryn | 2 | | 10 | | 0 | Ametryn | 2 | | 10 | | 0 |
| | 4 | | 20 | | 10 | | 4 | | 20 | | 10 |
| | 8 | | 30 | | 20 | | 8 | | 30 | | 20 |
| (Compound 7) + | 1 + 2 | 19 | 100 | 10 | 100 | (Compound 39) + | 1 + 2 | 19 | 100 | 10 | 100 |
| Ametryn | 1 + 4 | 28 | 100 | 19 | 100 | Ametryn | 1 + 4 | 28 | 100 | 19 | 100 |
| | 1 + 8 | 37 | 100 | 28 | 100 | | 1 + 8 | 37 | 100 | 28 | 100 |
| | 2 + 2 | 55 | 100 | 20 | 100 | | 2 + 2 | 37 | 100 | 20 | 100 |
| | 2 + 4 | 60 | 100 | 28 | 100 | | 2 + 4 | 44 | 100 | 28 | 100 |
| | 2 + 8 | 65 | 100 | 36 | 100 | | 2 + 8 | 51 | 100 | 36 | 100 |
| (Compound 9) | 1 | | 10 | | 10 | (Compound 44) | 1 | | 10 | | 10 |
| | 2 | | 30 | | 20 | | 2 | | 20 | | 10 |
| Ametryn | 2 | | 10 | | 0 | Ametryn | 2 | | 10 | | 0 |
| | 4 | | 20 | | 10 | | 4 | | 20 | | 10 |
| | 8 | | 30 | | 20 | | 8 | | 30 | | 20 |
| (Compound 9) + | 1 + 2 | 19 | 100 | 10 | 100 | (Compound 44) + | 1 + 2 | 19 | 100 | 10 | 100 |
| Ametryn | 1 + 4 | 28 | 100 | 19 | 100 | Ametryn | 1 + 4 | 28 | 100 | 19 | 100 |
| | 1 + 8 | 37 | 100 | 28 | 100 | | 1 + 8 | 37 | 100 | 28 | 100 |
| | 2 + 2 | 37 | 100 | 20 | 100 | | 2 + 2 | 28 | 100 | 10 | 100 |
| | 2 + 4 | 44 | 100 | 28 | 100 | | 2 + 4 | 36 | 100 | 19 | 100 |
| | 2 + 8 | 51 | 100 | 36 | 100 | | 2 + 8 | 44 | 100 | 28 | 100 |
| (Compound 13) | 1 | | 20 | | 30 | Sethoxydim | 1 | | 0 | | 70 |
| | 2 | | 40 | | 50 | | 2 | | 0 | | 85 |
| Ametryn | 2 | | 10 | | 0 | Ametryn | 2 | | 10 | | 0 |
| | 4 | | 20 | | 10 | | 4 | | 20 | | 10 |
| | 8 | | 30 | | 20 | | 8 | | 30 | | 20 |
| (Compound 13) + | 1 + 2 | 28 | 100 | 30 | 100 | Sethoxydim + | 1 + 2 | 10 | 10 | 70 | 10 |
| Ametryn | 1 + 4 | 36 | 100 | 37 | 100 | Ametryn | 1 + 4 | 20 | | | |
| | 1 + 8 | 44 | 100 | 44 | 100 | | 1 + 8 | 30 | 10 | 76 | 20 |
| | 2 + 2 | 46 | 100 | 50 | 100 | | 2 + 2 | 10 | 10 | 85 | 10 |
| | 2 + 4 | 52 | 100 | 55 | 100 | | 2 + 4 | 20 | 10 | 87 | 10 |

TABLE 9-continued

| Sample Compound | Application rate (g/a) | Herbicidal effects | | | | Sample Compound | Application rate (g/a) | Herbicidal effects | | | |
|---|---|---|---|---|---|---|---|---|---|---|---|
| | | Redrood pigweed | | Johnsongrass | | | | Redrood pigweed | | Johnsongrass | |
| | | Ec | Ea | Ec | Ea | | | Ec | Ea | Ec | Ea |
| | 2 + 8 | 58 | 100 | 60 | 100 | | 2 + 8 | 30 | 20 | 88 | 30 |
| (Compound 7) | 1 | | 10 | | 10 | (Compound 39) | 1 | | 10 | | 10 |
| | 2 | | 50 | | 20 | | 2 | | 30 | | 20 |
| Prometryn | 2 | | 10 | | 0 | Prometryn | 2 | | 10 | | 0 |
| | 4 | | 20 | | 10 | | 4 | | 20 | | 10 |
| | 8 | | 40 | | 20 | | 8 | | 40 | | 20 |
| (Compound 7) + | 1 + 2 | 19 | 100 | 10 | 100 | (Compound 39) + | 1 + 2 | 19 | 100 | 10 | 100 |
| Prometryn | 1 + 4 | 28 | 100 | 19 | 100 | Prometryn | 1 + 4 | 28 | 100 | 19 | 100 |
| | 1 + 8 | 46 | 100 | 28 | 100 | | 1 + 8 | 46 | 100 | 28 | 100 |
| | 2 + 2 | 55 | 100 | 20 | 100 | | 2 + 2 | 37 | 100 | 20 | 100 |
| | 2 + 4 | 60 | 100 | 28 | 100 | | 2 + 4 | 44 | 100 | 28 | 100 |
| | 2 + 8 | 70 | 100 | 36 | 100 | | 2 + 8 | 58 | 100 | 36 | 100 |
| (Compound 9) | 1 | | 10 | | 10 | (Compound 44) | 1 | | 10 | | 10 |
| | 2 | | 30 | | 20 | | 2 | | 20 | | 10 |
| Prometryn | 2 | | 10 | | 0 | Prometryn | 2 | | 10 | | 0 |
| | 4 | | 20 | | 10 | | 4 | | 20 | | 10 |
| | 8 | | 40 | | 20 | | 8 | | 40 | | 20 |
| (Compound 9) + | 1 + 2 | 19 | 100 | 10 | 100 | (Compound 44) + | 1 + 2 | 19 | 100 | 10 | 100 |
| Prometryn | 1 + 4 | 28 | 100 | 19 | 100 | Prometryn | 1 + 4 | 28 | 100 | 19 | 100 |
| | 1 + 8 | 46 | 100 | 28 | 100 | | 1 + 8 | 46 | 100 | 28 | 100 |
| | 2 + 2 | 37 | 100 | 20 | 100 | | 2 + 2 | 28 | 100 | 19 | 100 |
| | 2 + 4 | 44 | 100 | 28 | 100 | | 2 + 4 | 36 | 100 | 19 | 100 |
| | 2 + 8 | 58 | 100 | 36 | 100 | | 2 + 8 | 52 | 100 | 28 | 100 |
| (Compound 13) | 1 | | 20 | | 30 | Sethoxydim | 1 | | 0 | | 70 |
| | 2 | | 40 | | 50 | | 2 | | 0 | | 85 |
| Prometryn | 2 | | 10 | | 0 | Prometryn | 2 | | 10 | | 0 |
| | 4 | | 20 | | 10 | | 4 | | 20 | | 10 |
| | 8 | | 40 | | 20 | | 8 | | 40 | | 20 |
| (Compound 13) + | 1 + 2 | 28 | 100 | 30 | 100 | Sethoxydim + | 1 + 2 | 10 | 20 | 70 | 10 |
| Prometryn | 1 + 4 | 36 | 100 | 37 | 100 | Prometryn | 1 + 4 | 20 | 20 | 73 | 20 |
| | 1 + 8 | 52 | 100 | 44 | 100 | | 1 + 8 | 40 | 30 | 76 | 30 |
| | 2 + 2 | 46 | 100 | 50 | 100 | | 2 + 2 | 10 | 10 | 85 | 10 |
| | 2 + 4 | 52 | 100 | 55 | 100 | | 2 + 4 | 20 | 30 | 87 | 30 |
| | 2 + 8 | 64 | 100 | 60 | 100 | | 2 + 8 | 40 | 30 | 88 | 30 |
| (Compound 7) | 1 | | 10 | | 10 | (Compound 39) | 1 | | 10 | | 10 |
| | 2 | | 50 | | 20 | | 2 | | 30 | | 20 |
| Diuron | 2 | | 30 | | 0 | Diuron | 2 | | 30 | | 0 |
| | 4 | | 70 | | 10 | | 4 | | 70 | | 10 |
| | 8 | | 85 | | 20 | | 8 | | 85 | | 20 |
| (Compound 7) + | 1 + 2 | 37 | 100 | 10 | 100 | (Compound 39) + | 1 + 2 | 37 | 100 | 10 | 100 |
| Diuron | 1 + 4 | 73 | 100 | 19 | 100 | Diuron | 1 + 4 | 73 | 100 | 19 | 100 |
| | 1 + 8 | 87 | 100 | 28 | 100 | | 1 + 8 | 87 | 100 | 28 | 100 |
| | 2 + 2 | 65 | 100 | 20 | 100 | | 2 + 2 | 51 | 100 | 20 | 100 |
| | 2 + 4 | 85 | 100 | 28 | 100 | | 2 + 4 | 79 | 100 | 29 | 100 |
| | 2 + 8 | 93 | 100 | 36 | 100 | | 2 + 8 | 90 | 100 | 36 | 100 |
| (Compound 9) | 1 | | 10 | | 10 | (Compound 44) | 1 | | 10 | | 10 |
| | 2 | | 30 | | 20 | | 2 | | 20 | | 10 |
| Diuron | 2 | | 30 | | 0 | Diuron | 2 | | 30 | | 0 |
| | 4 | | 70 | | 10 | | 4 | | 70 | | 10 |
| | 8 | | 85 | | 20 | | 8 | | 85 | | 20 |
| (Compound 9) + | 1 + 2 | 37 | 100 | 10 | 100 | (Compound 44) + | 1 + 2 | 37 | 100 | 10 | 100 |
| Diuron | 1 + 4 | 73 | 100 | 19 | 100 | Diuron | 1 + 4 | 73 | 100 | 19 | 100 |
| | 1 + 8 | 87 | 100 | 28 | 100 | | 1 + 8 | 87 | 100 | 28 | 100 |
| | 2 + 2 | 51 | 100 | 20 | 100 | | 2 + 2 | 44 | 100 | 10 | 100 |
| | 2 + 4 | 79 | 100 | 28 | 100 | | 2 + 4 | 76 | 100 | 19 | 100 |
| | 2 + 8 | 90 | 100 | 36 | 100 | | 2 + 8 | 88 | 100 | 28 | 100 |
| (Compound 13) | 1 | | 20 | | 30 | Sethoxydim | 1 | | 0 | | 70 |
| | 2 | | 40 | | 50 | | 2 | | 0 | | 85 |
| Diuron | 2 | | 30 | | 0 | Diuron | 2 | | 30 | | 0 |
| | 4 | | 70 | | 10 | | 4 | | 70 | | 10 |
| | 8 | | 85 | | 20 | | 8 | | 85 | | 20 |
| (Compound 13) + | 1 + 2 | 44 | 100 | 30 | 100 | Sethoxydim + | 1 + 2 | 30 | 20 | 70 | 10 |
| Diuron | 1 + 4 | 76 | 100 | 37 | 100 | Diuron | 1 + 4 | 70 | 50 | 73 | 20 |
| | 1 + 8 | 88 | 100 | 44 | 100 | | 1 + 8 | 85 | 70 | 76 | 30 |
| | 2 + 2 | 58 | 100 | 50 | 100 | | 2 + 2 | 30 | 30 | 85 | 0 |
| | 2 + 4 | 82 | 100 | 55 | 100 | | 2 + 4 | 70 | 50 | 87 | 30 |
| | 2 + 8 | 91 | 100 | 60 | 100 | | 2 + 8 | 85 | 50 | 88 | 30 |
| (Compound 7) | 1 | | 10 | | 10 | (Compound 39) | 1 | | 10 | | 10 |
| | 2 | | 50 | | 20 | | 2 | | 30 | | 20 |
| Linuron | 2 | | 40 | | 0 | Linuron | 2 | | 40 | | 0 |
| | 4 | | 70 | | 10 | | 4 | | 70 | | 10 |
| | 8 | | 85 | | 20 | | 8 | | 85 | | 20 |
| (Compound 7) + | 1 + 2 | 46 | 100 | 10 | 100 | (Compound 39) + | 1 + 2 | 46 | 100 | 10 | 100 |
| Linuron | 1 + 4 | 73 | 100 | 19 | 100 | Linuron | 1 + 4 | 73 | 100 | 19 | 100 |
| | 1 + 8 | 87 | 100 | 28 | 100 | | 1 + 8 | 87 | 100 | 28 | 100 |
| | 2 + 2 | 70 | 100 | 20 | 100 | | 2 + 2 | 58 | 100 | 20 | 100 |
| | 2 + 4 | 85 | 100 | 28 | 100 | | 2 + 4 | 79 | 100 | 28 | 100 |
| | 2 + 8 | 93 | 100 | 36 | 100 | | 2 + 8 | 90 | 100 | 36 | 100 |

TABLE 9-continued

| Sample Compound | Application rate (g/a) | Herbicidal effects | | | | Sample Compoound | Application rate (g/a) | Herbicidal effects | | | |
|---|---|---|---|---|---|---|---|---|---|---|---|
| | | Redrood pigweed | | Johnsongrass | | | | Redrood pigweed | | Johnsongrass | |
| | | Ec | Ea | Ec | Ea | | | Ec | Ea | Ec | Ea |
| (Compound 9) | 1 | | 10 | | 10 | (Compound 44) | 1 | | 10 | | 10 |
| | 2 | | 30 | | 20 | | 2 | | 20 | | 10 |
| Linuron | 2 | | 40 | | 0 | Linuron | 2 | | 40 | | 0 |
| | 4 | | 70 | | 10 | | 4 | | 70 | | 10 |
| | 8 | | 85 | | 20 | | 8 | | 85 | | 20 |
| (Compound 9) + | 1 + 2 | 46 | 100 | 10 | 100 | (Compound 44) + | 1 + 2 | 46 | 100 | 10 | 100 |
| Linuron | 1 + 4 | 73 | 100 | 19 | 100 | Linuron | 1 + 4 | 73 | 100 | 19 | 100 |
| | 1 + 8 | 87 | 100 | 28 | 100 | | 1 + 8 | 87 | 100 | 28 | 100 |
| | 2 + 2 | 58 | 100 | 20 | 100 | | 2 + 2 | 52 | 100 | 10 | 100 |
| | 2 + 4 | 79 | 100 | 28 | 100 | | 2 + 4 | 76 | 100 | 19 | 100 |
| | 2 + 8 | 90 | 100 | 36 | 100 | | 2 + 8 | 88 | 100 | 28 | 100 |
| (Compound 13) | 1 | | 20 | | 30 | Sethoxydim | 1 | | 0 | | 70 |
| | 2 | | 40 | | 50 | | 2 | | 0 | | 85 |
| Linuron | 2 | | 40 | | 0 | Linuron | 2 | | 40 | | 0 |
| | 4 | | 70 | | 10 | | 4 | | 70 | | 10 |
| | 8 | | 85 | | 20 | | 8 | | 85 | | 20 |
| (Compound 13) + | 1 + 2 | 52 | 100 | 30 | 100 | Sethoxydim + | 1 + 2 | 40 | 20 | 70 | 10 |
| Linuron | 1 + 4 | 76 | 100 | 37 | 100 | Linuron | 1 + 4 | 70 | 50 | 73 | 20 |
| | 1 + 8 | 88 | 100 | 44 | 100 | | 1 + 8 | 85 | 50 | 76 | 30 |
| | 2 + 2 | 64 | 100 | 50 | 100 | | 2 + 2 | 40 | 20 | 85 | 10 |
| | 2 + 4 | 82 | 100 | 55 | 100 | | 2 + 4 | 70 | 50 | 87 | 30 |
| | 2 + 8 | 91 | 100 | 60 | 100 | | 2 + 8 | 85 | 50 | 88 | 30 |
| (Compound 7) | 1 | | 10 | | 10 | (Compound 39) | 1 | | 10 | | 10 |
| | 2 | | 50 | | 20 | | 2 | | 30 | | 20 |
| Fluometuron | 2 | | 20 | | 0 | Fluometuron | 2 | | 20 | | 0 |
| | 4 | | 30 | | 10 | | 4 | | 30 | | 10 |
| | 8 | | 50 | | 20 | | 8 | | 50 | | 20 |
| (Compound 7) + | 1 + 2 | 28 | 100 | 10 | 100 | (Compound 39) + | 1 + 2 | 28 | 100 | 10 | 100 |
| Fluometuron | 1 + 4 | 37 | 100 | 19 | 100 | Fluometuron | 1 + 4 | 37 | 100 | 19 | 100 |
| | 1 + 8 | 55 | 100 | 29 | 100 | | 1 + 8 | 55 | 100 | 28 | 100 |
| | 2 + 2 | 60 | 100 | 20 | 100 | | 2 + 2 | 44 | 100 | 20 | 100 |
| | 2 + 4 | 65 | 100 | 28 | 100 | | 2 + 4 | 51 | 100 | 28 | 100 |
| | 2 + 8 | 75 | 100 | 36 | 100 | | 2 + 8 | 65 | 100 | 36 | 100 |
| (Compound 9) | 1 | | 10 | | 10 | (Compound 44) | 1 | | 10 | | 10 |
| | 2 | | 30 | | 20 | | 2 | | 20 | | 10 |
| Fluometuron | 2 | | 20 | | 0 | Fluometuron | 2 | | 20 | | 0 |
| | 4 | | 30 | | 10 | | 4 | | 30 | | 10 |
| | 8 | | 50 | | 20 | | 8 | | 50 | | 20 |
| (Compound 9) + | 1 + 2 | 28 | 100 | 10 | 100 | (Compound 44) | 1 + 2 | 28 | 100 | 10 | 100 |
| Fluometuron | 1 + 4 | 37 | 100 | 19 | 100 | Fluometuron | 1 + 4 | 37 | 100 | 19 | 100 |
| | 1 + 8 | 55 | 100 | 28 | 100 | | 1 + 8 | 55 | 100 | 28 | 100 |
| | 2 + 2 | 44 | 100 | 20 | 100 | | 2 + 2 | 36 | 100 | 10 | 100 |
| | 2 + 4 | 51 | 100 | 28 | 100 | | 2 + 4 | 44 | 100 | 19 | 100 |
| | 2 + 8 | 65 | 100 | 36 | 100 | | 2 + 8 | 60 | 100 | 28 | 100 |
| (Compound 13) | 1 | | 20 | | 30 | Sethoxydim | 1 | | 0 | | 70 |
| | 2 | | 40 | | 50 | | 2 | | 0 | | 85 |
| Fluometuron | 2 | | 20 | | 0 | Fluometuron | 2 | | 20 | | 0 |
| | 4 | | 40 | | 10 | | 4 | | 40 | | 10 |
| | 8 | | 50 | | 20 | | 8 | | 50 | | 20 |
| (Compound 13) + | 1 + 2 | 36 | 100 | 30 | 100 | Sethoxydim + | 1 + 2 | 20 | 0 | 70 | 50 |
| Fluometuron | 1 + 4 | 44 | 100 | 37 | 100 | Fluometuron | 1 + 4 | 30 | 10 | 73 | 50 |
| | 1 + 8 | 60 | 100 | 44 | 100 | | 1 + 8 | 50 | 30 | 76 | 30 |
| | 2 + 2 | 52 | 100 | 50 | 100 | | 2 + 2 | 20 | 0 | 85 | 10 |
| | 2 + 4 | 58 | 100 | 55 | 100 | | 2 + 4 | 30 | 0 | 87 | 30 |
| | 2 + 8 | 70 | 100 | 60 | 100 | | 2 + 8 | 50 | 40 | 88 | 50 |
| (Compound 7) | 1 | | 10 | | 10 | (Compound 39) | 1 | | 10 | | 10 |
| | 2 | | 50 | | 20 | | 2 | | 30 | | 20 |
| Isoproturon | 2 | | 10 | | 0 | Isoproturon | 2 | | 10 | | 0 |
| | 4 | | 20 | | 10 | | 4 | | 20 | | 10 |
| | 8 | | 40 | | 20 | | 8 | | 40 | | 20 |
| (Compound 7) + | 1 + 2 | 19 | 100 | 10 | 100 | (Compound 39) + | 1 + 2 | 19 | 100 | 10 | 100 |
| Isoproturon | 1 + 4 | 28 | 100 | 19 | 100 | Isoproturon | 1 + 4 | 28 | 100 | 19 | 100 |
| | 1 + 8 | 46 | 100 | 28 | 100 | | 1 + 8 | 46 | 100 | 28 | 100 |
| | 2 + 2 | 55 | 100 | 20 | 100 | | 2 + 2 | 37 | 100 | 20 | 100 |
| | 2 + 4 | 60 | 100 | 28 | 100 | | 2 + 4 | 44 | 100 | 28 | 100 |
| | 2 + 8 | 70 | 100 | 36 | 100 | | 2 + 8 | 58 | 100 | 36 | 100 |
| (Compound 9) | 1 | | 10 | | 10 | (Compound 44) | 1 | | 10 | | 10 |
| | 2 | | 30 | | 20 | | 2 | | 20 | | 10 |
| Isoproturon | 2 | | 10 | | 0 | Isoproturon | 2 | | 10 | | 0 |
| | 4 | | 20 | | 10 | | 4 | | 20 | | 10 |
| | 8 | | 40 | | 20 | | 8 | | 40 | | 20 |
| (Compound 9) + | 1 + 2 | 19 | 100 | 10 | 100 | (Compound 44) + | 1 + 2 | 19 | 100 | 10 | 100 |
| Isoproturon | 1 + 4 | 28 | 100 | 19 | 100 | Isoproturon | 1 + 4 | 28 | 100 | 19 | 100 |
| | 1 + 8 | 46 | 100 | 28 | 100 | | 1 + 8 | 46 | 100 | 28 | 100 |
| | 2 + 2 | 37 | 100 | 20 | 100 | | 2 + 2 | 28 | 100 | 10 | 100 |
| | 2 + 4 | 44 | 100 | 29 | 100 | | 2 + 4 | 36 | 100 | 19 | 100 |
| | 2 + 8 | 58 | 100 | 36 | 100 | | 2 + 8 | 52 | 100 | 28 | 100 |
| (Compound 13) | 1 | | 20 | | 30 | Sethoxydim | 1 | | 0 | | 70 |

TABLE 9-continued

| Sample Compound | Application rate (g/a) | Herbicidal effects Redrood pigweed Ec | Herbicidal effects Redrood pigweed Ea | Herbicidal effects Johnsongrass Ec | Herbicidal effects Johnsongrass Ea | Sample Compoound | Application rate (g/a) | Herbicidal effects Redrood pigweed Ec | Herbicidal effects Redrood pigweed Ea | Herbicidal effects Johnsongrass Ec | Herbicidal effects Johnsongrass Ea |
|---|---|---|---|---|---|---|---|---|---|---|---|
| | 2 | | 40 | | 50 | | 2 | | 0 | | 85 |
| Isoproturon | 2 | | 10 | | 0 | Isoproturon | 2 | | 10 | | 0 |
| | 4 | | 20 | | 10 | | 4 | | 20 | | 10 |
| | 8 | | 40 | | 20 | | 8 | | 40 | | 20 |
| (Compound 13) + | 1 + 2 | 28 | 100 | 30 | 100 | Sethoxydim + | 1 + 2 | 10 | 0 | 70 | 20 |
| Isoproturon | 1 + 4 | 36 | 100 | 37 | 100 | Isoproturon | 1 + 4 | 20 | 10 | 73 | 30 |
| | 1 + 8 | 52 | 100 | 44 | 100 | | 1 + 8 | 40 | 20 | 76 | 30 |
| | 2 + 2 | 46 | 100 | 50 | 100 | | 2 + 2 | 10 | 0 | 85 | 0 |
| | 2 + 4 | 52 | 100 | 55 | 100 | | 2 + 4 | 20 | 20 | 87 | 30 |
| | 2 + 8 | 64 | 100 | 60 | 100 | | 2 + 8 | 40 | 20 | 88 | 30 |
| (Compound 7) | 1 | | 10 | | 10 | (Compound 39) | 1 | | 10 | | 10 |
| | 2 | | 50 | | 20 | | 2 | | 30 | | 20 |
| Propanil | 20 | | 30 | | 20 | Propanil | 20 | | 30 | | 20 |
| | 40 | | 70 | | 30 | | 40 | | 70 | | 30 |
| | 80 | | 70 | | 50 | | 80 | | 70 | | 50 |
| (Compound 7) + | 1 + 20 | 37 | 100 | 28 | 100 | (Compound 39) + | 1 + 20 | 37 | 100 | 28 | 100 |
| Propanil | 1 + 40 | 73 | 100 | 37 | 100 | Propanil | 1 + 40 | 73 | 100 | 37 | 100 |
| | 1 + 80 | 73 | 100 | 55 | 100 | | 1 + 80 | 73 | 100 | 55 | 100 |
| | 2 + 20 | 65 | 100 | 36 | 100 | | 2 + 20 | 51 | 100 | 36 | 100 |
| | 2 + 40 | 85 | 100 | 44 | 100 | | 2 + 40 | 79 | 100 | 44 | 100 |
| | 2 + 80 | 85 | 100 | 60 | 100 | | 2 + 80 | 79 | 100 | 60 | 100 |
| (Compound 9) | 1 | | 10 | | 10 | (Compound 44) | 1 | | 10 | | 10 |
| | 2 | | 30 | | 20 | | 2 | | 20 | | 10 |
| Propanil | 20 | | 30 | | 20 | Propanil | 20 | | 30 | | 20 |
| | 40 | | 70 | | 30 | | 40 | | 70 | | 30 |
| | 80 | | 70 | | 50 | | 80 | | 70 | | 50 |
| (Compound 9) + | 1 + 20 | 37 | 100 | 28 | 100 | (Compound 44) + | 1 + 20 | 37 | 100 | 28 | 100 |
| Propanil | 1 + 40 | 73 | 100 | 37 | 100 | Propanil | 1 + 40 | 73 | 100 | 37 | 100 |
| | 1 + 80 | 73 | 100 | 55 | 100 | | 1 + 80 | 73 | 100 | 55 | 100 |
| | 2 + 20 | 51 | 100 | 36 | 100 | | 2 + 20 | 44 | 100 | 28 | 100 |
| | 2 + 40 | 79 | 100 | 44 | 100 | | 2 + 40 | 76 | 100 | 37 | 100 |
| | 2 + 80 | 79 | 100 | 60 | 100 | | 2 + 80 | 76 | 100 | 55 | 100 |
| (Compound 13) | 1 | | 20 | | 30 | Sethoxydim | 1 | | 0 | | 70 |
| | 2 | | 40 | | 50 | | 2 | | 0 | | 85 |
| Propanil | 20 | | 30 | | 20 | Propanil | 20 | | 30 | | 20 |
| | 40 | | 70 | | 30 | | 40 | | 70 | | 30 |
| | 80 | | 70 | | 50 | | 80 | | 70 | | 50 |
| (Compound 13) + | 1 + 20 | 44 | 100 | 44 | 100 | Sethoxydim + | 1 + 20 | 30 | 20 | 76 | 50 |
| Propanil | 1 + 40 | 76 | 100 | 51 | 100 | Propanil | 1 + 40 | 70 | 50 | 79 | 40 |
| | 1 + 80 | 76 | 100 | 65 | 100 | | 1 + 80 | 70 | 70 | 85 | 40 |
| | 2 + 20 | 58 | 100 | 60 | 100 | | 2 + 20 | 30 | 30 | 88 | 40 |
| | 2 + 40 | 82 | 100 | 65 | 100 | | 2 + 40 | 70 | 50 | 90 | 50 |
| | 2 + 80 | 82 | 100 | 75 | 100 | | 2 + 80 | 70 | 50 | 92 | 50 |
| (Compound 7) | 1 | | 10 | | 01 | (Compound 39) | 1 | | 10 | | 10 |
| | 2 | | 50 | | 20 | | 2 | | 30 | | 20 |
| MT-5950 | 2 | | 30 | | 10 | MT-5950 | 2 | | 30 | | 10 |
| | 4 | | 70 | | 10 | | 4 | | 70 | | 10 |
| | 8 | | 85 | | 20 | | 8 | | 85 | | 20 |
| (Compound 7) + | 1 + 2 | 37 | 100 | 19 | 100 | (Compound 39) + | 1 + 2 | 37 | 100 | 19 | 100 |
| MT-5950 | 1 + 4 | 73 | 100 | 19 | 100 | MT-5950 | 1 + 4 | 73 | 100 | 19 | 100 |
| | 1 + 8 | 87 | 100 | 28 | 100 | | 1 + 8 | 87 | 100 | 28 | 100 |
| | 2 + 2 | 65 | 100 | 28 | 100 | | 2 + 2 | 51 | 100 | 28 | 100 |
| | 2 + 4 | 85 | 100 | 28 | 100 | | 2 + 4 | 79 | 100 | 28 | 100 |
| | 2 + 8 | 93 | 100 | 36 | 100 | | 2 + 8 | 90 | 100 | 36 | 100 |
| (Compound 9) | 1 | | 10 | | 10 | (Compound 44) | 1 | | 10 | | 10 |
| | 2 | | 30 | | 20 | | 2 | | 20 | | 10 |
| MT-5950 | 2 | | 30 | | 10 | MT-5950 | 2 | | 30 | | 10 |
| | 4 | | 70 | | 10 | | 4 | | 70 | | 10 |
| | 8 | | 85 | | 20 | | 8 | | 85 | | 20 |
| (Compound 9) + | 1 + 2 | 37 | 100 | 19 | 100 | (Compound 44) + | 1 + 2 | 37 | 100 | 19 | 100 |
| MT-5950 | 1 + 4 | 73 | 100 | 19 | 100 | MT-5950 | 1 + 4 | 73 | 100 | 19 | 100 |
| | 1 + 8 | 87 | 100 | 28 | 100 | | 1 + 8 | 87 | 100 | 28 | 100 |
| | 2 + 2 | 51 | 100 | 28 | 100 | | 2 + 2 | 44 | 100 | 19 | 100 |
| | 2 + 4 | 79 | 100 | 28 | 100 | | 2 + 4 | 76 | 100 | 19 | 100 |
| | 2 + 8 | 90 | 100 | 36 | 100 | | 2 + 8 | 88 | 100 | 28 | 100 |
| (Compound 13) | 1 | | 20 | | 30 | Sethoxydim | 1 | | 0 | | 70 |
| | 2 | | 40 | | 50 | | 2 | | 0 | | 85 |
| MT-5950 | 2 | | 30 | | 10 | MT-5950 | 2 | | 30 | | 10 |
| | 4 | | 70 | | 10 | | 4 | | 70 | | 10 |
| | 8 | | 85 | | 20 | | 8 | | 85 | | 20 |
| (Compound 13) + | 1 + 2 | 44 | 100 | 37 | 100 | Sethoxydim + | 1 + 2 | 30 | 20 | 73 | 50 |
| MT-5950 | 1 + 4 | 76 | 100 | 37 | 100 | MT-5950 | 1 + 4 | 70 | 50 | 73 | 40 |
| | 1 + 8 | 88 | 100 | 44 | 100 | | 1 + 8 | 85 | 70 | 76 | 50 |
| | 2 + 2 | 58 | 100 | 55 | 100 | | 2 + 2 | 30 | 30 | 87 | 50 |
| | 2 + 4 | 82 | 100 | 55 | 100 | | 2 + 4 | 70 | 50 | 87 | 70 |
| | 2 + 8 | 91 | 100 | 60 | 100 | | 2 + 8 | 85 | 50 | 88 | 70 |
| (Compound 7) | 1 | | 10 | | 10 | (Compound 39) | 1 | | 10 | | 10 |
| | 2 | | 50 | | 20 | | 2 | | 30 | | 20 |

TABLE 9-continued

| Sample Compound | Application rate (g/a) | Herbicidal effects Redroot pigweed Ec | Redroot pigweed Ea | Johnsongrass Ec | Johnsongrass Ea | Sample Compoound | Application rate (g/a) | Herbicidal effects Redroot pigweed Ec | Redroot pigweed Ea | Johnsongrass Ec | Johnsongrass Ea |
|---|---|---|---|---|---|---|---|---|---|---|---|
| Bentazon | 2 | | 30 | | 0 | Bentazon | 2 | | 30 | | 0 |
| | 4 | | 40 | | 0 | | 4 | | 40 | | 0 |
| | 8 | | 70 | | 20 | | 8 | | 70 | | 20 |
| (Compound 7) + | 1 + 2 | 37 | 100 | 10 | 100 | (Compound 39) + | 1 + 2 | 37 | 100 | 10 | 100 |
| Bentazon | 1 + 4 | 46 | 100 | 10 | 100 | Bentazon | 1 + 4 | 46 | 100 | 10 | 100 |
| | 1 + 8 | 73 | 100 | 28 | 100 | | 1 + 8 | 73 | 100 | 28 | 100 |
| | 2 + 2 | 65 | 100 | 20 | 100 | | 2 + 2 | 51 | 100 | 20 | 100 |
| | 2 + 4 | 70 | 100 | 20 | 100 | | 2 + 4 | 58 | 100 | 20 | 100 |
| | 2 + 8 | 85 | 100 | 36 | 100 | | 2 + 8 | 79 | 100 | 36 | 100 |
| (Compound 9) | 1 | | 10 | | 10 | (Compound 44) | 1 | | 10 | | 10 |
| | 2 | | 30 | | 20 | | 2 | | 20 | | 10 |
| Bentazon | 2 | | 30 | | 0 | Bentazon | 2 | | 30 | | 0 |
| | 4 | | 40 | | 0 | | 4 | | 40 | | 0 |
| | 8 | | 70 | | 20 | | 8 | | 70 | | 20 |
| (Compound 9) + | 1 + 2 | 37 | 100 | 10 | 100 | (Compound 44) + | 1 + 2 | 37 | 100 | 10 | 100 |
| Bentazon | 1 + 4 | 46 | 100 | 10 | 100 | Bentazon | 1 + 4 | 46 | 100 | 10 | 100 |
| | 1 + 8 | 73 | 100 | 28 | 100 | | 1 + 8 | 73 | 100 | 28 | 100 |
| | 2 + 2 | 51 | 100 | 20 | 100 | | 2 + 2 | 44 | 100 | 10 | 100 |
| | 2 + 4 | 58 | 100 | 20 | 100 | | 2 + 4 | 52 | 100 | 10 | 100 |
| | 2 + 8 | 79 | 100 | 36 | 100 | | 2 + 8 | 76 | 100 | 28 | 100 |
| (Compound 13) | 1 | | 20 | | 30 | Sethoxydim | 1 | | 0 | | 70 |
| | 2 | | 40 | | 50 | | 2 | | 0 | | 85 |
| Bentazon | 2 | | 30 | | 0 | Bentazon | 2 | | 30 | | 0 |
| | 4 | | 40 | | 0 | | 4 | | 40 | | 0 |
| | 8 | | 70 | | 20 | | 8 | | 70 | | 20 |
| (Compound 13) + | 1 + 2 | 44 | 100 | 30 | 100 | Sethoxydim + | 1 + 2 | 30 | 20 | 70 | 40 |
| Bentazon | 1 + 4 | 52 | 100 | 30 | 100 | Bentazon | 1 + 4 | 40 | 30 | 70 | 40 |
| | 1 + 8 | 76 | 100 | 44 | 100 | | 1 + 8 | 70 | 50 | 76 | 50 |
| | 2 + 2 | 58 | 100 | 50 | 100 | | 2 + 2 | 30 | 30 | 85 | 50 |
| | 2 + 4 | 64 | 100 | 50 | 100 | | 2 + 4 | 40 | 50 | 85 | 50 |
| | 2 + 8 | 82 | 100 | 60 | 100 | | 2 + 8 | 70 | 50 | 88 | 70 |
| (Compound 7) | 1 | | 10 | | 10 | (Compound 39) | 1 | | 10 | | 10 |
| | 2 | | 50 | | 20 | | 2 | | 30 | | 20 |
| Naptalam | 4 | | 0 | | 0 | Naptalam | 4 | | 0 | | 0 |
| | 8 | | 10 | | 10 | | 8 | | 10 | | 10 |
| | 16 | | 20 | | 20 | | 16 | | 20 | | 20 |
| (Compound 7) + | 1 + 4 | 10 | 100 | 10 | 100 | (Compound 39) + | 1 + 4 | 10 | 100 | 10 | 100 |
| Naptalam | 1 + 8 | 19 | 100 | 19 | 100 | Naptalam | 1 + 8 | 19 | 100 | 19 | 100 |
| | 1 + 16 | 28 | 100 | 28 | 100 | | 1 + 16 | 28 | 100 | 28 | 100 |
| | 2 + 4 | 50 | 100 | 20 | 100 | | 2 + 4 | 30 | 100 | 20 | 100 |
| | 2 + 8 | 55 | 100 | 28 | 100 | | 2 + 8 | 37 | 100 | 28 | 100 |
| | 2 + 16 | 60 | 100 | 36 | 100 | | 2 + 16 | 44 | 100 | 36 | 100 |
| (Compound 9) | 1 | | 10 | | 10 | (Compound 44) | 1 | | 10 | | 10 |
| | 2 | | 30 | | 20 | | 2 | | 20 | | 10 |
| Naptalam | 4 | | 0 | | 0 | Naptalam | 4 | | 0 | | 0 |
| | 8 | | 10 | | 10 | | 8 | | 10 | | 10 |
| | 16 | | 20 | | 20 | | 16 | | 20 | | 20 |
| (Compound 9) + | 1 + 4 | 10 | 100 | 10 | 100 | (Compound 44) + | 1 + 4 | 10 | 100 | 10 | 100 |
| Naptalam | 1 + 8 | 19 | 100 | 19 | 100 | Naptalam | 1 + 8 | 19 | 100 | 19 | 100 |
| | 1 + 16 | 28 | 100 | 28 | 100 | | 1 + 16 | 28 | 100 | 28 | 100 |
| | 2 + 4 | 30 | 100 | 20 | 100 | | 2 + 4 | 20 | 100 | 10 | 100 |
| | 2 + 8 | 37 | 100 | 28 | 100 | | 2 + 8 | 28 | 100 | 19 | 100 |
| | 2 + 16 | 44 | 100 | 36 | 100 | | 2 + 16 | 36 | 100 | 28 | 100 |
| (Compound 13) | 1 | | 20 | | 30 | Sethoxydim | 1 | | 0 | | 70 |
| | 2 | | 40 | | 50 | | 2 | | 0 | | 85 |
| Naptalam | 4 | | 0 | | 0 | Naptalam | 4 | | 0 | | 0 |
| | 8 | | 10 | | 10 | | 8 | | 10 | | 10 |
| | 16 | | 20 | | 20 | | 16 | | 20 | | 20 |
| (Compound 13) + | 1 + 4 | 20 | 100 | 30 | 100 | Sethoxydim + | 1 + 4 | 0 | 0 | 70 | 20 |
| Naptalam | 1 + 8 | 28 | 100 | 37 | 100 | Naptalam | 1 + 8 | 10 | 0 | 73 | 20 |
| | 1 + 16 | 36 | 100 | 44 | 100 | | 1 + 16 | 20 | 10 | 76 | 40 |
| | 2 + 4 | 40 | 100 | 50 | 100 | | 2 + 4 | 0 | 0 | 85 | 30 |
| | 2 + 8 | 46 | 100 | 55 | 100 | | 2 + 8 | 10 | 0 | 87 | 40 |
| | 2 + 16 | 52 | 100 | 60 | 100 | | 2 + 16 | 20 | 10 | 88 | 50 |

Test 9:
Test on Fast-Acting Property of Mixed Formulation in Upland Foliar Application Resin-made 1/10000-are pots were filled with the soil of an upland field. Redroot pigweed, johnsongrass and barnyardgrass were separately seeded and were allowed to germinate in a green house. When each plant grew to the stage of 2-3 leaves, emulsion formulated respectively from predetermined amounts of test compounds alone and predetermined amounts of mixtures with other herbicides in a similar manner to the method described in Formulation Example 16 were diluted with water to a predetermined dilution rate and then sprayed at an application rate equal to 5 l per are onto the foliage of each plant by means of a pressure-operated ULV (ultra low volume) sprayer. Influence to the weeds were observed on the 7th, 14th, 21st and 35th days after the spray of the herbicides. The results are shown in Table 10. In the table, the degrees of damages to the respective test plants and the degrees of injury of the crops are shown similarly to Test 2.

The results of the present test indicate the effects of mixing that the compounds of the invention can kill weeds in 7 days when applied in combination with other herbicides although they require as many as 30–50 days for killing the weeds when used singly.

TABLE 10

Time Required until Development of Effects

| Sample compound | | Application Rate (kg/ha) | | Weed control effects | | | | | | | | | | | |
|---|---|---|---|---|---|---|---|---|---|---|---|---|---|---|---|
| Ingredient I | Ingredient II | | | Redroot pigweed (days) | | | | Barnyardgrass (days) | | | | Johnsongrass (days) | | | |
| Comp'd No. | Ingredient Name | Ingredient I | Ingredient II | 7 | 14 | 21 | 35 | 7 | 14 | 21 | 35 | 7 | 14 | 21 | 35 |
|  | Linuron |  | 0.1 | 2 | 3 | 3 | 2 | 1 | 1 | 1 | 1 | 2 | 2 | 1 | 1 |
|  |  |  | 0.2 | 3 | 4 | 4 | 4 | 2 | 2 | 2 | 1 | 2 | 2 | 2 | 1 |
| 7 | — | 0.2 |  | 2 | 3 | 3 | 3 | 1 | 1 | 1 | 1 | 2 | 3 | 3 | 3 |
|  |  | 0.4 |  | 2 | 3 | 3 | 3 | 2 | 2 | 2 | 2 | 2 | 3 | 3 | 4 |
|  |  | 0.8 |  | 3 | 4 | 4 | 5 | 2 | 2 | 3 | 4 | 3 | 3 | 4 | 5 |
| 7 | Linuron | 0.2 | 0.1 | 5 | 5 | 5 | 5 | 4 | 4 | 4 | 4 | 5 | 5 | 5 | 5 |
|  |  | 0.2 | 0.2 | 5 | 5 | 5 | 5 | 4 | 4 | 4 | 5 | 5 | 5 | 5 | 5 |
|  |  | 0.4 | 0.1 | 5 | 5 | 5 | 5 | 4 | 4 | 4 | 5 | 5 | 5 | 5 | 5 |
|  |  | 0.4 | 0.2 | 5 | 5 | 5 | 5 | 4 | 4 | 5 | 5 | 5 | 5 | 5 | 5 |
|  |  | 0.8 | 0.1 | 5 | 5 | 5 | 5 | 4 | 5 | 5 | 5 | 5 | 5 | 5 | 5 |
|  |  | 0.8 | 0.2 | 5 | 5 | 5 | 5 | 5 | 5 | 5 | 5 | 5 | 5 | 5 | 5 |
| 9 | — | 0.2 |  | 2 | 2 | 3 | 4 | 1 | 1 | 1 | 1 | 2 | 3 | 3 | 3 |
|  |  | 0.4 |  | 2 | 3 | 4 | 4 | 2 | 2 | 3 | 3 | 3 | 3 | 4 | 4 |
|  |  | 0.8 |  | 3 | 4 | 4 | 5 | 2 | 2 | 3 | 4 | 3 | 3 | 4 | 5 |
| 9 | Linuron | 0.2 | 0.1 | 5 | 5 | 5 | 5 | 4 | 4 | 4 | 5 | 5 | 5 | 5 | 5 |
|  |  | 0.2 | 0.2 | 5 | 5 | 5 | 5 | 4 | 4 | 4 | 5 | 5 | 5 | 5 | 5 |
|  |  | 0.4 | 0.1 | 5 | 5 | 5 | 5 | 4 | 4 | 4 | 5 | 5 | 5 | 5 | 5 |
|  |  | 0.4 | 0.2 | 5 | 5 | 5 | 5 | 4 | 4 | 5 | 5 | 5 | 5 | 5 | 5 |
|  |  | 0.8 | 0.1 | 5 | 5 | 5 | 5 | 4 | 5 | 5 | 5 | 5 | 5 | 5 | 5 |
|  |  | 0.8 | 0.2 | 5 | 5 | 5 | 5 | 5 | 5 | 5 | 5 | 5 | 5 | 5 | 5 |
| 13 | — | 0.2 |  | 2 | 2 | 2 | 2 | 1 | 1 | 1 | 1 | 2 | 3 | 3 | 4 |
|  |  | 0.4 |  | 2 | 2 | 2 | 2 | 2 | 2 | 3 | 3 | 3 | 3 | 3 | 4 |
|  |  | 0.8 |  | 2 | 2 | 2 | 2 | 1 | 2 | 3 | 4 | 3 | 3 | 4 | 5 |
| 13 | Linuron | 0.2 | 0.1 | 5 | 5 | 5 | 5 | 4 | 4 | 4 | 5 | 5 | 5 | 5 | 5 |
|  |  | 0.2 | 0.2 | 5 | 5 | 5 | 5 | 4 | 4 | 4 | 5 | 5 | 5 | 5 | 5 |
|  |  | 0.4 | 0.1 | 5 | 5 | 5 | 5 | 4 | 4 | 5 | 5 | 5 | 5 | 5 | 5 |
|  |  | 0.4 | 0.2 | 5 | 5 | 5 | 5 | 4 | 4 | 5 | 5 | 5 | 5 | 5 | 5 |
|  |  | 0.8 | 0.1 | 5 | 5 | 5 | 5 | 5 | 5 | 5 | 5 | 5 | 5 | 5 | 5 |
|  |  | 0.8 | 0.2 | 5 | 5 | 5 | 5 | 5 | 5 | 5 | 5 | 5 | 5 | 5 | 5 |
| 44 | — | 0.2 |  | 2 | 2 | 2 | 4 | 1 | 2 | 2 | 2 | 2 | 2 | 3 | 3 |
|  |  | 0.4 |  | 2 | 2 | 3 | 4 | 2 | 2 | 3 | 3 | 2 | 3 | 4 | 4 |
|  |  | 0.8 |  | 3 | 4 | 4 | 5 | 2 | 2 | 3 | 4 | 3 | 3 | 4 | 5 |
| 44 | Linuron | 0.2 | 0.1 | 5 | 5 | 5 | 5 | 3 | 4 | 4 | 5 | 5 | 5 | 5 | 5 |
|  |  | 0.2 | 0.2 | 5 | 5 | 5 | 5 | 4 | 4 | 5 | 5 | 5 | 5 | 5 | 5 |
|  |  | 0.4 | 0.1 | 5 | 5 | 5 | 5 | 4 | 5 | 5 | 5 | 5 | 5 | 5 | 5 |
|  |  | 0.4 | 0.2 | 5 | 5 | 5 | 5 | 4 | 4 | 5 | 5 | 5 | 5 | 5 | 5 |
|  |  | 0.8 | 0.1 | 5 | 5 | 5 | 5 | 5 | 5 | 5 | 5 | 5 | 5 | 5 | 5 |
|  |  | 0.8 | 0.2 | 5 | 5 | 5 | 5 | 5 | 5 | 5 | 5 | 5 | 5 | 5 | 5 |
|  | Diuron |  | 0.2 | 2 | 2 | 2 | 2 | 1 | 1 | 1 | 1 | 1 | 2 | 1 | 1 |
|  |  |  | 0.4 | 3 | 3 | 3 | 4 | 2 | 2 | 1 | 1 | 2 | 2 | 2 | 1 |
| 9 | — | 0.2 |  | 1 | 2 | 3 | 3 | 1 | 1 | 1 | 1 | 2 | 3 | 3 | 3 |
|  |  | 0.4 |  | 2 | 3 | 4 | 4 | 2 | 2 | 2 | 3 | 2 | 3 | 3 | 4 |
|  |  | 0.8 |  | 3 | 4 | 4 | 5 | 2 | 2 | 3 | 4 | 3 | 3 | 4 | 5 |
| 9 | Diuron | 0.2 | 0.2 | 5 | 5 | 5 | 5 | 4 | 4 | 4 | 5 | 5 | 5 | 5 | 5 |
|  |  | 0.2 | 0.4 | 5 | 5 | 5 | 5 | 4 | 4 | 4 | 5 | 5 | 5 | 5 | 5 |
|  |  | 0.4 | 0.2 | 5 | 5 | 5 | 5 | 4 | 4 | 4 | 5 | 5 | 5 | 5 | 5 |
|  |  | 0.4 | 0.4 | 5 | 5 | 5 | 5 | 4 | 4 | 5 | 5 | 5 | 5 | 5 | 5 |
|  |  | 0.8 | 0.2 | 5 | 5 | 5 | 5 | 4 | 5 | 5 | 5 | 5 | 5 | 5 | 5 |
|  |  | 0.8 | 0.4 | 5 | 5 | 5 | 5 | 5 | 5 | 5 | 5 | 5 | 5 | 5 | 5 |
| 20 | — | 0.2 |  | 2 | 2 | 3 | 3 | 1 | 1 | 2 | 2 | 1 | 1 | 1 | 1 |
|  |  | 0.4 |  | 2 | 3 | 4 | 4 | 2 | 2 | 3 | 3 | 2 | 2 | 3 | 4 |
|  |  | 0.8 |  | 3 | 4 | 4 | 5 | 2 | 2 | 3 | 4 | 3 | 3 | 4 | 5 |
| 20 | Diuron | 0.2 | 0.2 | 5 | 5 | 5 | 5 | 4 | 4 | 4 | 5 | 5 | 5 | 5 | 5 |
|  |  | 0.2 | 0.4 | 5 | 5 | 5 | 5 | 4 | 4 | 5 | 5 | 5 | 5 | 5 | 5 |
|  |  | 0.4 | 0.2 | 5 | 5 | 5 | 5 | 4 | 4 | 5 | 5 | 5 | 5 | 5 | 5 |
|  |  | 0.4 | 0.4 | 5 | 5 | 5 | 5 | 4 | 5 | 5 | 5 | 5 | 5 | 5 | 5 |
|  |  | 0.8 | 0.2 | 5 | 5 | 5 | 5 | 4 | 5 | 5 | 5 | 5 | 5 | 5 | 5 |
|  |  | 0.8 | 0.4 | 5 | 5 | 5 | 5 | 5 | 5 | 5 | 5 | 5 | 5 | 5 | 5 |
| 39 | — | 0.2 |  | 2 | 2 | 3 | 3 | 1 | 1 | 1 | 1 | 2 | 2 | 3 | 3 |
|  |  | 0.4 |  | 2 | 3 | 4 | 4 | 2 | 2 | 3 | 3 | 3 | 2 | 3 | 4 |
|  |  | 0.8 |  | 3 | 3 | 4 | 5 | 2 | 2 | 3 | 4 | 3 | 3 | 4 | 5 |
| 39 | Diuron | 0.2 | 0.2 | 5 | 5 | 5 | 5 | 4 | 4 | 4 | 5 | 5 | 5 | 5 | 5 |
|  |  | 0.2 | 0.4 | 5 | 5 | 5 | 5 | 4 | 4 | 4 | 5 | 5 | 5 | 5 | 5 |
|  |  | 0.4 | 0.2 | 5 | 5 | 5 | 5 | 4 | 4 | 5 | 5 | 5 | 5 | 5 | 5 |
|  |  | 0.4 | 0.4 | 5 | 5 | 5 | 5 | 4 | 4 | 5 | 5 | 5 | 5 | 5 | 5 |
|  |  | 0.8 | 0.2 | 5 | 5 | 5 | 5 | 4 | 5 | 5 | 5 | 5 | 5 | 5 | 5 |
|  |  | 0.8 | 0.4 | 5 | 5 | 5 | 5 | 5 | 5 | 5 | 5 | 5 | 5 | 5 | 5 |
| 51 | — | 0.2 |  | 2 | 2 | 3 | 3 | 1 | 1 | 2 | 1 | 2 | 2 | 3 | 3 |
|  |  | 0.4 |  | 2 | 3 | 3 | 4 | 2 | 2 | 3 | 3 | 2 | 3 | 4 | 4 |
|  |  | 0.8 |  | 3 | 4 | 4 | 5 | 2 | 2 | 3 | 4 | 3 | 3 | 4 | 5 |
| 51 | Diuron | 0.2 | 0.2 | 5 | 5 | 5 | 5 | 4 | 4 | 4 | 5 | 5 | 5 | 5 | 5 |

TABLE 10-continued

Time Required until Development of Effects

| Sample compound | | Application Rate (kg/ha) | | Weed control effects | | | | | | | | | | | |
|---|---|---|---|---|---|---|---|---|---|---|---|---|---|---|---|
| Ingredient I | Ingredient II | | | Redroot pigweed (days) | | | | Barnyardgrass (days) | | | | Johnsongrass (days) | | | |
| Comp'd No. | Ingredient Name | Ingredient I | Ingredient II | 7 | 14 | 21 | 35 | 7 | 14 | 21 | 35 | 7 | 14 | 21 | 35 |
| | | 0.2 | 0.4 | 5 | 5 | 5 | 5 | 4 | 4 | 4 | 5 | 5 | 5 | 5 | 5 |
| | | 0.4 | 0.2 | 5 | 5 | 5 | 5 | 4 | 4 | 4 | 5 | 5 | 5 | 5 | 5 |
| | | 0.4 | 0.4 | 5 | 5 | 5 | 5 | 4 | 4 | 5 | 5 | 5 | 5 | 5 | 5 |
| | | 0.8 | 0.2 | 5 | 5 | 5 | 5 | 4 | 5 | 5 | 5 | 5 | 5 | 5 | 5 |
| | | 0.8 | 0.4 | 5 | 5 | 5 | 5 | 5 | 5 | 5 | 5 | 5 | 5 | 5 | 5 |
| | Atrazin | | 0.4 | 1 | 2 | 2 | 2 | 1 | 1 | 1 | 1 | 1 | 1 | 1 | 1 |
| | | | 0.8 | 2 | 2 | 3 | 2 | 2 | 1 | 2 | 1 | 1 | 2 | 2 | 1 |
| 4 | — | 0.2 | | 1 | 1 | 2 | 3 | 1 | 1 | 1 | 1 | 1 | 2 | 2 | 2 |
| | | 0.4 | | 2 | 2 | 3 | 4 | 1 | 2 | 3 | 3 | 1 | 2 | 2 | 4 |
| | | 0.8 | | 3 | 4 | 4 | 5 | 2 | 2 | 3 | 4 | 2 | 3 | 4 | 5 |
| 4 | Atrazin | 0.2 | 0.4 | 5 | 5 | 5 | 5 | 3 | 3 | 4 | 4 | 5 | 5 | 5 | 5 |
| | | 0.2 | 0.8 | 5 | 5 | 5 | 5 | 3 | 4 | 4 | 4 | 5 | 5 | 5 | 5 |
| | | 0.4 | 0.4 | 5 | 5 | 5 | 5 | 4 | 4 | 4 | 5 | 5 | 5 | 5 | 5 |
| | | 0.4 | 0.8 | 5 | 5 | 5 | 5 | 4 | 5 | 5 | 5 | 5 | 5 | 5 | 5 |
| | | 0.8 | 0.4 | 5 | 5 | 5 | 5 | 4 | 5 | 5 | 5 | 5 | 5 | 5 | 5 |
| | | 0.8 | 0.8 | 5 | 5 | 5 | 5 | 5 | 5 | 5 | 5 | 5 | 5 | 5 | 5 |
| 15 | — | 0.4 | | 1 | 1 | 2 | 4 | 1 | 1 | 1 | 1 | 1 | 1 | 1 | 1 |
| | | 0.8 | | 1 | 2 | 2 | 4 | 1 | 2 | 3 | 3 | 1 | 2 | 2 | 4 |
| | | 1.6 | | 3 | 4 | 4 | 5 | 2 | 2 | 3 | 4 | 3 | 3 | 4 | 5 |
| 15 | Atrazin | 0.4 | 0.4 | 5 | 5 | 5 | 5 | 4 | 4 | 4 | 5 | 5 | 5 | 5 | 5 |
| | | 0.4 | 0.8 | 5 | 5 | 5 | 5 | 4 | 4 | 4 | 5 | 5 | 5 | 5 | 5 |
| | | 0.8 | 0.4 | 5 | 5 | 5 | 5 | 4 | 5 | 5 | 5 | 5 | 5 | 5 | 5 |
| | | 0.8 | 0.8 | 5 | 5 | 5 | 5 | 4 | 5 | 5 | 5 | 5 | 5 | 5 | 5 |
| | | 1.6 | 0.4 | 5 | 5 | 5 | 5 | 5 | 5 | 5 | 5 | 5 | 5 | 5 | 5 |
| | | 1.6 | 0.8 | 5 | 5 | 5 | 5 | 5 | 5 | 5 | 5 | 5 | 5 | 5 | 5 |
| 26 | — | 0.2 | | 2 | 2 | 3 | 4 | 2 | 2 | 2 | 3 | 2 | 3 | 3 | 4 |
| | | 0.4 | | 2 | 3 | 4 | 4 | 2 | 2 | 3 | 3 | 3 | 3 | 4 | 5 |
| | | 0.8 | | 3 | 4 | 4 | 5 | 2 | 2 | 3 | 4 | 3 | 3 | 4 | 5 |
| 26 | Atrazin | 0.2 | 0.4 | 5 | 5 | 5 | 5 | 4 | 5 | 5 | 5 | 5 | 5 | 5 | 5 |
| | | 0.2 | 0.8 | 5 | 5 | 5 | 5 | 5 | 5 | 5 | 5 | 5 | 5 | 5 | 5 |
| | | 0.4 | 0.4 | 5 | 5 | 5 | 5 | 5 | 5 | 5 | 5 | 5 | 5 | 5 | 5 |
| | | 0.4 | 0.8 | 5 | 5 | 5 | 5 | 5 | 5 | 5 | 5 | 5 | 5 | 5 | 5 |
| | | 0.8 | 0.4 | 5 | 5 | 5 | 5 | 5 | 5 | 5 | 5 | 5 | 5 | 5 | 5 |
| | | 0.8 | 0.8 | 5 | 5 | 5 | 5 | 5 | 5 | 5 | 5 | 5 | 5 | 5 | 5 |
| 47 | — | 0.2 | | 1 | 1 | 2 | 3 | 1 | 1 | 1 | 3 | 1 | 2 | 2 | 2 |
| | | 0.4 | | 1 | 2 | 3 | 3 | 2 | 2 | 3 | 3 | 2 | 2 | 3 | 4 |
| | | 0.8 | | 2 | 3 | 4 | 5 | 2 | 2 | 3 | 4 | 3 | 3 | 4 | 5 |
| 47 | Atrazin | 0.2 | 0.4 | 4 | 4 | 5 | 5 | 4 | 4 | 4 | 4 | 5 | 5 | 5 | 5 |
| | | 0.2 | 0.8 | 5 | 5 | 5 | 5 | 4 | 4 | 4 | 4 | 5 | 5 | 5 | 5 |
| | | 0.4 | 0.4 | 5 | 5 | 5 | 5 | 4 | 5 | 5 | 5 | 5 | 5 | 5 | 5 |
| | | 0.4 | 0.8 | 5 | 5 | 5 | 5 | 4 | 5 | 5 | 5 | 5 | 5 | 5 | 5 |
| | | 0.8 | 0.4 | 5 | 5 | 5 | 5 | 4 | 5 | 5 | 5 | 5 | 5 | 5 | 5 |
| | | 0.8 | 0.8 | 5 | 5 | 5 | 5 | 5 | 5 | 5 | 5 | 5 | 5 | 5 | 5 |
| | Bentazon | | 0.4 | 2 | 3 | 3 | 2 | 1 | 1 | 0 | 0 | 0 | 0 | 0 | 0 |
| | | | 0.8 | 3 | 4 | 4 | 4 | 2 | 2 | 2 | 1 | 1 | 1 | 2 | 1 |
| 1 | — | 0.2 | | 1 | 1 | 2 | 3 | 1 | 1 | 1 | 1 | 1 | 2 | 2 | 3 |
| | | 0.4 | | 2 | 3 | 4 | 4 | 2 | 2 | 3 | 3 | 3 | 3 | 4 | 4 |
| | | 0.8 | | 3 | 4 | 4 | 5 | 2 | 2 | 3 | 4 | 3 | 3 | 4 | 5 |
| 1 | Bentazon | 0.2 | 0.4 | 5 | 5 | 5 | 5 | 3 | 4 | 4 | 4 | 5 | 5 | 5 | 5 |
| | | 0.2 | 0.8 | 5 | 5 | 5 | 5 | 4 | 4 | 4 | 5 | 5 | 5 | 5 | 5 |
| | | 0.4 | 0.4 | 5 | 5 | 5 | 5 | 4 | 4 | 4 | 5 | 5 | 5 | 5 | 5 |
| | | 0.4 | 0.8 | 5 | 5 | 5 | 5 | 4 | 5 | 5 | 5 | 5 | 5 | 5 | 5 |
| | | 0.8 | 0.4 | 5 | 5 | 5 | 5 | 4 | 5 | 5 | 5 | 5 | 5 | 5 | 5 |
| | | 0.8 | 0.8 | 5 | 5 | 5 | 5 | 5 | 5 | 5 | 5 | 5 | 5 | 5 | 5 |
| 7 | — | 0.2 | | 1 | 2 | 2 | 3 | 1 | 2 | 2 | 2 | 1 | 2 | 2 | 3 |
| | | 0.4 | | 2 | 3 | 4 | 4 | 2 | 2 | 3 | 3 | 3 | 3 | 4 | 4 |
| | | 0.8 | | 3 | 4 | 4 | 5 | 2 | 2 | 3 | 4 | 3 | 3 | 4 | 5 |
| 7 | Bentazon | 0.2 | 0.4 | 5 | 5 | 5 | 5 | 4 | 4 | 4 | 5 | 5 | 5 | 5 | 5 |
| | | 0.2 | 0.8 | 5 | 5 | 5 | 5 | 5 | 5 | 5 | 5 | 5 | 5 | 5 | 5 |
| | | 0.4 | 0.4 | 5 | 5 | 5 | 5 | 5 | 5 | 5 | 5 | 5 | 5 | 5 | 5 |
| | | 0.4 | 0.8 | 5 | 5 | 5 | 5 | 5 | 5 | 5 | 5 | 5 | 5 | 5 | 5 |
| | | 0.8 | 0.4 | 5 | 5 | 5 | 5 | 5 | 5 | 5 | 5 | 5 | 5 | 5 | 5 |
| | | 0.8 | 0.8 | 5 | 5 | 5 | 5 | 5 | 5 | 5 | 5 | 5 | 5 | 5 | 5 |
| 12 | — | 0.4 | | 1 | 1 | 3 | 4 | 1 | 1 | 1 | 1 | 1 | 1 | 1 | 3 |
| | | 0.8 | | 1 | 2 | 4 | 4 | 1 | 2 | 3 | 3 | 1 | 3 | 4 | 4 |
| | | 1.6 | | 1 | 4 | 4 | 5 | 1 | 2 | 3 | 4 | 1 | 3 | 4 | 5 |
| 12 | Bentazon | 0.4 | 0.4 | 5 | 5 | 5 | 5 | 4 | 4 | 4 | 4 | 5 | 5 | 5 | 5 |
| | | 0.4 | 0.8 | 5 | 5 | 5 | 5 | 4 | 4 | 4 | 4 | 5 | 5 | 5 | 5 |
| | | 0.8 | 0.4 | 5 | 5 | 5 | 5 | 4 | 4 | 4 | 4 | 5 | 5 | 5 | 5 |
| | | 0.8 | 0.8 | 5 | 5 | 5 | 5 | 4 | 5 | 5 | 5 | 5 | 5 | 5 | 5 |
| | | 1.6 | 0.4 | 5 | 5 | 5 | 5 | 4 | 5 | 5 | 5 | 5 | 5 | 5 | 5 |
| | | 1.6 | 0.8 | 5 | 5 | 5 | 5 | 5 | 5 | 5 | 5 | 5 | 5 | 5 | 5 |
| 53 | — | 0.2 | | 1 | 1 | 2 | 3 | 1 | 1 | 3 | 4 | 1 | 3 | 3 | 3 |
| | | 0.4 | | 2 | 3 | 4 | 4 | 2 | 2 | 3 | 4 | 2 | 3 | 4 | 4 |
| | | 0.8 | | 3 | 4 | 4 | 5 | 2 | 2 | 3 | 4 | 3 | 3 | 4 | 5 |
| 53 | Bentazon | 0.2 | 0.4 | 5 | 5 | 5 | 5 | 4 | 4 | 5 | 5 | 4 | 4 | 4 | 5 |

TABLE 10-continued

| Sample compound | | Application Rate (kg/ha) | | Time Required until Development of Effects | | | | | | | | | | | |
|---|---|---|---|---|---|---|---|---|---|---|---|---|---|---|---|
| | | | | Weed control effects | | | | | | | | | | | |
| | | | | Redroot pigweed (days) | | | | Barnyardgrass (days) | | | | Johnsongrass (days) | | | |
| Ingredient I Comp'd No. | Ingredient II Ingredient Name | Ingredient I | Ingredient II | 7 | 14 | 21 | 35 | 7 | 14 | 21 | 35 | 7 | 14 | 21 | 35 |
| | | 0.2 | 0.8 | 5 | 5 | 5 | 5 | 4 | 4 | 5 | 5 | 5 | 5 | 5 | 5 |
| | | 0.4 | 0.4 | 5 | 5 | 5 | 5 | 5 | 5 | 5 | 5 | 5 | 5 | 5 | 5 |
| | | 0.4 | 0.8 | 5 | 5 | 5 | 5 | 4 | 4 | 5 | 5 | 5 | 5 | 5 | 5 |
| | | 0.8 | 0.4 | 5 | 5 | 5 | 5 | 4 | 5 | 5 | 5 | 5 | 5 | 5 | 5 |
| | | 0.8 | 0.8 | 5 | 5 | 5 | 5 | 5 | 5 | 5 | 5 | 5 | 5 | 5 | 5 |

We claim:
1. A 2-(4,6-dimethoxy-2-pyrimidinyloxy)benzaldoxime.
2. A 2-(4,6-dimethoxy-2-pyrimidinyloxy)benzaldoxime represented by the following formula:

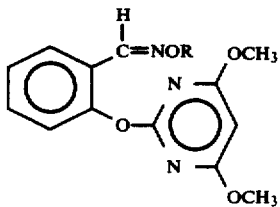

wherein R represents a hydrogen atom; a lower alkyl, lower alkenyl, lower alkynyl, phenyl-substiututed lower alkenyl, lower haloalkenyl, cycloalkyl of 3 to 6 ring carbon atoms, substituted phenyl-lower alkenyl wherein the phenyl group bears one or more alkyl, alkoxy and trifluoromethyl groups or halogen atoms or phenyl-substituted lower alkynyl group; or a group represented by the following formula:

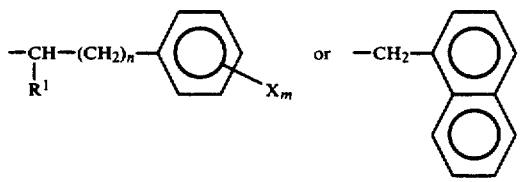

wherein $R^1$ represents a hydrogen atom or a lower alkyl group, X a halogen atom or a lower alkyl or lower alkoxyl group, m and n individually 0-2, and when m is 2, both Xs may be the same or different.

3. The 2-(4,6-dimethoxy-2-pyrimidinyloxy)benzaldoxime of claim 2, wherein R is a lower alkenyl group.
4. The 2-(4,6-dimethoxy-2-pyrimidinyloxy)benzaldoxime of claim 3, wherein the lower alkenyl group is 3-methyl-2-butenyl group.
5. The 2-(4,6-dimethoxy-2-pyrimidinyloxy)benzaldoxime of claim 2, wherein R is a 2-propynyl group.
6. The 2-(4,6-dimethoxy-2-pyrimidinyloxy)benzaldoxime of claim 2, wherein R is a lower haloalkenyl group.
7. The 2-(4,6-dimethoxy-2-pyrimidinyloxy)benzaldoxime of claim 6, wherein the lower haloalkenyl group is 3-chloro-2-propenyl group.
8. The 2-(4,6-dimethoxy-2-pyrimidinyloxy)benzaldoxime of claim 6, wherein the lower haloalkenyl group is 3-chloro-2-butenyl group.
9. The 2-(4,6-dimethoxy-2-pyrimdinyloxy)benzaldoxime of claim 2, wherein R is a 3-(phenyl-lower alkenyl group wherein the phenyl group is unsubstituted or bears one or more of alkyl, alkoxy and trifluoromethyl groups or halogen atoms.
10. The 2-(4,6-dimethoxy-2-pyrimidinyloxy)benzaldoxime of claim 2, wherein R is a 3-phenyl-2-propenyl group.
11. A herbicide composition comprising as herbicidally active ingredient, in admixture with a carrier, a 2-(4,6-dimethoxy-2-pyrimidinyloxy)benzaldoxime of claim 2.
12. The composition of claim 11, wherein R in the formula is lower-alkenyl.
13. The composition of claim 12, wherein R in the formula is 3-methyl-2-butenyl.
14. The composition of claim 11, wherein R in the formula is 2-propynyl.
15. The composition of claim 11, wherein R in the formula is haloalkenyl.
16. The composition of claim 15, wherein R in the formula is 3-chloro-2-propenyl.
17. The composition of claim 15, wherein R in the formula is 3-chloro-2-butenyl.
18. The composition of claim 11, wherein R in the formula is 3-phenyl-lower alkenyl, wherein the phenyl group is unsubstituted or bears one or more of alkyl, alkoxy and trifluoromethyl groups or halogen atoms.
19. The composition of claim 11, wherein R in the formula is 3-phenyl-2-propenyl, wherein the phenyl group is unsubstituted or bears one or more of alkyl, alkoxy and trifluoromethyl groups or halogen atoms.

* * * * *